United States Patent
Nanjundan et al.

(10) Patent No.: US 10,695,341 B2
(45) Date of Patent: Jun. 30, 2020

(54) COMPOSITIONS AND METHODS FOR TREATING ENDOMETRIOSIS

(71) Applicants: UNIVERSITY OF SOUTH FLORIDA, Tampa, FL (US); PONCE HEALTH SCIENCES UNIVERSITY, Ponce, PR (US)

(72) Inventors: Meera Nanjundan, Tampa, FL (US); Kyle A. Bauckman, St. Louis, MO (US); Idhaliz Flores, Ponce, PR (US)

(73) Assignees: University of South Florida, Tampa, FL (US); Ponce Health Sciences University, Ponce, PR (US)

( * ) Notice: Subject to any disclaimer, the term of this patent is extended or adjusted under 35 U.S.C. 154(b) by 0 days.

(21) Appl. No.: 15/527,998

(22) PCT Filed: Nov. 18, 2015

(86) PCT No.: PCT/US2015/061393
§ 371 (c)(1),
(2) Date: May 18, 2017

(87) PCT Pub. No.: WO2016/081634
PCT Pub. Date: May 26, 2016

(65) Prior Publication Data
US 2019/0388413 A1    Dec. 26, 2019

Related U.S. Application Data

(60) Provisional application No. 62/081,464, filed on Nov. 18, 2014.

(51) Int. Cl.
| | | |
|---|---|---|
| C07H 21/04 | (2006.01) |
| A61K 31/4706 | (2006.01) |
| A61P 15/00 | (2006.01) |
| A61K 31/4709 | (2006.01) |
| A61K 31/7105 | (2006.01) |
| C12N 15/113 | (2010.01) |
| G01N 33/68 | (2006.01) |

(52) U.S. Cl.
CPC ...... *A61K 31/4706* (2013.01); *A61K 31/4709* (2013.01); *A61K 31/7105* (2013.01); *A61P 15/00* (2018.01); *C12N 15/113* (2013.01); *G01N 33/689* (2013.01); *C12N 2310/14* (2013.01); *C12N 2320/31* (2013.01); *C12N 2320/32* (2013.01); *C12N 2320/35* (2013.01); *G01N 2333/46* (2013.01); *G01N 2800/364* (2013.01)

(58) Field of Classification Search
None
See application file for complete search history.

(56) References Cited

U.S. PATENT DOCUMENTS

| | | |
|---|---|---|
| 2009/0238876 A1 | 9/2009 | Danenberg et al. |
| 2011/0318335 A1 | 12/2011 | Newell et al. |
| 2017/0137825 A1* | 5/2017 | Niitsu ............ A61K 45/06 |

OTHER PUBLICATIONS

Zou, Yiyu, et al. "The autophagy inhibitor chloroquine overcomes the innate resistance of wild-type EGFR non-small-cell lung cancer cells to erlotinib." Journal of Thoracic Oncology 8.6 (2013): 693-702.*
Ning Chen & Vassiliki Karantza (2011) Autophagy as a therapeutic target in cancer, Cancer Biology & Therapy, 11:2, 157-168.*
Melin et al., Human Reproduction, vol. 21, Issue 5, May 2006, pp. 1237-1242.*
Efthimios Sivridis, Alexandra Giatromanolaki, Vasilios Liberis & Michael I. Koukourakis (2011) Autophagy in endometrial carcinomas and prognostic relevance of 'stone-like' structures (SLS): What is destined for the atypical endometrial hyperplasia?, Autophagy, 7:1, 74-82.*
Lu, Yan-Ming, et al. "Suppression of HER-2 via siRNA interference promotes apoptosis and decreases metastatic potential of SKOV-3 human ovarian carcinoma cells." Oncology reports 29.3 (2013): 1133-1139.
Liu, Jinsong, et al. "A genetically defined model for human ovarian cancer." Cancer research 64.5 (2004): 1655-1663.
Del Bufalo, Donatella, et al. "Involvement of hTERT in apoptosis induced by interference with Bcl-2 expression and function." Cell death and differentiation 12.11 (2005): 1429.
Nims, Raymond W., et al. "Short tandem repeat profiling: part of an overall strategy for reducing the frequency of cell misidentification." In Vitro Cellular & Developmental Biology-Animal 46.10 (2010): 811-819.
Choi, JongYeob, et al. "Differential induction of autophagy by mTOR is associated with abnormal apoptosis in ovarian endometriotic cysts." Molecular human reproduction 20.4 (2013): 309-317.
Kimura, Tomonori, et al. "Chloroquine in cancer therapy: a double-edged sword of autophagy." Cancer research 73:1 (2013): 3-7.
Guo, Jessie Yanxiang, and Eileen White. "Autophagy is required for mitochondrial function, lipid metabolism, growth, and fate of KRASG12D-driven lung tumors." Autophagy 9.10 (2013): 1636-1638.

(Continued)

*Primary Examiner* — Kimberly Chong
(74) *Attorney, Agent, or Firm* — Thomas | Horstemeyer, LLP

(57) ABSTRACT

Provided herein are methods of treating and/or preventing endometriosis or symptom thereof, assays for diagnosing/prognosing endometriosis, compositions and formulations for treating and/or preventing endometriosis or symptom thereof, and populations of endometiotic cells, including life-extended populations of cells.

11 Claims, 57 Drawing Sheets

Specification includes a Sequence Listing.

(56) References Cited

OTHER PUBLICATIONS

Strohecker, Anne M., and Eileen White. "Autophagy promotes Braf V600E-driven lung tumorigenesis by preserving mitochondrial metabolism." Autophagy 10.2 (2014): 384-385.
Yamada, Takaaki, et al. "Role of oxidative stress in vinorelbine-induced vascular endothelial cell injury." Free Radical Biology and Medicine 48.1 (2010): 120-127.
Oexle, Horst, Erich Gnaiger, and Günter Weiss. "Iron-dependent changes in cellular energy metabolism: influence on citric acid cycle and oxidative phosphorylation." Biochimica et Biophysica Acta (BBA)-Bioenergetics 1413.3 (1999): 99-107.
Wu, Yuliang, and Robert M. Brosh Jr. "DNA helicase and helicase-nuclease enzymes with a conserved iron-sulfur cluster." Nucleic acids research 40.10 (2012): 4247-4260.
Williams, Rachel, et al. "Pathogenic implications of iron accumulation in multiple sclerosis." Journal of neurochemistry 120.1 (2012): 7-25.
Ma, Yi-Shing, et al. "Response to the increase of oxidative stress and mutation of mitochondrial DNA in aging." Biochimica et Biophysica Ada (BBA)-General Subjects 1790.10 (2009): 1021-1029.
Hegde, Muralidhar L., et al. "Oxidative genome damage and its repair in neurodegenerative diseases: function of transition metals as a double-edged sword." Journal of Alzheimer's Disease 24.supplement2 (2011): 183-198.
Reif, Philipp, et al. "Rupture of endometriotic ovarian cyst causes acute hemoperitoneum in twin pregnancy." Fertility and sterility 95.6 (2011): 2125-e1.
Alcântara, D. D. F. A., et al. "Cellular responses induced in vitro by iron (Fe) in a central nervous system cell line (U343MGa)." Genetics and Molecular Research 12.2 (2013): 1554-1560.
Samouelian, V., et al. "Chemosensitivity and radiosensitivity profiles of four new human epithelial ovarian cancer cell ines exhibiting genetic alterations in BRCA2, TGFβ-RII, KRAS2, TP53 and/or CDNK2A." Cancer chemotherapy and pharmacology 54.6 (2004): 497-504.
Liu, Guangzhi, et al. "Stanniocalcin 1 and ovarian tumorigenesis." Journal of the National Cancer Institute 102.11 (2010): 812-827.
Fan, Heng-Yu, et al. "Consequences of RAS and MAPK activation in the ovary: the good, the bad and the ugly." Molecular and cellular endocrinology 356.1-2 (2012): 74-79.
Klionsky, Daniel J., et al. "Guidelines for the use and interpretation of assays for monitoring autophagy in higher eukaryotes." Autophagy 4.2 (2008): 151-175.
Komatsu, Masaaki, Shun Kageyama, and Yoshinobu Ichimura. "p62/SQSTM1/A170: physiology and pathology." Pharmacological Research 66.6 (2012): 457-462.
Moscat, Jorge, and Maria T. Diaz-Meso. "p62: a versatile multitasker takes on cancer." Trends in biochemical sciences 37.6 (2012): 230-236.
Ni, Hong-Min, et al. "Dissecting the dynamic turnover of GFP-LC3 in the autolysosome." Autophagy 7.2 (2011): 188-204.
Galluzzi, Lorenzo, et al. "Guidelines for the use and interpretation of assays for monitoring cell death in higher eukaryotes." Cell death and differentiation 16.8 (2009): 1093.
Sturm, Brigitte, Hans Goldenberg, and Barbara Scheiber-Mojdehkar. "Transient increase of the labile iron pool in HepG2 cells by intravenous iron preparations." European journal of biochemistry 270.18 (2003): 3731-3738.
Nlylandsted, Jesper, et al. "Heat shock protein 70 promotes cell survival by inhibiting lysosomal membrane permeabilization." Journal of Experimental Medicine 200.4 (2004): 425-435.
Uchiyama, Akira, et al. "Translocation of iron from lysosomes into mitochondria is a key event during oxidative stress-induced hepatocellular injury." Hepatology 48.5 (2008): 1644-1654.
Wei, Lin, et al. "Altered regulation of Src upon cell detachment protects human lung adenocarcinoma cells from anoikis." Oncogene 23.56 (2004): 9052.

Liu, Bing, et al. "Cyclooxygenase-2 inhibitors induce anoikis in osteosarcoma via PI3K/Akt pathway." Medical hypotheses 79.1 (2012): 98-100.
Ma, Z., et al. "p66 Shc restrains Ras hyperactivation and suppresses metastatic behavior." Oncogene 29.41 (2010): 5559.
Debnath, J. "p66 Shc and Ras: controlling anoikis from the inside-out." Oncogene 29.41 (2010): 5556.
Anger, Dana L., et al. "Tyrosine receptor kinase B (TrkB) protein expression in the human endometrium." Endocrine 31.2 (2007): 167-173.
Hong, Jin-hee, et al. "Iron promotes the survival and neurite extension of serum-starved PC12 cells in the presence of NGF by enhancing cell attachment." Molecules and cells 15.1 (2003): 10-19.
He, Xiaoping, et al. "Downregulation of HtrA1 promotes resistance to anoikis and peritoneal dissemination of ovarian cancer cells." Cancer research (2010): 0008-5472.
Caneba, Christine A., et al. "Pyruvate uptake is increased in highly invasive ovarian cancer cells under anoikis conditions for anaplerosis, mitochondrial function, and migration." American Journal of Physiology-Endocrinology and Metabolism 303.8 (2012): E1036-E1052.
Pagé, Viviane, et al. "BAG-1 p29 protein prevents drug-induced cell death in the presence of EGF and enhances resistance to anoikis in SKOV3 human ovarian cancer cells." Biochemical and biophysical research communications 328.4 (2005): 874-884.
Rubinstein, Assaf D., and Adi Kimchi. "Life in the balance—a mechanistic view of the crosstalk between autophagy and apoptosis." J Cell Sci 125.22 (2012): 5259-5268.
Sundqvist, J., et al. "Expression of adhesion, attachment and invasion markers in eutopic and ectopic endometrium: a link to the aetiology of endometriosis." Human reproduction 27.9 (2012): 2737-2746.
Somigliana, E., et al., Adhesion prevention in endometriosis: a neglected critical challenge. JMinim Invasive Gynecol, 2012. 19(4): p. 415-21.
Kaminskyy, Vitaliy O., et al. "Suppression of basal autophagy reduces lung cancer cell proliferation and enhances caspase-dependent and-independent apoptosis by stimulating ROS formation." Autophagy 8.7 (2012): 1032-1044.
Wu, Defeng, and Arthur I. Cederbaum. "Inhibition of autophagy promotes CYP2E1-dependent toxicity in HepG2 cells via elevated oxidative stress, mitochondria dysfunction and activation of p38 and JNK MAPK." Redox biology 1.1 (2013): 552-565.
Gandesiri, Muktheshwar, et al. "DAPK plays an important role in panobinostat-induced autophagy and commits cells to apoptosis under autophagy deficient conditions." Apoptosis 17.12 (2012): 1300-1315.
Zhu, Xingmei, et al. "Autophagy stimulates apoptosis in HER 2-overexpressing breast cancers treated by lapatinib." Journal of cellular biochemistry 114.12 (2013): 2643-2653.
Somigliana, E., et al. "Endometrial ability to implant in ectopic sites can be prevented by interleukin-12 in a murine model of endometriosis." Human Reproduction 14.12 (1999): 2944-2950.
Ye, Qing, et al. "ERK and AKT signaling cooperate to translationally regulate survivin expression for promotion of cell motility and metastasis in colorectal cancer." (2013): 3787-3787.
Zhang, Yanjie, and XF Steven Zheng. "mTOR-independent 4E-BP1 phosphorylation is associated with cancer resistance to mTOR kinase inhibitors." Cell cycle 11.3 (2012): 594-603.
Gallagher, Patricia J., and Emily K. Blue. "Post-translational regulation of the cellular levels of DAPK." Apoptosis 19.2 (2014): 306-315.
Martelli, Alain, et al. "Clinical data and characterization of the liver conditional mouse model exclude neoplasia as a non-neurological manifestation associated with Friedreich's ataxia." Disease models & mechanisms (2012): dmm-009829.
Wheater, Matthew J., Peter WM Johnson, and Jeremy R Blaydes. "The role of MNK proteins and eIF4E phosphorylation in breast cancer cell proliferation and survival." Cancer biology & therapy 10.7 (2010): 728-735.
Chang, Chia-Chu, et al. "Simvastatin downregulates the expression of hepcidin and erythropoietin in H ep G 2 cells." Hemodialysis International 17.1 (2013): 116-121.

(56) References Cited

OTHER PUBLICATIONS

Korch, C., et al., DNA profiling analysis of endometrial and ovarian cell lines revealsmisidentification, redundancy and contamination. Gynecol Oncol, 2012. 127(1): p. 241-8.

Bouquet de Joliniere, J., et al., Human endometriosis-derived permanent cell line (FbEM-1):establishment and characterization. Hum Reprod Update, 1997. 3(2): p. 117-23.

Kniss, Douglas A., and Taryn L. Summerfield. "Discovery of HeLa Cell contamination in HES Cells: Call for cell line authentication in reproductive biology research." Reproductive sciences 21.8 (2014): 1015-1019.

López, Jacqueline, et al. "Normal and cancer stem cells of the human female reproductive system." Reproductive Biology and Endocrinology 11.1 (2013): 53.

Borahay, Mostafa A., et al. "Mullerian inhibiting substance suppresses proliferation and induces apoptosis and autophagy in endometriosis cells in vitro." ISRN obstetrics and gynecology 2013 (2013).

Gozzelino, Raffaella, Viktoria Jeney, and Miguel P. Soares. "Mechanisms of cell protection by heme oxygenase-1." Annual review of pharmacology and toxicology 50 (2010): 323-354.

Banerjee, Pallavi, et al. "Heme oxygenase-1 is overexpressed in human renal cancer cells following activation of the Ras-Raf-ERK Pathway, and mediates anti-apoptotic signal." Journal of Biological Chemistry (2011): jbc-M111.

Porter, J. B., et al. "Recent insights into interactions of deferoxamine with cellular and plasma iron pools: implications for clinical use." Annals of the New York Academy of Sciences 1054.1 (2005): 155-168.

Ying, Tsung-Ho, et al. "Association of p53 and CDKN1A genotypes with endometriosis." Anticancer research 31.12 (2011): 4301-4306.

Yamaguchi, Ken, et al. "Contents of endometriotic cysts, especially the high concentration of free iron, are a possible cause of carcinogenesis in the cysts through the iron-induced persistent oxidative stress." Clinical Cancer Research 14.1 (2008): 32-40.

Xiao, Wenbin, Amad Awadallah, and Wei Xin. "Loss of ARID1A/BAF250a expression in ovarian endometriosis and clear cell carcinoma." International journal of clinical and experimental pathology 5.7 (2012): 642.

Wiegand, Kimberly C., et al. "ARID1A mutations in endometriosis-associated ovarian carcinomas." New England Journal of Medicine 363.16 (2010): 1532-1543.

Toyokuni, Y.Y.a.S., Endometriosis-Associated Ovarian Cancer: The Role of Oxidative Stress in Endometriosis—Basic Concepts and Current Research Trends, K. Chaudhury, Editor. 2012, Intech:Intech.

McConechy, Melissa K., et al. "Ovarian and endometrial endometrioid carcinomas have distinct CTNNB1 and PTEN mutation profiles." Modern Pathology 27.1 (2014): 128.

Lai, Chiung-Ru, et al. "Ovarian cancers arising from endometriosis: a microenvironmental biomarker study including ER, HNF1ss, p53, PTEN, BAF250a, and COX-2." Journal of the Chinese Medical Association 76.11 (2013): 629-634.

Anderson, Cole P., et al. "Mammalian iron metabolism and its control by iron regulatory proteins." Biochimica et Biophysica Acta (BBA)-Molecular Cell Research 1823.9 (2012): 1468-1483.

Valko, Marian, et al. "Free radicals, metals and antioxidants in oxidative stress-induced cancer." Chemico-biological Interactions 160.1 (2006): 1-40.

Richardson, Des R., et al. "Mitochondrial iron trafficking and the integration of iron metabolism between the mitochondrion and cytosol." Proceedings of the National Academy of Sciences 107.24 (2010): 10775-10782.

Kirches, Elmar, et al. "Dual role of the mitochondrial protein frataxin in astrocytic tumors." Laboratory Investigation 91.12 (2011): 1766.

Institute, N.C. http://www.cancer.gov/. 2013.

Klionsky, Daniel J., et al. "Guidelines for the use and interpretation of assays for monitoring autophagy." Autophagy 8.4 (2012): 445-544.

Torti, Suzy V., and Frank M. Torti. "Iron and cancer: more ore to be mined." Nature Reviews Cancer 13.5 (2013): 342.

Nadadur, S. S., K. Srirama, and Anuradha Mudipalli. "Iron transport & homeostasis mechanisms: their role in health & disease." Indian Journal of Medical Research 128.4 (2008): 533.

Ganz, Tomas, and Elizabeta Nemeth. "Hepcidin and iron homeostasis." Biochimica et Biophysica Acta (BBA)-Molecular Cell Research 1823.9 (2012): 1434-1443.

Bauckman, K. A., et al. "Iron modulates cell survival in a Ras-and MAPK-dependent manner in ovarian cells." Cell death & disease 4.4 (2013): e592.

Kurz, Tino, John W. Eaton, and Ulf T. Brunk. "The role of lysosomes in iron metabolism and recycling." The International journal of biochemistry & cell biology 43.12 (2011): 1686-1697.

Neto, João Siufi, et al. "Cellular, histologic, and molecular changes associated with endometriosis and ovarian cancer." Journal of minimally invasive gynecology 21.1 (2014): 55-63.

Seidman, Jeffrey D. "The presence of mucosal iron in the fallopian tube supports the "incessant menstruation hypothesis" for ovarian carcinoma." International Journal of Gynecological Pathology 32.5 (2013): 454-458.

Pratt, Joseph H., and William R. Shamblin. "Spontaneous rupture of endometrial cysts of the ovary presenting as an acute abdominal emergency." American Journal of Obstetrics & Gynecology 108.1 (1970): 56-62.

Ogawa, Shinji, et al. "Ovarian endometriosis associated with ovarian carcinoma: a clinicopathological and immunohistochemical study." Gynecologic oncology 77.2 (2000): 298-304.

Yamaguchi, K., et al. "Identification of an ovarian clear cell carcinoma gene signature that reflects inherent disease biology and the carcinogenic processes." Oncogene 29.12 (2010): 1741.

Defrère, Sylvie, et al. "Iron overload enhances epithelial cell proliferation in endometriotic lesions induced in a murine model." Human Reproduction 21.11 (2006): 2810-2816.

Boyraz, Gokhan, et al. "Ovarian carcinoma associated with endometriosis." European Journal of Obstetrics & Gynecology and Reproductive Biology 170.1 (2013): 211-213.

Fukunaga, M., et al. "Ovarian atypical endometriosis: its close association with malignant epithelial tumours." Histopathology 30.3 (1997): 249-255.

Heaps, James M., Roberta K. Nieberg, and Jonathan S. Berek. "Malignant neoplasms arising in endometriosis." Obstetrics and gynecology 75.6 (1990): 1023-1028.

Lim, D., and E. Oliva "Precursors and pathogenesis of ovarian carcinoma." Pathology 45.3 (2013): 229-242.

Kim, Ayako, et al. "Therapeutic strategies in epithelial ovarian cancer." Journal of experimental & clinical cancer research 31.1 (2012): 14.

Bookman, M.A., First-line chemotherapy in epithelial ovarian cancer. Clin Obstet Gynecol, 2012.55(1): p. 96-113.

Engel, J., et al. "Moderate progress for ovarian cancer in the last 20 years: prolongation of survival, but no improvement in the cure rate." European Journal of Cancer 38.18 (2002): 2435-2445.

Ricci, Francesca, Massimo Broggini, and Giovanna Damia. "Revisiting ovarian cancer preclinical models: implications for a better management of the disease." Cancer treatment reviews 39.6 (2013): 561-568.

Razak, Albiruni Ryan Abdul, et al. "Chemotherapy for malignant germ cell ovarian cancer in adult patients with early stage, advanced and recurrent disease." The Cochrane database of systematic reviews 3 (2011): CD007584.

Vang, Russell, Ie-Ming Shih, and Robert J. Kurman. "Fallopian tube precursors of ovarian low-and high-grade serous neoplasms." Histopathology 62.1 (2013): 44-58.

Salvador, Shannon, et al. "The fallopian tube: primary site of most pelvic high-grade serous carcinomas." International Journal of Gynecological Cancer 19.1 (2009): 58-64.

Gibson, Spencer B. "Autophagy in clear cell ovarian cancer, a potential marker for hypoxia and poor prognosis?." The Journal of pathology 228.4 (2012): 434-436.

Brinton, Louise A., et al. "Cancer risk after a hospital discharge diagnosis of endometriosis." American journal of obstetrics and gynecology 176.3 (1997): 572-579.

(56) References Cited

OTHER PUBLICATIONS

Brooks, John J., and James E. Wheeler. "Malignancy arising in extragonadal endometriosis. A case report and summary of the world literature." Cancer 40.6 (1977): 3065-3073.
Medicine, A.S.o.R., Endometriosis: A Guide for Patients. 2012.
Razzaghi, M.R., endometriosis, in Endometriosis—Basic Concepts and Current Research Trends, K.Chaudhury, Editor. 2012, Ingen: Ingen.
Sampson, John A. "Metastatic or embolic endometriosis, due to the menstrual dissemination of endometrial tissue into the venous circulation." The American journal of pathology 3.2 (1927): 93.
International Search Report for PCT/US2015/061393 dated Mar. 30, 2016.
Bauckman, K. Characterization of Iron Response in Gynecological Cell Lines. Graduate—Theses and Dissertations. Scholar Commons University of South Florida. May 2014, 99 pages.
Yamamoto, Sohei, et al. "Cumulative alterations of p27Kip1-related cell-cycle regulators in the development of endometriosis-associated ovarian clear cell adenocarcinoma." Histopathology 56.6 (2010): 740-749.
Treloar, Susan A., et al. "Genomewide linkage study in 1,176 affected sister pair families identifies a significant susceptibility locus for endometriosis on chromosome 10q26." The American Journal of Human Genetics 77.3 (2005): 365-376.
Bois, Frédéric Yves, and Brenda Eskenazi. "Possible risk of endometriosis for Seveso, Italy, residents: an assessment of exposure to dioxin." Environmental health perspectives 102.5 (1994): 476.
Jacques, Suzanne M., and W. Dwayne Lawrence. "Endometrial adenocarcinoma with variable-level myometrial involvement limited to adenomyosis: a clinicopathologic study of 23 cases." Gynecologic oncology 37.3 (1990): 401-407.
Kucera, E., et al. "Malignant changes in adenomyosis in patients with endometrioid adenocarcinoma." European journal of gynaecological oncology 32.2 (2011): 182-184.
Kato, Noriko, Shun-ichi Sasou, and Teiichi Motoyama. "Expression of hepatocyte nuclear factor-1beta (HNF-1beta) in clear cell tumors and endometriosis of the ovary." Modern pathology 19.1 (2006): 83.
Grechukhina, Olga, et al. "A polymorphism in a let-7 microRNA binding site of KRAS in women with endometriosis." EMBO molecular medicine 4.3 (2012): 206-217.
Stewart, Colin JR, et al. "KRAS mutations in ovarian low-grade endometrioid adenocarcinoma: association with concurrent endometriosis." Human pathology 43.8 (2012): 1177-1183.
Sripetchwandee, J., et al. "Blockade of mitochondrial calcium uniporter prevents cardiac mitochondrial dysfunction caused by iron overload." Acta Physiologica 210.2 (2014): 330-341.
Sripetchwandee, Jirapas, et al. "Mitochondrial calcium uniporter blocker effectively prevents brain mitochondrial dysfunction caused by iron overload." Life sciences 92.4-5 (2013): 298-304.
Schulz, Tim J., et al. "Induction of oxidative metabolism by mitochondrial frataxin inhibits cancer growth Otto Warburg revisited." Journal of Biological Chemistry 281.2 (2006): 977-981.
Lee, Patty J., et al. "Overexpression of heme oxygenase-1 in human pulmonary epithelial cells results in cell growth arrest and increased resistance to hyperoxia." Proceedings of the National Academy of Sciences 93.19 (1996): 10393-10398.
Kao, T. W., et al. "Associations between serum total bilirubin levels and functional dependence in the elderly." Internal medicine journal 42.11 (2012): 1199-1207.
Novotný, Ladislav, and Libor Vitek. "Inverse relationship between serum bilirubin and atherosclerosis in men: a meta-analysis of published studies." Experimental Biology and Medicine 228.5 (2003): 568-571.
Koeppen, Arnulf H. "Friedreich's ataxia: pathology, pathogenesis, and molecular genetics." Journal of the neurological sciences 303.1-2 (2011): 1-12.
Pinnix, Zandra K., et al. "Ferroportin and iron regulation in breast cancer progression and prognosis." Science translational medicine 2.43 (2010): 43ra56-43ra56.

Reid, Thomas M., Daniel I. Feig, and Lawrence A. Loeb. "Mutagenesis by metal-induced oxygen radicals." Environmental health perspectives 102.Suppl 3 (1994): 57.
Dixon, S.J. and B.R. Stockwell, The role of iron and reactive oxygen species in cell death. NatChem Biol, 2013. 10(1): p. 9-17.
Kroemer, Guido, et al. "Classification of cell death: recommendations of the Nomenclature Committee on Cell Death 2009." Cell death and differentiation 16.1 (2009): 3.
Coates, Jodi M., Joseph M. Galante, and Richard J. Bold. "Cancer therapy beyond apoptosis: autophagy and anoikis as mechanisms of cell death." Journal of Surgical Research 164.2 (2010): 301-308.
Giannoni, E., et al. "Redox regulation of anoikis: reactive oxygen species as essential mediators of cell survival." Cell death and differentiation 15.5 (2008): 867.
Guadamillas, Marta C., Ana Cerezo, and Miguel A. del Pozo. "Overcoming anoikis-pathways to anchorage-independent growth in cancer." J Cell Sci 124.19 (2011): 3189-3197.
Frisch, Steven M., and Hunter Francis. "Disruption of epithelial cell-matrix interactions induces apoptosis." The Journal of cell biology 124.4 (1994): 619-626.
Westhoff, Mike-Andrew, and Simone Fulda. "Adhesion-mediated apoptosis resistance in cancer." Drug Resistance Updates 12.4-5 (2009): 127-136.
Choi, JongYeob, et al. "The role of autophagy in human endometrium." Biology of reproduction 86.3 (2012): 70-1.
Kenific, Candia M., Andrew Thorburn, and Jayanta Debnath. "Autophagy and metastasis: another double-edged sword." Current opinion in cell biology 22.2 (2010): 241-245.
Chen, Yongqiang, and Daniel J. Klionsky. "The regulation of autophagy—unanswered questions." J Cell Sci 124.2 (2011): 161-170.
Spowart, Jaeline E., et al. "The autophagy protein LC3A correlates with hypoxia and is a prognostic marker of patient survival in clear cell ovarian cancer." The Journal of pathology 228.4 (2012): 437-447.
Wu, Wei, Peng Liu, and Jianyong Li. "Necroptosis: an emerging form of programmed cell death." Critical reviews in oncology/hematology 82.3 (2012): 249-258.
Degterev, Alexei, et al. "Identification of RIP1 kinase as a specific cellular target of necrostatins." Nature chemical biology 4.5 (2008): 313.
Louandre, Christophe, et al. "Iron-dependent cell death of hepatocellular carcinoma cells exposed to sorafenib." International journal of cancer 133.7 (2013): 1732-1742.
Iizuka, Mari, et al. "Chemical assay of iron in ovarian cysts: a new diagnostic method to evaluate endometriotic cysts." Gynecologic and obstetric investigation 46.1 (1998): 58-60.
Kuohung, Wendy, et al. "Characteristics of patients with endometriosis in the United States and the United Kingdom." Fertility and sterility 78.4 (2002): 767-772.
Kobayashi, H., et al. "Risk of developing ovarian cancer among women with ovarian endometrioma: a cohort study in Shizuoka, Japan." International Journal of Gynecological Cancer 17.1 (2007): 37-43.
Hu, Qian, et al. "Homozygous deletion of CDKN2A/2B is a hallmark of iron-induced high-grade rat mesothelioma." Laboratory investigation 90.3 (2010): 360.
Shigetomi, Hiroshi, et al. "Molecular mechanisms linking endometriosis under oxidative stress with ovarian tumorigenesis and therapeutic modalities." Cancer investigation 30.6 (2012): 473-480.
Suzuki, Shigeru, et al. "MR findings of ruptured endometrial cyst: comparison with tubo-ovarian abscess." European journal of radiology 81.11 (2012): 3631-3637.
D'Hooghe, T. M., et al. "Nonhuman primate models for translational research in endometriosis." Reproductive Sciences 16.2 (2009): 152-161.
Tirado-González, Irene, et al. "Endometriosis research: animal models for the study of a complex disease." Journal of reproductive immunology 86.2 (2010): 141-147.
Dinulescu, Daniela M., et al. "Role of K-ras and Pten in the development of mouse models of endometriosis and endometrioid ovarian cancer." Nature medicine 11.1 (2005): 63.

(56) References Cited

OTHER PUBLICATIONS

Mariani, Margherita, et al. "The selective vitamin D receptor agonist, elocalcitol, reduces endometriosis development in a mouse model by inhibiting peritoneal inflammation." Human reproduction 27.7 (2012): 2010-2019.
Cheng, Ching-wen, et al. "Activation of mutated K-ras in donor endometrial epithelium and stroma promotes lesion growth in an intact immunocompetent murine model of endometriosis." The Journal of pathology 224.2 (2011): 261-269.
Yamanaka, Akiyoshi, et al. "Primate model research for endometriosis." The Tohoku journal of experimental medicine 226.2 (2012): 95-99.
Mayr, Doris, et al. "Does endometriosis really have premalignant potential? A clonal analysis of laser-microdissected tissue." The FASEB Journal 17.6 (2003): 693-695.
Smith, D. M., et al. "Arsenic trioxide induces a beclin-1-independent autophagic pathway via modulation of SnoN/SkiL expression in ovarian carcinoma cells." Cell death and differentiation 17.12 (2010): 1867.
Tan, T. H., J. Wallis, and A. J. Levine. "Identification of the p53 protein domain involved in formation of the simian virus 40 large T-antigen-p53 protein complex." Journal of virology 59.3 (1986): 574-583.
Lilyestrom, Wayne, et al. "Crystal structure of SV40 large T-antigen bound to p53: interplay between a viral oncoprotein and a cellular tumor suppressor." Genes & development 20.17 (2006): 2373-2382.
Yang, Gong, et al. "Knockdown of p53 combined with expression of the catalytic subunit of telomerase is sufficient to immortalize primary human ovarian surface epithelial cells." Carcinogenesis 28.1 (2007): 174-182.
Dive, Caroline, et al. "Considerations for the use of plasma cytokeratin 18 as a biomarker in pancreatic cancer." British journal of cancer 102.3 (2010): 577.
Fortier, Anne-Marie, Eric Asselin, and Monique Cadrin. "Keratin 8 and 18 loss in epithelial cancer cells increases collective cell migration and cisplatin sensitivity through claudin1 up-regulation." Journal of Biological Chemistry (2013): jbc-M112.
Sivridis, Efthimios, et al. "Autophagy in endometrial carcinomas and prognostic relevance of 'stone-like' structures (SLS): what is destined for the atypical endometrial hyperplasia?." Autophagy 7.1 (2011): 74-82.
Ren, Yuefang, et al. "Decreased expression of Beclin 1 in eutopic endometrium of women with adenomyosis." Archives of gynecology and obstetrics 282.4 (2010): 401-406.
Giatromanolaki, Alexandra, et al. "High Beclin 1 expression defines a poor prognosis in endometrial adenocarcinomas." Gynecologic oncology 123.1 (2011): 147-151.
Orfanelli, T., et al. "Involvement of Autophagy in Cervical, Endometrial and Ovarian Cancer." International Journal of Cancer (2013): 1-32. Web.
Bauckman, Kyle A., et al. "Abstract 1044: Role of Autophagic Mediators in the Transition from Endometriosis to Endometriosis-Associated Ovarian Cancers." In: Proceedings of the 102nd Annual Meeting of the American Association for Cancer Research; Apr. 2-6, 2011; Orlando, FL. Philadelphia (PA): AACR; Cancer Res 2011;71(8 Suppl): Abstract nr 1044. doi:10.1158/1538-7445.AM2011-1044.
Fung, Christopher, et al. "Induction of autophagy during extracellular matrix detachment promotes cell survival." Molecular biology of the cell 19.3 (2008): 797-806.
Huang, Ju, and Daniel J. Klionsky. "Autophagy and human disease." Cell cycle 6.15 (2007): 1837-1849.
Yang, Zhifen, and Daniel J. Klionsky. "An overview of the molecular mechanism of autophagy." Autophagy in infection and immunity. Springer, Berlin, Heidelberg, 2009. 1-32.
Pelch, Katherine E., et al. "Aberrant gene expression profile in a mouse model of endometriosis mirrors that observed in women." Fertility and sterility 93.5 (2010): 1615-1627.
Rai, Priyanka, and Sisinthy Shivaji. "The role of DJ-1 in the pathogenesis of endometriosis." PLoS One 6.3 (2011): e18074.

Signorile, Pietro G., and Alfonso Baldi. "Endometriosis: new concepts in the pathogenesis." The international journal of biochemistry & cell biology 42.6 (2010): 778-780.
Rogers, Peter AW, et al. "Priorities for endometriosis research: recommendations from an international consensus workshop." Reproductive Sciences 16.4 (2009): 335-346.
Baldi, Alfonso, Mara Campioni, and Pietro G. Signorile. "Endometriosis: pathogenesis, diagnosis, therapy and association with cancer." Oncology reports 19.4 (2008): 843-846.
Bulun SE. Endometriosis. N Engl J Med Jan. 15, 2009; 360(3): 268-279.
Omwandho, Charles OA, et al. "Role of TGF-βs in normal human endometrium and endometriosis." Human reproduction 25.1 (2009): 101-109.
Nasu, Kaei, et al. "Aberrant expression of apoptosis-related molecules in endometriosis: a possible mechanism underlying the pathogenesis of endometriosis." Reproductive Sciences 18.3 (2011): 206-218.
Béliard, Aude, Agnès Noel, and Jean-Michel Foidart. "Reduction of apoptosis and proliferation in endometriosis." Fertility and sterility 82.1 (2004): 80-85.
Taniguchi, Fuminori, et al. "Apoptosis and endometriosis." Frontiers in bioscience (Elite edition) 3 (2011): 648-662.
Harada, T., et al. "Apoptosis in human endometrium and endometriosis." Human reproduction update 10.1 (2004): 29-38.
Simpson, Craig D., Kika Anyiwe, and Aaron D. Schimmer. "Anoikis resistance and tumor metastasis." Cancer letters 272.2 (2008): 177-185.
Geiger, Thomas R., and Daniel S. Peeper. "The neurotrophic receptor TrkB in anoikis resistance and metastasis: a perspective." Cancer research 65.16 (2005): 7033-7036.
Defrère, Sylvie, et al. "Insights into iron and nuclear factor-kappa B (NF-κb) involvement in chronic inflammatory processes in peritoneal endometriosis." Histology and histopathology 26.7 (2011): 1083-1092.
Ndong, Moussa, et al. "Iron deficiency down-regulates the Akt/TSC1-TSC2/mammalian Target of Rapamycin signaling pathway in rats and in COS-1 cells." Nutrition research 29.9 (2009): 640-647.
Ponce, Carlos, et al. "Nuclear factor κb pathway and interleukin-6 are affected in eutopic endometrium of women with endometriosis." Reproduction 137.4 (2009): 727-737.
Liu XM, Peyton KJ, Ensenat D, Wang H, Schafer AI, Alam J, et al. Endoplasmic reticulum stressstimulates heme oxygenase-1 gene expression in vascular smooth muscle. Role in cell survival. J BiolChem Jan. 14, 2005; 280(2): 872-877.
Kim, Hong Pyo, et al. "Heme oxygenase-1 comes back to endoplasmic reticulum." Biochemical and biophysical research communications 404.1 (2011): 1-5.
He, Y., et al. "Induction of autophagy in rat hippocampus and cultured neurons by iron." Cerebral Hemorrhage. Springer, Vienna, 2008. 29-32.
Mizushima, Noboru. "Methods for monitoring autophagy using GFP-LC3 transgenic mice." Methods in enzymology 452 (2009): 13-23.
Mizushima, Noboru, and Akiko Kuma. "Autophagosomes in GFP-LC3 transgenic mice." Autophagosome and Phagosome. Humana Press, 2008. 119-124.
Mukhopadhyay, Arunima, et al. "Hydroxychloroquine for chronic myeloid leukemia: complete cure on the horizon?." Expert review of hematology 4.4 (2011): 369-371.
Colón-Díaz, Maricarmen, et al. "HDAC1 and HDAC2 are differentially expressed in endometriosis." Reproductive sciences 19.5 (2012): 483-492.
Sivridis, Efthimios, et al. "LC3A-positive "stone-like" structures in cutaneous squamous cell carcinomas." The American Journal of Dermatopathology 33.3 (2011): 285-290.
Shimizu S, Takehara T, Hikita H, Kodama T, Tsunematsu H, Miyagi T, et al. Inhibition of autophagy potentiates the antitumor effect of the multikinase inhibitor sorafenib in hepatocellular carcinoma. Int JCancer Aug. 19, 2011.

(56) References Cited

OTHER PUBLICATIONS

Mirzoeva, Olga K., et al. "Autophagy suppression promotes apoptotic cell death in response to inhibition of the PI3K—mTOR pathway in pancreatic adenocarcinoma." Journal of molecular medicine 89.9 (2011): 877-889.

Yang, Shenghong, et al. "Pancreatic cancers require autophagy for tumor growth." Genes & development (2011).

Hirata, Tetsuya, et al. "Development of an experimental model of endometriosis using mice that ubiquitously express green fluorescent protein." Human Reproduction 20.8 (2005): 2092-2096.

Fang, Zongjuan, et al. "Intact progesterone receptors are essential to counteract the proliferative effect of estradiol in a genetically engineered mouse model of endometriosis." Fertility and sterility 82.3 (2004): 673-678.

Mizushima, Noboru, and Beth Levine. "Autophagy in mammalian development and differentiation." Nature cell biology 12.9 (2010): 823.

Daikoku, Takiko, et al. "Conditional loss of uterine Pten unfailingly and rapidly induces endometrial cancer in mice." Cancer research 68.14 (2008): 5619-5627.

Xu, Cheng-Xiong, et al. "Augmentation of NVP-BEZ235's anti-cancer activity against human lung cancer cells by blockage of autophagy." Cancer biology & therapy 12.6 (2011): 549-555.

Hou, J., et al., Targeting Mnks for cancer therapy. Oncotarget, 2012. 3(2): p. 118-31.

Fortin, C.F., et al., Translational control of human neutrophil responses by MNK1. J Leukoc Biol,2013. 94(4): p. 693-703.

Dixon, S.J., et al., Ferroptosis: an iron-dependent form of nonapoptotic cell death. Cell, 2012.149(5): p. 1060-72.

Klemmt et al., Endometrial cells from women with endometriosis have increased adhesion and proliferative capacity in response to extracellular matrix components: towards a mechanistic model for endometriosis progression, Human Reproduction vol. 22, No. 12, p. 3139-3147, 2007.

Marciano et al., Methods for Identifying Novel Integrin Ligands, Methods Enzymol. 426:223-237, 2007.

Office Action issued by the European Patent Office for application 15861702.7, dated Nov. 4, 2019.

* cited by examiner

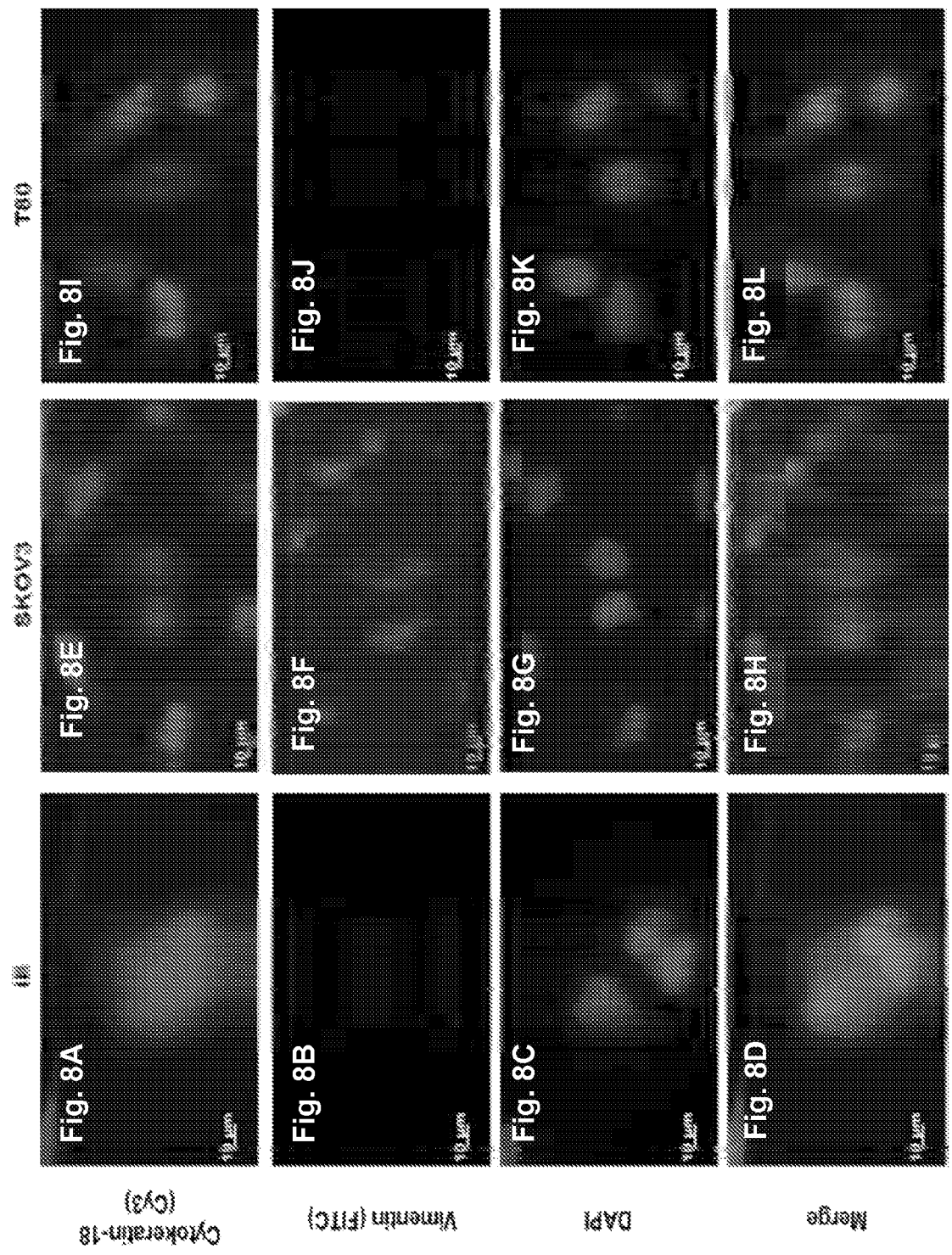

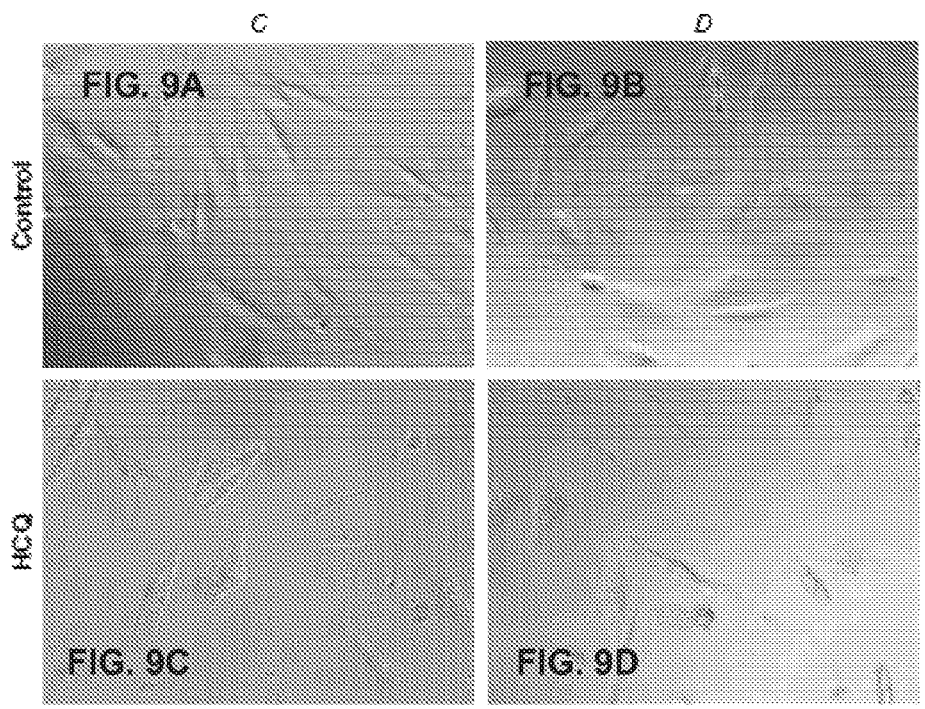
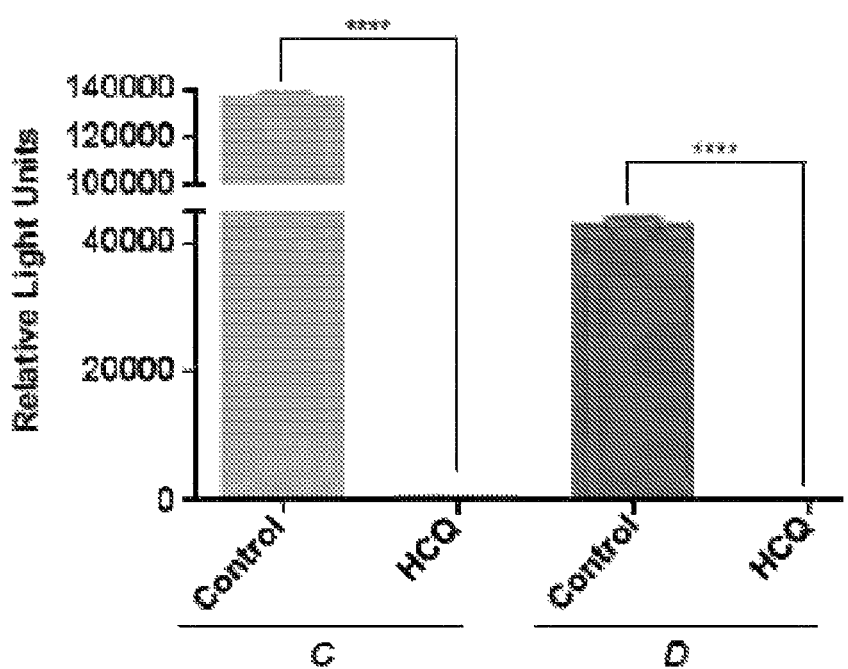
FIG. 10

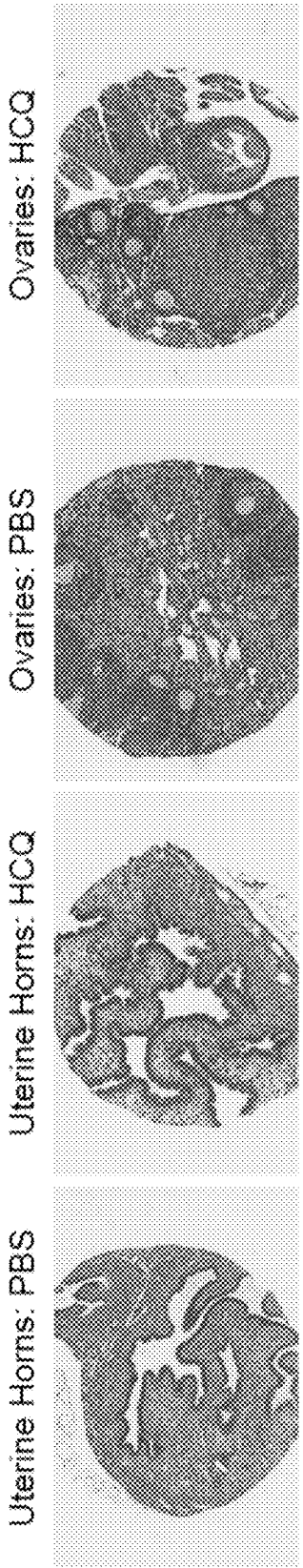

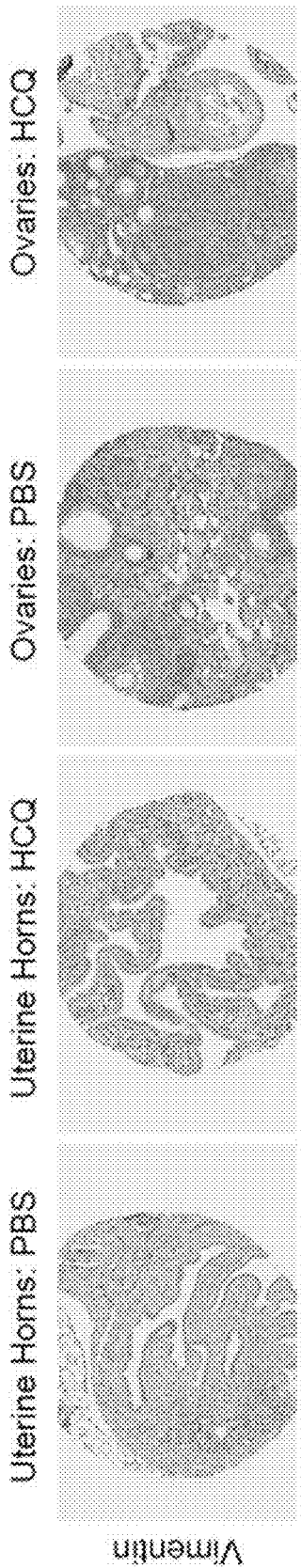

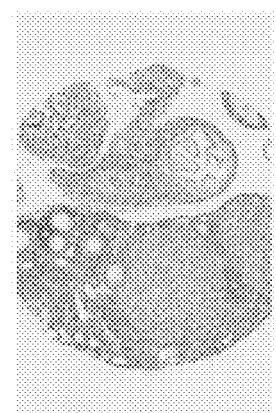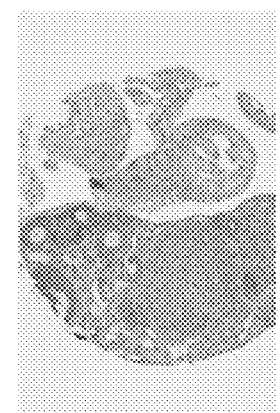
FIG. 19E  FIG. 19K  FIG. 19Q  FIG. 19W
FIG. 19F  FIG. 19L  FIG. 19R  FIG. 19X

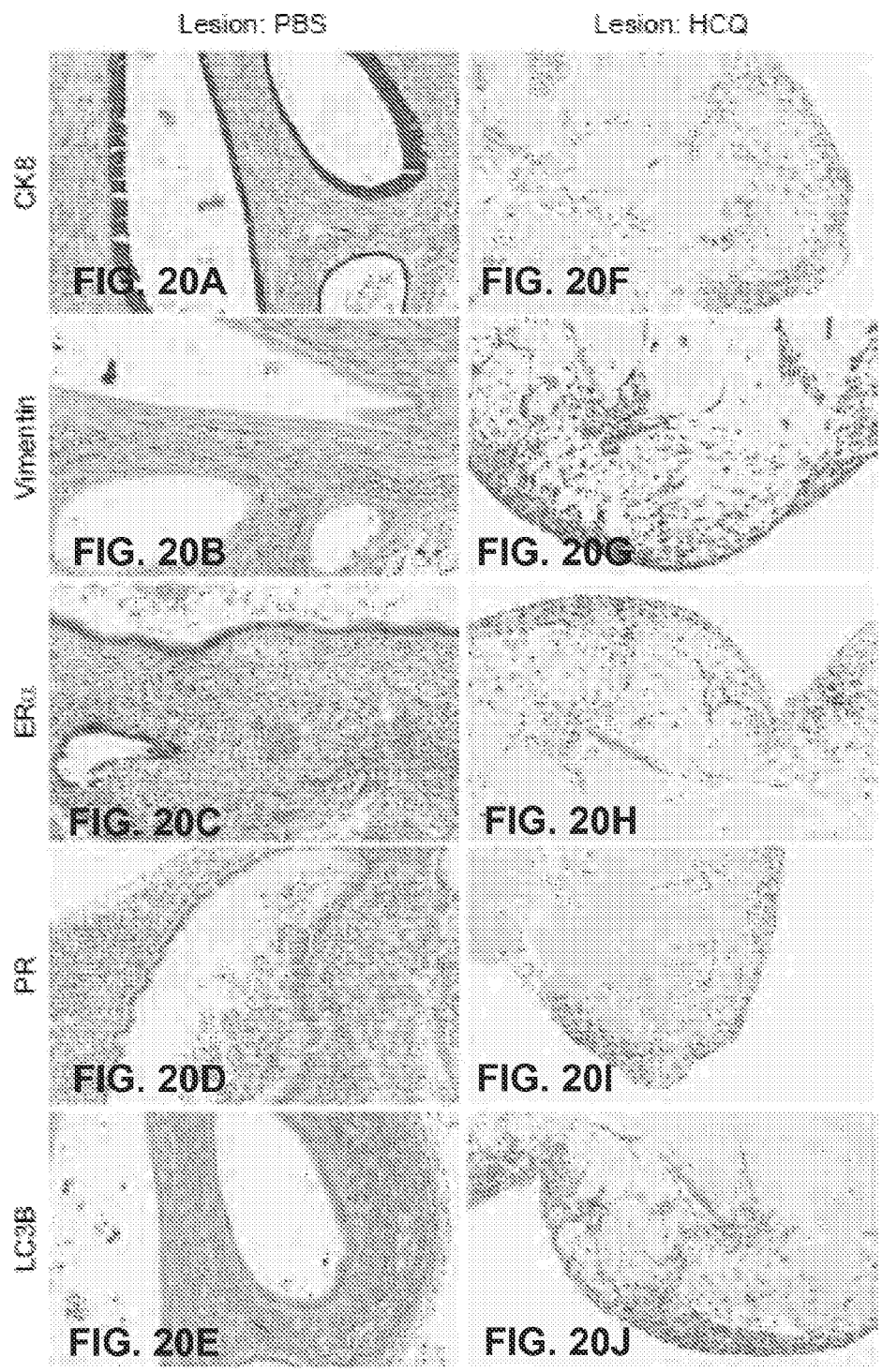

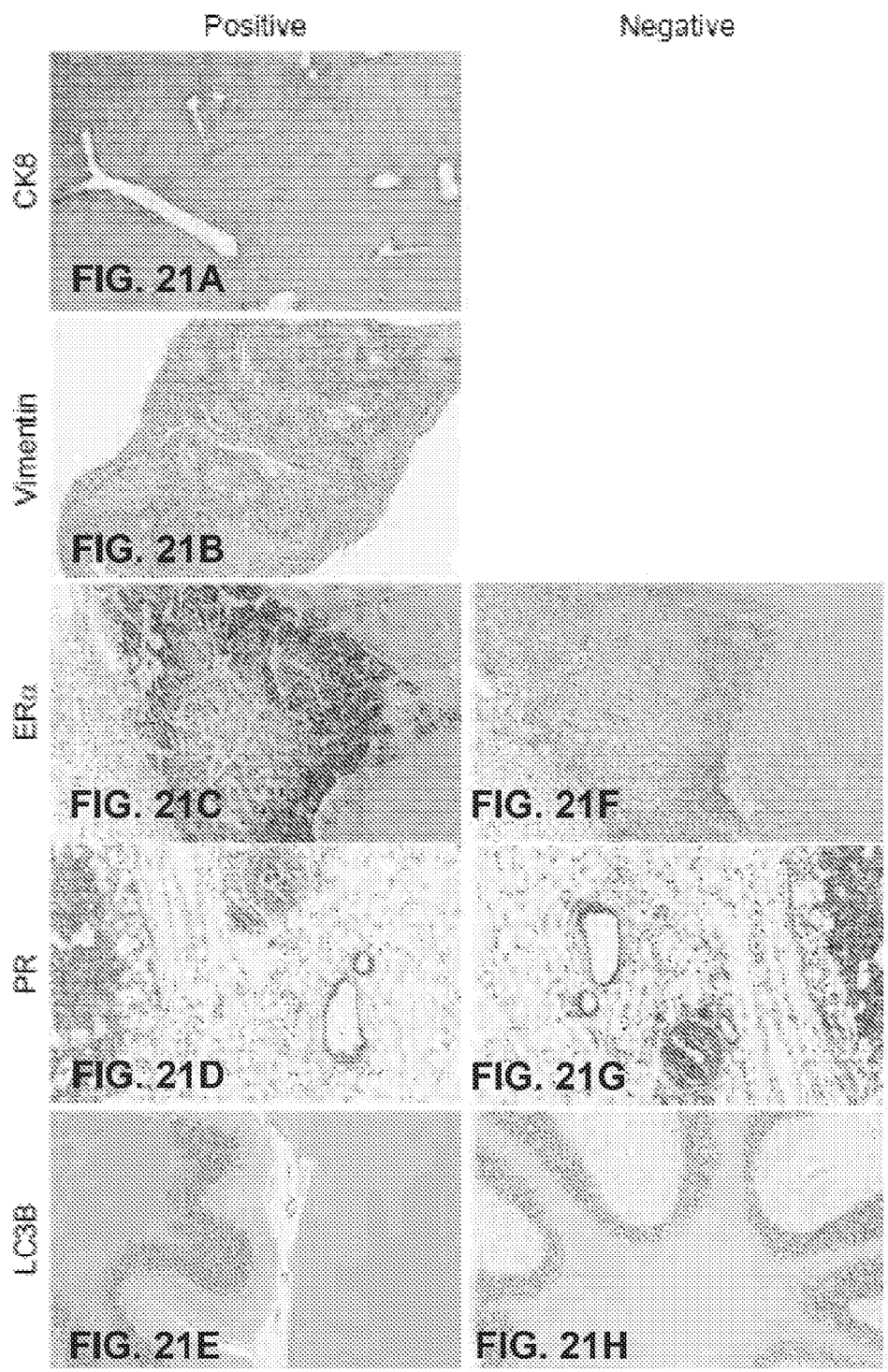

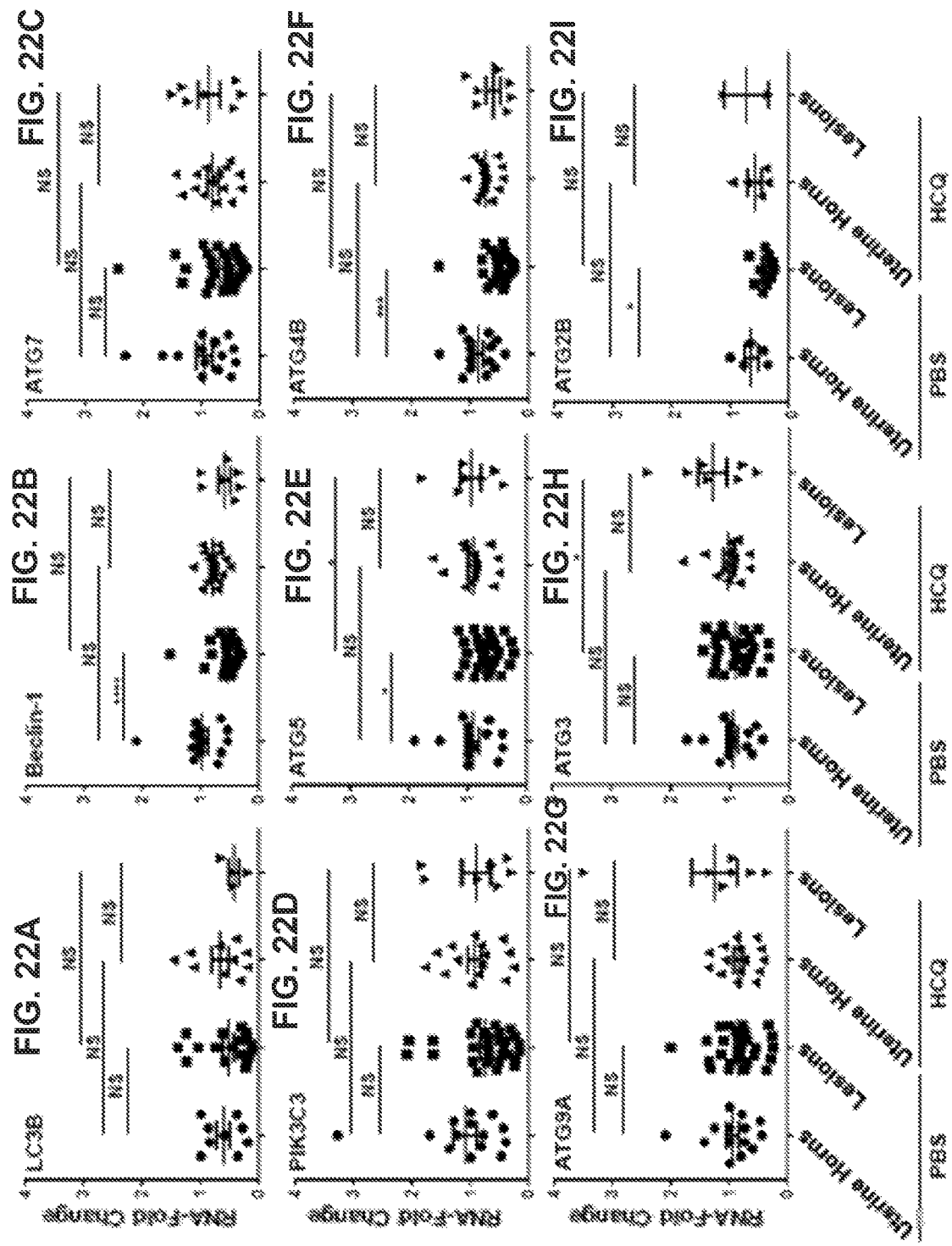

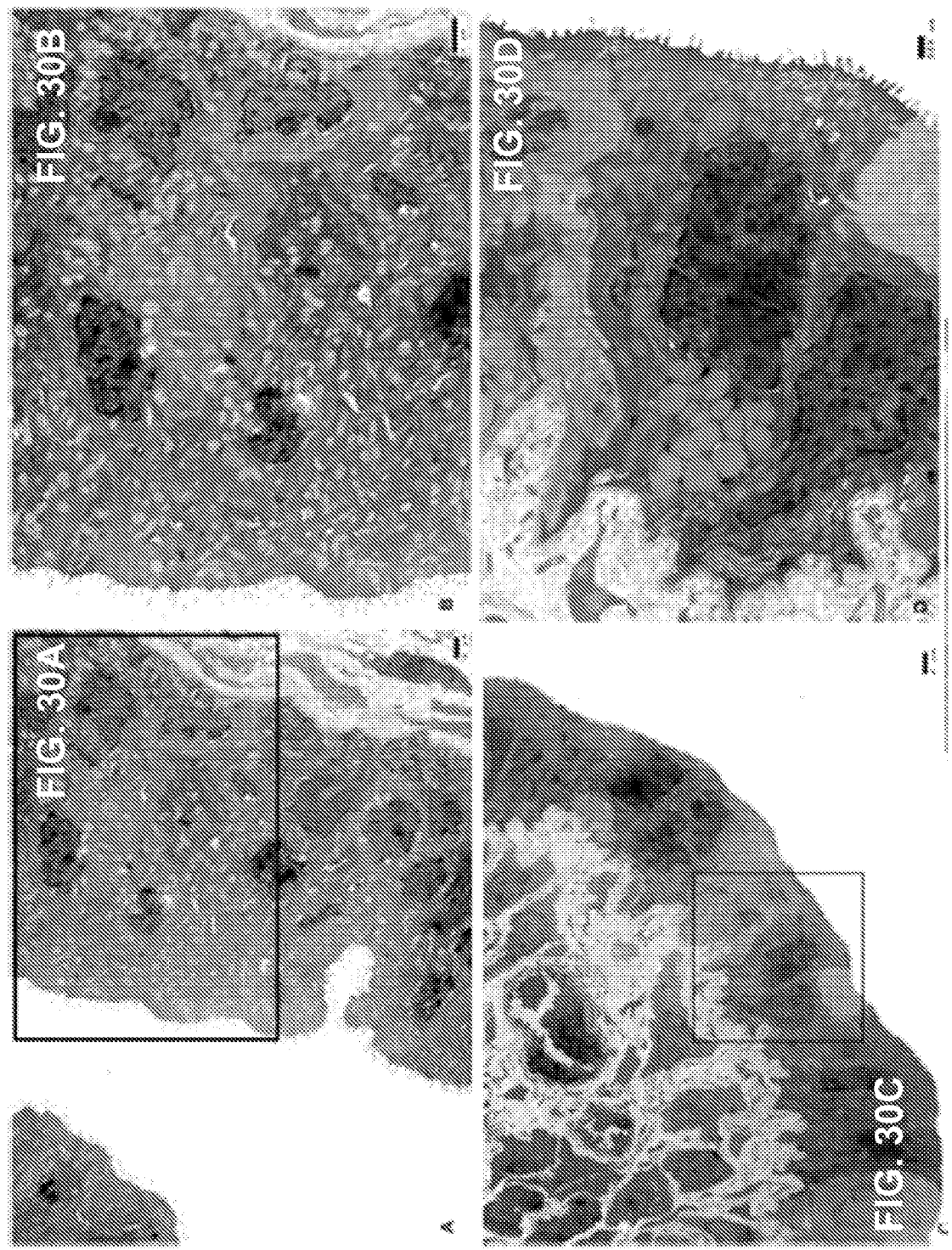

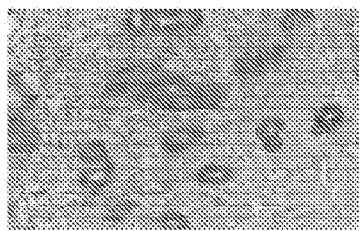
Proliferative: Controls
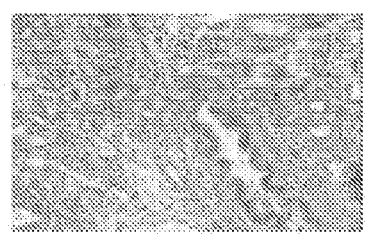
Secretory: Controls
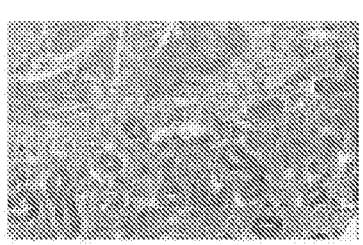
Proliferative: Patients
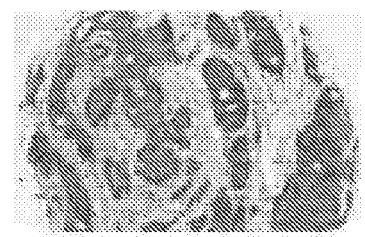
Antibody: Positive control
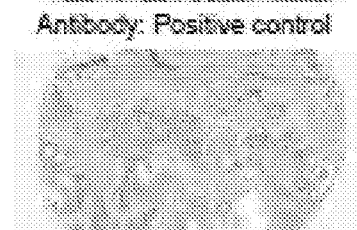
Antibody: Negative control
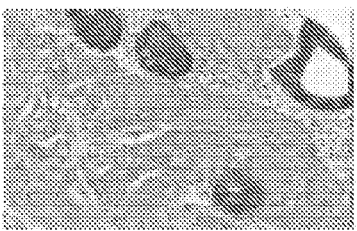
Fallopian tube
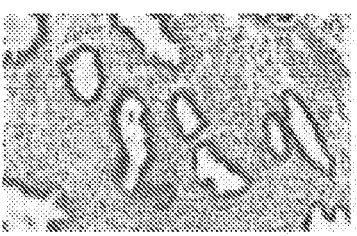
Ovary
Peritoneal
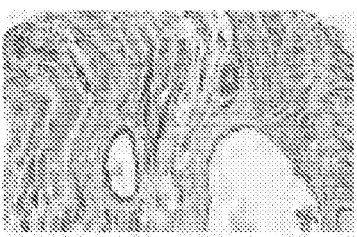
Gastrointestinal
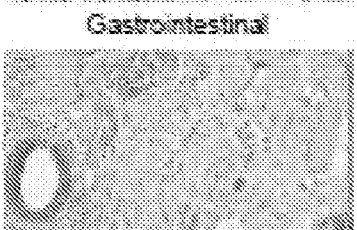
Skin
FIG. 31A
FIG. 31B
FIG. 31C
FIG. 31D
FIG. 31E
FIG. 31F
FIG. 31G
FIG. 31H
FIG. 31I
FIG. 31J

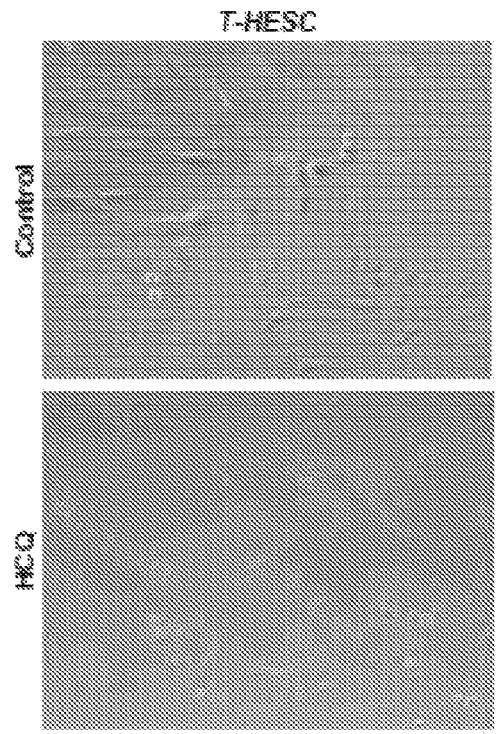
FIG. 34A
FIG. 34B
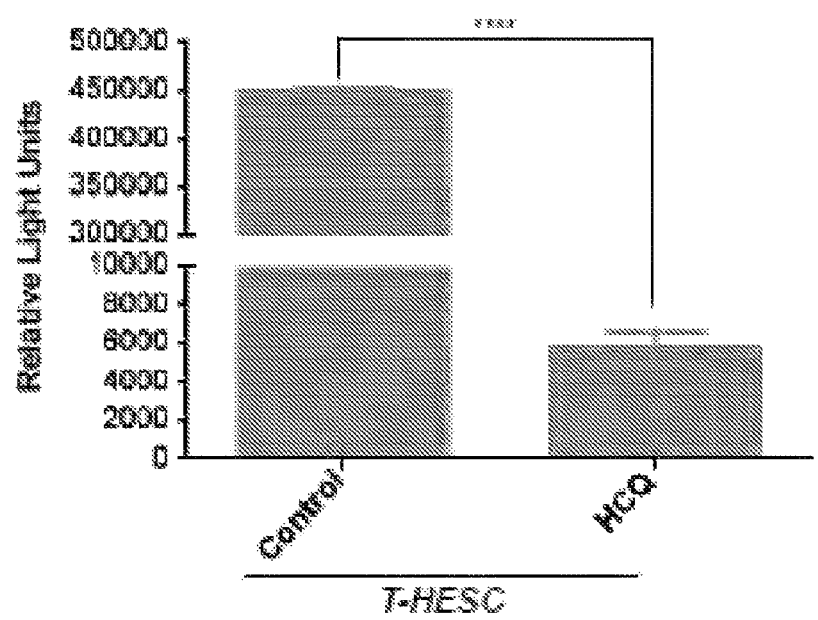
FIG. 35

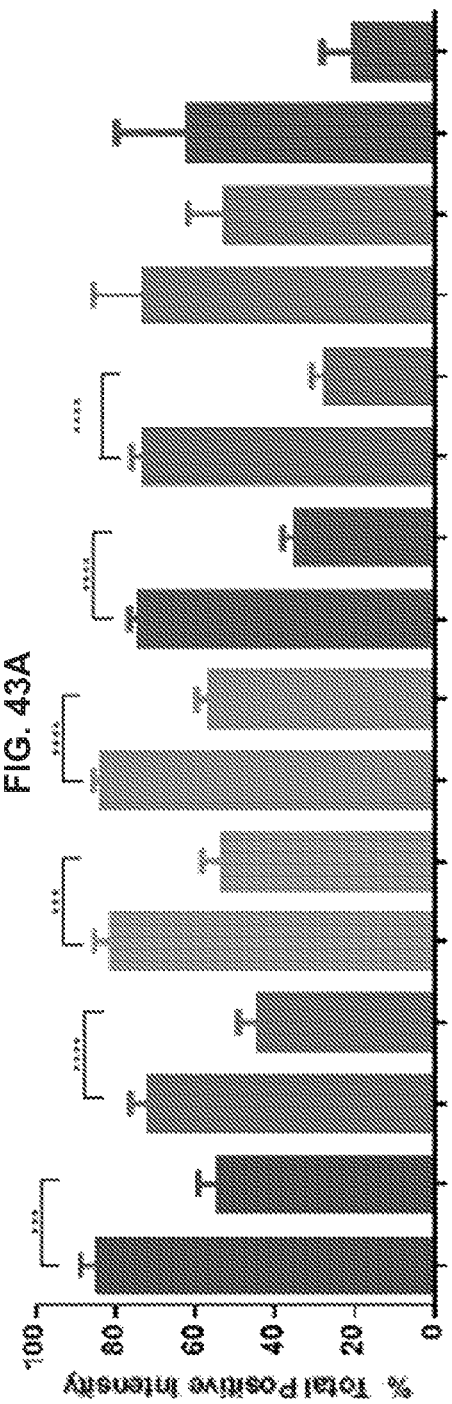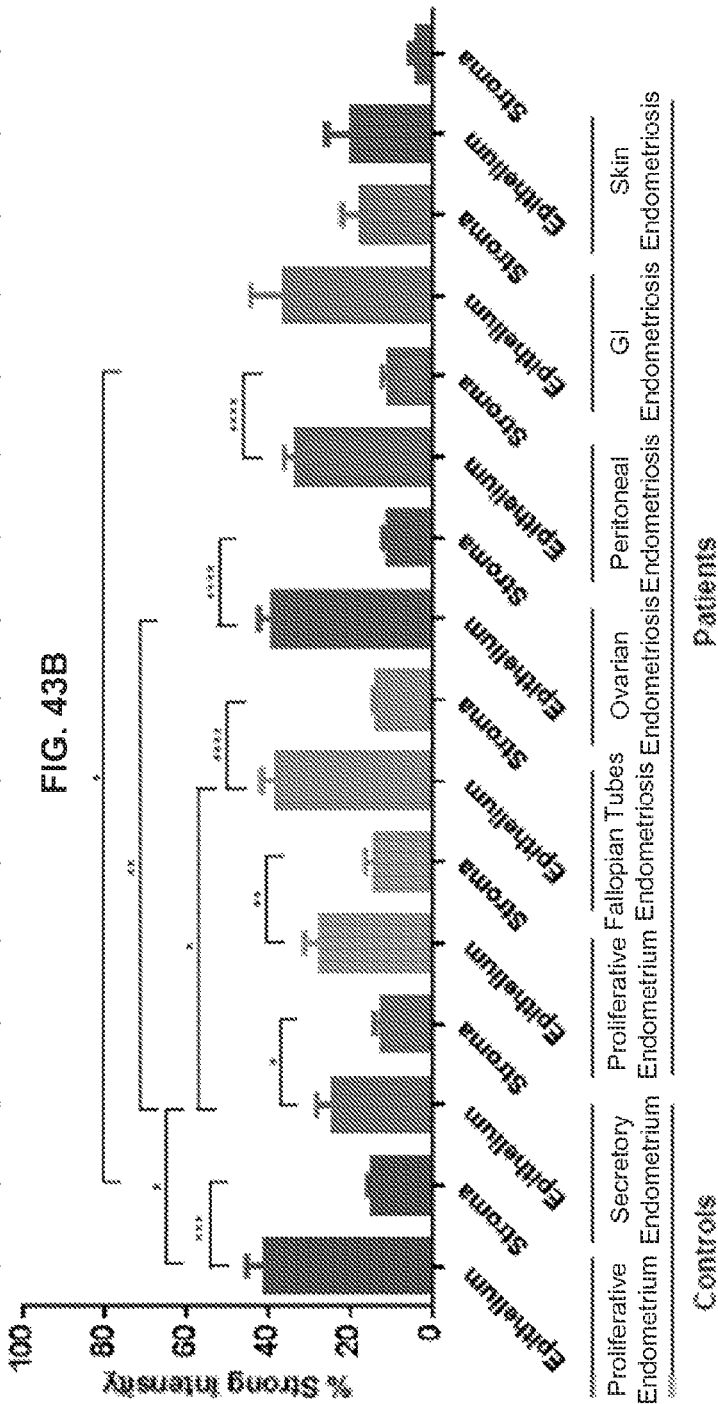
FIG. 43A
FIG. 43B

| | Conducive Recipient | | | |
|---|---|---|---|---|
| | RT²-PCR | | Real-Time PCR Validation | |
| Gene | Fold Change | P value | Fold Change | P value |
| IGF1 | 2.95 | p=0.044 | 2.623 | p=0.1457 |
| BNIP3 | -4.62 | p=0.015 | -4.593 | p=0.0621 |
| ATG9B | -4.53 | p=0.015 | -3.986 | p=0.0113 |
| LC3A | -2.03 | p=0.007 | -1.749 | p=0.0306 |
| LC3B | -1.94 | p=0.0012 | -2.182 | p=0.0040 |
| PRKAA1 | -1.92 | p=0.023 | -2.208 | p=0.0065 |
| ATG4C | -1.85 | p=0.031 | -2.602 | p=0.0167 |
| FAS | -1.85 | p=0.003 | -2.692 | p=0.0034 |
| IRGM1 | -1.83 | p=0.025 | -1.360 | p=0.1680 |
| GABARAPL1 | -1.56 | p=0.045 | -2.011 | p=0.0360 |
| PTEN | -1.51 | p=0.048 | -1.448 | p=0.0295 |
| EIF2AK3 | -1.48 | p=0.043 | -1.879 | p=0.0068 |
| SQSTM1 | -1.38 | p=0.054 | -2.634 | p=0.0008 |

FIG. 48

| Gene | Fold Change | P value |
|---|---|---|
| Beclin-1 | 2.20 | 0.0330 |
| p62 | 1.00 | NS |
| LC3B-I | 4.00 | 0.0185 |
| LC3B-II | 6.76 | 0.0364 |
| LC3A-I | 1.29 | NS |
| LC3A-II | 1.97 | 0.0135 |
| GABARAPL1 | 1.95 | 0.0334 |
| AMPKα | 0.86 | NS |

FIG. 49

COMPOSITIONS AND METHODS FOR TREATING ENDOMETRIOSIS

CROSS-REFERENCE TO RELATED APPLICATIONS

This application is the 35 U.S.C. § 371 national stage application of PCT Application No. PCT/US2015/061393, filed Nov. 18, 2015, where the PCT claims the benefit of U.S. Provisional Application Ser. No. 62/081,464 filed on Nov. 18, 2014, having the title "Compositions and Methods for Treating Endometriosis," both of which are herein incorporated by reference in their entireties.

STATEMENT REGARDING FEDERALLY SPONSORED RESEARCH OR DEVELOPMENT

This invention was made with government support under Grant Number 1R21HD075225-01A1, awarded by the National Institutes of Health. The government has certain rights in the invention.

SEQUENCE LISTING

This application contains a sequence listing filed in electronic form as an ASCII.txt file entitled Third_Revised_292103-2530_Sequence_ST25, created on Nov. 19, 2018, and having a size of 1.747036 MB. The content of the sequence listing is incorporated herein in its entirety.

BACKGROUND

Endometriosis is a gynecological disease that afflicts women of child-bearing age. Although itself benign, it is a very painful, chronic, and inflammatory condition characterized by endometriotic lesions at ectopic sites and ovarian cysts leading to infertility and an increased risk of specific subtypes of ovarian cancer. Characteristic symptoms of endometriosis include chronic pelvic pain, pain during intercourse (dyspareunia), painful periods (dysmenorrhea), and infertility.

Endometriotic lesions are characterized by functional endometrial-like tissue (epithelial glands and stroma) outside of the uterus, particularly in the peritoneal area, affecting reproductive organs, the bladder and the intestinal tract. Endometriosis is the third leading cause of gynecologic hospitalization in the United States. Hospital surveys estimate that the prevalence of endometriosis among all pre-menopausal women is up to 10%, which equates to about 180 million affected women and adolescents worldwide.

Due to the severe pain, multiple surgeries, including hysterectomies, and the negative impact on the reproductive capacity, endometriosis substantially and negatively affects the quality of life of affected adolescents and women. The definitive causes of endometriosis are unclear. However, eutopic endometrium deposited into the peritoneal cavity via retrograde menstruation, is considered the source of cells that form endometriotic lesions. Development of therapeutic and strategies to diagnose, treat, mitigate, or eliminate the lesions and to relieve the pain, without interfering with the fertility potential, and prevention of further progression of this disease are greatly needed for these patients.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 8A-8L demonstrate the confirmation of absence of vimentin and presence of cytokeratin-18 (Cy3) (epithelial marker) was performed via immunofluorescence. T80 cells served as a positive control for Cy3 and SKOV3 was used a positive control for vimentin. FIGS. 8A-8D show life extended endometrial cells. FIGS. 8E-8H show SKOV3 cells. FIGS. 8I-8L show T80 cells. FIGS. 8A, 8E, and 8I show expression cytokeratin-18 (Cy3), FIGS. 8B, 8F, and 8J show expression of Vimentin (FITC). FIGS. 8C, 8G, and 8K show DAPI staining. FIGS. 8D, 8H, and 8L show the merged image of Cy3, FITC, and DAPI staining.

FIGS. 9A-9D show images of life-extended human endometriotic cells treated (FIGS. 9C-9D) with hydroxychloroquine (HCQ) or untreated (FIGS. 9A-9B). Life-extended human endometriotic cells were isolated from two different leision types and thus treated separately (C and D).

FIG. 10 shows a graph demonstrating results from a cell viability assay in life-extended human endometriotic cells treated with HCQ or control. Life-extended human endometriotic cells were isolated from two different leision types and thus treated separately (C and D).

FIGS. 17A-17B demonstrate the flow cytometry results using canonical macrophage markers CD11 b and F4/80 in normal (FIG. 17A) and recipient mice (FIG. 17B). FIG. 17C shows a graph demonstrating macrophage number as a percent of total cells examined in control and recipient mice.

FIGS. 18A-18B demonstrate the flow cytometry results using canonical macrophage markers CD11 b and F4/80 in normal (FIG. 18A) and recipient mice (FIG. 187B). FIG. 18C shows a graph demonstrating macrophage number as a percent of total cells examined in control and recipient mice.

FIGS. 19A-19X show images of tissue sections of uterine horns of control (PBS) treated (FIGS. 19A-19F) and HCQ treated (FIGS. 19G-19L) mice and ovaries of control (PBS) treated (FIGS. 19M-19R) and HCQ treated (FIGS. 19S-19X) mice, where the tissue sections were subjected to various stains or immunohistochemical analysis.

FIGS. 20A-20J show images of tissue sections of lesions of control (PBS) treated (FIGS. 20A-20E) and HCQ treated (FIGS. 20F-20J) mice, where the tissue sections were subjected to various stains or immunohistochemical analysis.

FIGS. 21A-21H shows representative images of positive (FIGS. 21A-21E) and negative (FIGS. 21F-21H) staining controls used for the antibodies used in FIGS. 20A-20J.

FIGS. 22A-22J show graphs demonstrating mRNA abundance of 10 molecule involved in the autophagic pathway (as expressed as RNA fold change) in the uterine horns and lesions of control (PBS) and HCQ treated mice. ● indicates individual reps of uterine horns of mice treated with PBS, ■ indicated individual reps of lesions of mice treated with PBS, ▲ indicates individual reps of uterine horns of mice treated with HCQ, and ▼ indicates individual reps of lesions of mice treated with HCQ.

FIGS. 31A-31J show representative immunohistochemical images for endometrium (controls and patients) and lesions (fallopian tubes, ovaries, peritoneal, gastrointestinal, and skin).

FIGS. 34A-34B show images of control and HCQ treated T-HESC human endometrial stromal cells derived from a myoma.

FIG. 35 shows a graph demonstrating survivability of control and HCQ treated T-HESC cells.

FIGS. 43A-43B show graphs demonstrating the total positive intensity (FIG. 43A) and % of cells with a strong intensity (FIG. 43B) using the H-score system of LC3B protein expression (as determined by immunohistochemistry) in the indicated samples of controls and patients.

FIG. 48 shows a table demonstrating $RT^2$ PCR and Real-Time PCR validation results for the various genes indicated in control and recipient mice.

FIG. 49 shows a table demonstrating fold change and P-values for various genes indicated in uterine horns from endometriosis-induced mice relative to those from control mice.

DETAILED DESCRIPTION

Figure 1A:
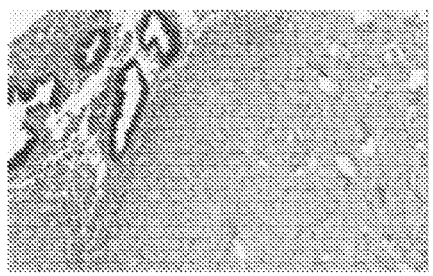
FIGS. 1A-1E demonstrates results from an immunohistochemical assay for LC3 in ovary tissue from a subject having ovarian endometriosis (FIG. 1A), fallopian tissue from a subject having fallopian endometriosis (FIG. 1B), lesion tissue from a subject having proliferative endometriosis (FIG. 1C), control proliferative endometrium control tissue (FIG. 1D), secretory endometrium control tissue (FIG. 1E). LC3 expression was assessed by comparing the relative expression in endometriotic tissue (FIGS. 1A-1B) to proliferative endometrium from patients (FIG. 1C) and controls (FIG. 1D).
Figure 1B:
Figure 1C:
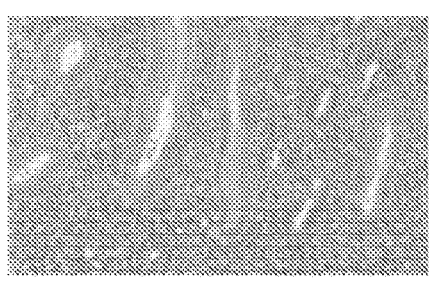
Figure 1D:
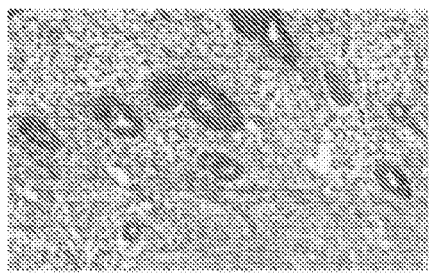
Figure 1E:
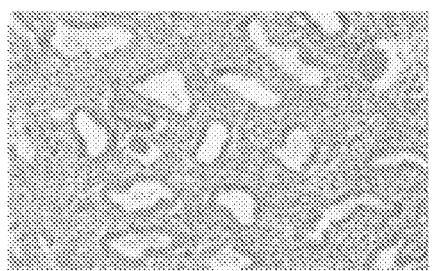

Before the present disclosure is described in greater detail, it is to be understood that this disclosure is not limited to particular embodiments described, and as such can, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges can independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "endometriotic cell" refers to a pathologic endometrial cell that can grow and survive outside the endometrium as part of an endometriotic lesion.

As used herein, "endometriotic lesion" refers to a collection or population of endometriotic cells existing in a subject or directly removed from a subject.

As used herein, "endometriosis" refers to a disease or condition that is characterized by aberrant ectopic (outside the uterus) growth and survival of endometrial cells that have transformed from normal endometrial cells to pathologic endometrial cells.

As used herein, "autophagic" refers to relating to or characterizing autophagy.

As used here, "autophagy" refers to the catabolic cell mechanism that involves cell degradation of unnecessary or dysfunctional cellular components through the actions of lysosomes.

As used herein, "immortalized cell(s)" refers to a cell or population of cells that have evaded normal cellular senescence and can proliferate indefinitely due to a biological difference, such as a DNA mutation or expression of an exogenous protein, whose expression or presence, results in an increase in the propagation capabilities compared to an average cell found in the same source as the immortalized cell(s). As long as cell culture conditions are maintained properly, immortalized cells can be propagated in cell culture indefinitely (unlimited number of passages).

As used herein, "life-extended cell(s)" refers to a cell or population of cells that can be cultured for at least between about 3 and about 20 passages longer than a non-life extended or normal cell(s) found in the same source. The ability to proliferate for about 3 to about 20 passages longer can be the result in a biological difference, such as a DNA mutation or expression of an exogenous protein, between the life-extended endometriotic cell and a normal endometriotic cell.

As used herein with reference to the relationship between DNA, cDNA, cRNA, RNA, and other nucelotides and polynucleotides and protein/peptides, the term "corresponding to" refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "life-extended endometriotic cell(s)" refers to an endometriotic cell that has acquired a biological difference, such as a DNA mutation or expression of an exogenous protein, whose expression or presence, results in an increase in the propagation capabilities of the endometriotic cell(s) compared to non-life extended or normal endometriotic cells. Life-extended endometriotic cell(s) can have an ability to proliferate in culture for about 3 to about 20 passages longer as compared to non-life extended or normal endometriotic cells.

As used herein, "personalized population of cells" refers to a population of cells containing in vitro progeny of a cell derived from a endometriotic lesion from a subject in need of treatment, where the population of cells is suitable for use to determine that particular subject's endometriotic lesion characteristics and to test the efficacy of treatments directly on the endometriotic lesion cells.

As used herein, "autophagic inhibitor" refers to a compound, molecules (e.g., DNA, RNA proteins (e.g., antibodies), or other substance that interacts with a transcript, protein, or other molecule that is involved in the autophagy pathway, such that autophagy is reduced as compared to a control.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this can be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

As used herein, "isolated" means separated from constituents, cellular and otherwise, with which the polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "specific binding," "specifically bound," and the like, refer to binding that occurs between such paired species as nucleotide/nucleotide, enzyme/substrate, receptor/agonist, antibody/antigen, and lectin/carbohydrate that can be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "separated" refers to the state of being physically divided from the original source or population such that the separated compound, agent, particle, or molecule can no longer be considered part of the original source or population.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "peptide" refers to two or more amino acids where the alpha carboxyl group of one amino acid is bound to the alpha amino group of another amino acid. Strings of 10 or more amino acids are also referred to herein as "polypeptides" or "proteins".

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" refers to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic RNA molecule including but not limited to tRNA, siRNA, piRNA, miRNA, and shRNA.

As used herein, "deoxyribonucleic acid (DNA)" and "ribonucleic acid (RNA)" generally refer to any polyribonucleotide or polydeoxribonucleotide, which can be unmodified RNA or DNA or modified RNA or DNA. RNA can be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), microRNA (miRNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "microRNA" refers to a small non-coding RNA molecule containing about 21 to about 23 nucleotides found in organisms, which functions in transcriptional and post-transcriptional regulation of transcription and translation of RNA.

As used herein, "purified" is used in reference to a nucleic acid sequence, peptide, or polypeptide or other compound described herein that has increased purity relative to the natural environment.

As used herein, "about," "approximately," and the like, when used in connection with a numerical variable, generally refers to the value of the variable and to all values of the variable that are within the experimental error (e.g., within the 95% confidence interval for the mean) or within .+−.10% of the indicated value, whichever is greater.

As used herein, "control" is an alternative subject or sample used in an experiment for comparison purposes and included to minimize or distinguish the effect of variables other than an independent variable. A "control" can be a positive control, a negative control, or an assay or reaction control (an internal control to an assay or reaction included to confirm that the assay was functional). In some instances, the positive or negative control can also be the assay or reaction control.

As used herein, "dosage form" or "unit dosage form" refers to a pharmaceutical formulation that is administered to a subject in need of treatment and generally can be in the form of tablets, capsules, sachets containing powder or granules, liquid solutions or suspensions, patches, and the like.

As used herein, "effective amount" can refer to the amount of a compound or molecule that will elicit the biological or medical response of a tissue, system, animal, or human that is being sought by the researcher, veterinarian, medical doctor or other clinician. The effective amount will vary depending on the compound or molecule, the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated. "Effective amount" can refer to the amount of an autophagic inhibitor, such as HCQ, that can treat, mitigate, or prevent endometriosis, an endometriotic lesion, or other symptom thereof. The "effective amount" can refer to the amount of an autophagic inhibitor, such as HCQ, that can prevent, mitigate, and/or reduce the formation of new endometriotic lesions and/or prevent progression or stage change of endometriosis. The terms "sufficient" and "effective", as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier, diluent, binders, lubricants, glidant, preservative, flavoring agent, coloring agent, and excipient" refers to a carrier, diluent, binder, lubricant, glidant, preservative, flavoring agent, coloring agent, or excipient that is useful in preparing a pharmaceutical formulation that is generally safe, non-toxic, and is neither biologically or otherwise undesirable, and includes a carrier or excipient that is acceptable for veterinary use as well as human pharmaceutical use.

As used herein, "pharmaceutically acceptable salt" refers to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or an active derivative thereof, such as a metabolite, as compared to the host response in a normal or control patient.

As used herein, "therapeutic" refers to curing or treating a symptom of a disease or condition.

The term "treating", as used herein, can include inhibiting and/or resolving the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain. "Treating" can refer to reducing a symptom of endometriosis, such as reducing the size of a lesion, reducing the recurrence of endometriotic lesions, preventing the occurrence of new lesions, and/or preventing or delaying the progression of endometriosis to a different stage.

The term "preventing", as used herein includes preventing a disease, disorder or condition from occurring in a subject, which can be predisposed to the disease, disorder and/or condition but has not yet been diagnosed as having it. As used herein, "preventative" can refer to hindering or stopping a disease or condition before it occurs or while the disease or condition is still in the sub-clinical phase. "Preventing" can refer to delaying or stopping the recurrance of endometriotic lesions; stopping, mitigating, and/or delaying the occurance of new endometriotic lesions; stopping, mitigating, and/or delaying the progression of endometriosis in an individual.

As used herein, "mitigate" can refer to reducing a particular characteristic, symptom, or other biological or physiological parameter associated with a disease or disorder, such as endometriosis.

As used herein, "separated" refers to the state of being physically divided from the original source or population such that the separated compound, agent, particle, chemical compound, or molecule can no longer be considered part of the original source or population.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "active derivative" and the like refer to a derivative of an autophagic inhibitor, such as HCQ, that retains an ability to treat/mitigate plasma cell proliferation and/or secondary complications associated with endometriosis. Assays for testing the ability of an active derivative to perform in this fashion are known to those of ordinary skill in the art.

As used herein, "metabolite" refers to substances that result from metabolism of a compound, such as an active agent of a pharmaceutical formulation, such as HCQ.

As used herein, "active metabolite" refers to a metabolite that induces a pharmaceutical or clinical effect, such as treating or preventing endometriosis or a symptom thereof, in a subject.

As used herein, "primary metabolite" refers to a metabolite that is directly involved in growth, development, and/or reproduction of a cell or organism.

As used herein, "secondary metabolite" refers to a metabolite that is not directly involved in growth, development, and/or reproduction of a cell or organism.

As used herein, "capture molecule" refers to a molecule that is configured to specifically bind one or more biomarker molecules of interest. A capture molecule can be a polynucleotide, antibody, antigen, apatmer, affibody, polypeptides, peptides, or combinations thereof that specifically bind one or more biomarkers of interest. For example, the capture molecule can be configured to specifically bind a polynucleotide or polypeptide corresponding to ATG-5, ATG-7, ATG-9, DJ-1(Park7), hVps34, beclin-1, p-ULK1, ATG1(ULK1), p-mTOR, mTOR, integrin, Src, FAK, ILK, rkB, AKT, LC3A, LC3 B, TSC1, TSC2, HO-1, PTEN, ARID1A, PIK3CA, K-RAS, BCL-2, ATG16, ATG12, ATG10, ATG3, LC3-1, ATG4, EVI1, RON, EGFR, SnoN, SkiL TGFβRII, p53, Smad2/3, p-ERK, ERK, PARP, cleaved PARP, p62, ferritin, E-cadherin, N-cadherin, vimentin cytokeratin-18 and/or combinations thereof. Representative polypeptide and polynucleotide sequences for the aforementioned biomarkers and any other biomarkers described herein can be 100% identical, 90-100% identical, 80-90% identical, 70-80% identical, 60-70% identical, or 50-100% identical to any one of SEQ ID NOs: 1-314 or 100% identical, 90-100% identical, 80-90% identical, 70-80% identical, 60-70% identical, or 50-100% identical to a sequence corresponding to any one of SEQ ID NOs: 1-314.

As used herein "essentially discrete" as applied to features of an array refers to the situation where 90% or more of the features of an array are not in direct contact with other features of the same array.

As used herein "attached" as applied to capture molecules of an array refers to a covalent interaction or bond between a molecule on the surface of the support and the capture molecule so as to immobilize the capture molecule on the surface of the support.

As used herein "operatively-linked" as applied to capture molecules of an array refers to a non-covalent interaction between the surface of the support and the capture molecule so as to immobilize the capture molecule on the surface of the support. Such non-covalent interactions include by are not limited to, entrapment by the surface substrate, ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used herein, "biomarker" can refer to any measurable molecule, including but not limited to polynucleotides and polypeptides, or compound in a subject whose presences, absolute amount, or relative amount, is indicative of some disease, condition, syndrome, disorder, or symptom thereof, or state thereof, such as endometriosis.

As used herein, "body fluid" refers to any liquid or liquid-like substance that originates in the body of a living organism. "Body fluid" includes, but is not limited to, whole blood, serum, buffy coat of blood or other blood fraction that contains substantially only the white blood cells and platelets, plasma, cerebral spinal fluid, urine, lymph, bile and saliva.

As used herein, "affibody" refers to an engineered protein that is an antibody mimetic and can specifically bind a target molecule, and is based on a three-helix bundle domain, where each of the three helixes contains a polypeptide having about 58 amino acids.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide can differ in amino acid sequence by one or more modifications (e.g., substitutions, additions, and/or deletions). A substituted or inserted amino acid residue can or cannot be one encoded by the genetic code. A variant of a polypeptide can be naturally occurring such as an allelic variant, or it can be a variant that is not known to occur naturally.

As used herein, "wild-type" refers to the typical form of an organism, variety, strain, gene, protein, or characteristic as it occurs in nature, as distinguished from mutant forms that can result from selective breeding or transformation with a transgene.

As used herein, "diagnosis" refers to the identification or determination of the nature and circumstances of a disease, disorder, condition, syndrome, or symptom thereof in a subject.

As used herein, "prognose," refers to determining a prognosis for a disease, disorder, condition, syndrome, or symptom thereof.

As used herein, "prognosis" refers to a prediction or forecast of a chance of recovery, complete or partial, from a disease, disorder, condition, syndrome, or symptom thereof.

As used herein, "personalized population of cells" or "personalized cell" refer to an autologous population of cells or cells are an in vitro population of cells or cell that can be used to diagnose and/or prognose an individual and/or test the individual's response to a treatment.

As used herein, "emollients" refers to an externally applied agent that softens or soothes skin and are generally known in the art and listed in compendia, such as the "Handbook of Pharmaceutical Excipients", 4$^{th}$ Ed., Pharmaceutical Press, 2003.

As used herein, "surfactants" refers to surface-active agents that lower surface tension and thereby increase the emulsifying, foaming, dispersing, spreading and wetting properties of a product.

As used herein, "emulsifiers" refers to surface active substances which promote the suspension of one liquid in another and promote the formation of a stable mixture, or emulsion, of oil and water.

As used herein, "oil" refers to a composition containing at least about 95% wt of a lipophilic substance. Examples of lipophilic substances include but are not limited to naturally occurring and synthetic oils, fats, fatty acids, lecithins, triglycerides and combinations thereof.

As used herein, "emulsion" is a composition containing a mixture of non-miscible components homogenously blended together. The non-miscible components can include a lipophilic component and an aqueous component. "Emulsion" can also refer to a preparation of one liquid distributed in small globules throughout the body of a second liquid. The first liquid is the discontinuous phase and the second liquid is the continuous phase. When oil is first liquid and water or an aqueous solution is the second liquid, it is referred to herein as an "oil in water emulsion". When water or an aqueous solution is the first liquid and oil or oleagionous substance is the second liquid, it is referred to herein as "water-in-oil" emulsion". Either or both of the oil phase and aqueous phase can contain one or more surfactants, emulsifiers, emulsion stabilizers, buffers, and other excipients. Some emulsions can be gels or otherwise include a gel component.

As used herein, "lotion" refers to a low- to medium-viscosity liquid formulation. "Lotions" can contain finely powdered substances that are in soluble in the dispersion medium through the use of suspending agents and dispersing agents. "Lotions" can also have as the dispersed phase liquid substances that are immiscible with the vehicle and are usually dispersed by means of emulsifying agents or other suitable stabilizers.

As used herein, "cream" refers to a viscous liquid or semi-solid emulsion of either the "oil-in-water" or "water-in-oil type".

As used herein, "ointment" refers to a semisolid preparation containing an ointment base and optionally one or more active agents.

As used herein in the context of pharmaceutical formulations, "gel" refers to a semisolid system containing dispersions of the autophagic inhibitor in a liquid vehicle that is rendered semisolid by the action of a thickening agent or polymeric material ("gelling agent") dissolved or suspended in the liquid vehicle. The liquid can include a lipophilic component, an aqueous component or both. "Gels" can also be emulsions. Some gels, however, are not emulsions because they do not contain a homogenized blend of immiscible components Discussion Endometriosis is a gynecological disease that afflicts women of child-bearing age. Although itself benign, it is a very painful condition characterized by endometriotic lesions at ectopic sites leading to infertility and an increased risk of specific subtypes of ovarian cancer.

Endometriosis is believed to result from biological or physiological events that resemble metastasis which can be characterized into 6 stages: (1) shedding of cells, (2) cell survival, (3) escape from immune surveillance, (4) adhesion to peritoneum, (5) angiogenesis, and (6) bleeding. Although formation of an endometriotic lesion is dependent on the combination of these events, the first step, survival, which, if it occurs, will allow cells to implant and develop into an endometriotic lesion and thus plays an important role in the pathogenesis of endometriosis. Indeed, altered cell death characteristics in the eutopic endometrium of women with endometriosis will contribute to survival of retrograde endometrial cells.

Anoikis is a cell death event due to decreased cell adhesion and elimination of cells detached from substratum. Thus, anoikis will prevent epithelial cells from shedding from their original location ("misplaced" cells), to colonize at ectopic sites. In cancer, anoikis resistance leads to tumor metastases.

Mechanisms of anoikis resistance include (1) acquisition of an epithelial-mesenchymal transition (EMT)-like phenotype, (2) activation of integrin and downstream signaling mediators (i.e. Src, FAK, and ILK), (3) increased expression of TrkB, a neurotrophic tyrosine kinase receptor (suppressor of caspase-associated anoikis) in endometriosis patients and certain cancers associated with cancer metastases and activation of the pro-survival PI3K/AKT pathway and (4) autophagy which promotes survival leading to increased attachment to the extracellular matrix (ECM). Autophagy, a survival mechanism that is activated in response to multiple stresses, is a "self-eating" process whereby damaged cellular material and organelles are sequestered in autophagosomes and degraded. Autophagy allows cells to survive given that they re-adhere to ECM in a timely fashion. Interestingly, detachment-induced autophagy directly results from a loss of ECM-integrin engagement. Epithelial cells depend on integrin-mediated cell adhesion to the ECM for proper growth and survival. The pathways linking loss of integrin engagement at the cell surface to activation of the autophagic machinery remain elusive.

In sum, epithelial cells, such as endometrial cells, depend on integrin-mediated cell adhesion to the ECM for proper growth and survival. Cell detachment from the ECM leads to anoikis, a cell death event, preventing colonization of cells at ectopic sites. If autophagy is induced, cells will escape anoikis and survive. Autophagy, a "self-eating" process whereby damaged cellular material and organelles are sequestered in autophagosomes and degraded, is a survival mechanism activated in response to multiple stresses. As demonstrated herein, dysregulation of autophagy in endometriotic cells contained in endometrial lesions contributes to aberrant cell survival. With this in mind, in one embodiment, an autophagic inhibitor is administered to a subject having endometriosis. In other embodiments, an endometriotic cell is contacted with an autophagic inhibitor. By inhibition of autophagy, at least one symptom of endometriosis, such as lesion size, can be reduced.

Until now, it was not known that a symptom of endometriosis can be alleviated or mitigated by inhibiting autophagy in endometrial cells or endometriotic cells. Indeed, it was unknown how autophagy and its dysregulation affect endometrial cell survival and its contribution to the development of endometriotic lesions. This is likely due, in part, that endometriosis is a benign tumor and autophagy has only been correlated to metastatic tumors that are typically affiliated with invasive cancer tumors.

With that said, disclosed herein are compositions, formulations, methods, and assays that can improve the treatment, diagnosis, and/or prognosis of endometriosis and endometriotic lesions. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Cell Lines

Described herein are life-extended populations of cells generated from endometriotic lesions after in vitro culturing. In an embodiment, a life-extended population of cells contains an endometriotic cell, where the endometriotic cell is the in vitro progeny of a cell isolated from an endometriotic lesion, and where the endometriotic cell can have greater protein expression of one or more of the following autophagic markers selected from the group of ATG7, ATG5, and hVps34 as compared to a suitable non-endometriotic control cell or other control cell. Suitable non-endometriotic control cells include, but are not limited to ovarian cancer cells, non-diseased ovarian epithelial cells, and surface ovarian epithelial (T80) cells. In some embodiments, the life-extended cells also express large T antigen.

The life-extended population of cells can be used as a research tool to assess the effectiveness and safety of compounds to treat endometriosis. In some embodiments, the population of cells is a personalized population of cells. This allows the determination of the efficacy of treatments on the cells from endometriotic lesions from the subject that will receive the treatment.

The life-extended endometriotic cells can be prepared from primary endometriotic cells. Primary endometriotic cells can be maintained in a 1:1 mixture of Medium 199 and MCDB131 Medium supplemented with about 8% fetal bovine serum, penicillin (100 U/mL; diluted 1:100 in complete culture media)/streptomycin (100 mg/mL; diluted 1:100 in complete culture media), and insulin (5 mg/mL)/transferrin (5 mg/mL)/selenium (ITS) (5 µg/mL).

In some embodiments, primary endometriotic cells are transformed them to ubiquitously or conditionally express oncogene. In other embodiments, primary endometriotic cells are infected with viral particles carrying and SV40 large T antigen gene, such that the transformed cells express a SV40 large T antigen.

Pharmaceutical Formulations

Provided herein are pharmaceutical formulations containing an effective amount of an autophaghic inhibitor or active derivative thereof in a pharmaceutical carrier appropriate for administration to an individual in need thereof. The individual in need thereof can have or can be suspected of having endometriosis or an endometriotic lesion. Formulations can be administered orally, intravenously, intramuscularly, intravaginally, intraperitoneally, rectally, perenterally, topically, intranasally, or subcutaneously. Suitable autophagic inhibitors include but are not limited to chloroquine, hydroxychloroquine (also referred to herein as HCQ), and Lys05, pharmaceutically acceptable salts of chloroquine, pharmaceutically acceptable salts of hydroxychloroquine, pharmaceutically acceptable salts of Lys05, antibodies that specifically bind to a positive inducer of autophagy in endometrial cells, siRNA, miRNA, piRNA, or other RNA species that specifically binds to a positive inducer of autophagy in endometrial cells, and other molecules, compounds, or substances which bind or otherwise interact with a protein or other molecule involved in maintaining or increasing autophagy so as to reduce autophagy in the cell.

Parenteral Formulations

The autophagic inhibitor or active derivative thereof can be formulated for parenteral delivery, such as injection or infusion, in the form of a solution or suspension. The autophagic inhibitor can be HCQ or a pharmaceutical salt thereof. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the autophagic inhibitor or active derivative thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the autophagic inhibitor or active derivate thereof.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the autophagic inhibitor or active derivative thereof in the required amount in the appropriate solvent or dispersion medium with one or more of the excipients listed above, as required, followed by filtered sterilization. Dispersions can be prepared by incorporating the various sterilized autophagic inhibitor or derivative thereof into a sterile vehicle which contains the basic dispersion medium and the required other ingredients from those listed above. case of Sterile powders for the preparation of sterile injectable solutions can be prepared by vacuum-drying and freeze-drying techniques, which yields a powder of the autophagic inhibitor or active derivative thereof plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more autophagic inhibitor or active derivative thereof. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration can also contain one or more excipients, such as dispersing agents, wetting agents, and suspending agents.

Topical Formulations

The autophagic inhibitor or active derivative thereof can be formulated for topical administration. The autophagic inhibitor can be HCQ or a salt thereof Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the conjugates can be administered as a liquid formulation, such as a solution or suspension, a semi-solid formulation, such as a lotion or ointment, or a solid formulation. In some embodiments, the autophagic inhibitor is formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodimenst, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil but can be used in the oil phase as surfactants or emulsifiers.

Lotions containing an autophagic inhibitor are also described herein. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing an autophagic inhibitor are also described herein. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Also described herein are ointments containing an autophagaic inhibitor and a suitable ointment base. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing an autophagic inhibitor, a gelling agent, and a liquid vehicle. Suitable gelling agents include, but are not limited to, modified celluloses, such as hydroxypropyl cellulose and hydroxyethyl cellulose; carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that include the autophagic inhibitor. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The autophagic inhibitors can be prepared in enteral formulations, such as for oral administration. The autophagic inhibitor can be HCQ, active derivative thereof, or pharmaceutical salt thereof. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing an autophagic inhibitor are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing an autophagic inhibitor can be prepared using one or more pharmaceutically acceptable excipients, including diluents, preservatives, binders, lubricants, disintegrators, swelling agents, fillers, stabilizers, and combinations thereof.

Delayed release dosage formulations can be prepared as described in standard references such as "Pharmaceutical dosage form tablets", eds. Liberman. et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing an autophagic inhibitor can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, one or more additional active agents are included in the pharmaceutical formulation that can contain an autophagic inhibitor such as HCQ. Suitable additional active agents include, but are not limited to, antipyretics, immunomodulators, chemotherapeutics and analgesics.

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Treatments

It is demonstrated herein that autophagy can remove endometrial cells from a normal apoptotic pathway, which can allow the cells to survive and develop into ectopic lesions. Therefore, in some embodiments, autophagy can be inhibited in an endometrial cell, endometriotic cell, or endometriotic lesion cell, or populations thereof, by contacting the cell or population of cells with an effective amount of an autophagic inhibitor or active metabolite thereof. In some embodiments, contacting the cell with an autophagic inhibitor can include administering an autophagic inhibitor or pharmaceutical formulation thereof to a subject in need thereof as described elseswhere herein. Suitable autophagic inhibitors include, but are not limited to, chloroquine, hydroxychloroquine, and Lys05, pharmaceutically acceptable salts of chloroquine, pharmaceutically acceptable salts of hydroxychloroquine, pharmaceutically acceptable salts of Lys05, pharmaceutically acceptable formulations containing an effective amount of chloroquine, Lys05 or hydroxychloroquine, active derivatives of chloroquine, Lys05 or hydroxychloroquine, antibodies that specifically bind to a positive inducer of autophagy in endometrial cells, siRNA, miRNA, piRNA, or other RNA species that specifically binds to a positive inducer of autophagy in endometrial cells, and other molecules, compounds, or substances which bind or otherwise interact with a protein or other molecule involved in maintaining or increasing autophagy so as to reduce autophagy in the cell. In some embodiments, ATG5 and/or ATG7 mRNAs can be targeted using siRNAs or other RNA species that can specifically bind with the ATG5 and/or ATG7 mRNA. In other embodiments, enometriotic cells are contacted with compounds, molecules, or pharmaceutical formulations thereof that disrupt the interaction between beclin-1 and hVps34. In further embodiments, endometriotic cells are contacted with compounds, molecules, or pharmaceutical formulations thereof that inhibit activation of ATG1/ULK1.

In some embodiments, the binding of an RNA species or other molecule to a protein or other molecule in the autophagic pathway results in a reduction in the expression and/or function of the bound protein or other molecule.

The effective amount of the autophagic inhibitor, such as HCQ, or pharmaceutical formulation thereof can range from about 1 mg/kg to about 200 mg/kg. In some embodiments, the effective amount ranges from about 10 mg/kg to about 60 mg/kg. If further embodiments, the effective amount ranges from about 1 mg to about 700 mg. In some embodiments the effective amount can be about 400 mg to about 600 mg. In further embodiments, the endometrial cell, endometriotic cell, or endometriotic lesion cell has a greater expression of at least one of the following autophagic markers selected from ATG7, ATG5, and hVps34 as compared to a control cell or population of control cells.

In other embodiments, an effective amount of the autophagic inhibitor, such as HCQ, or pharmaceutical formulation thereof can be administered to a subject having endometriosis, an endometriotic lesion, or suspected of having endometriosis or an endometriotic lesion. Administration can be systemic or localized. In some embodiments, the autophagic inhibitor is as described above. The effective amount can be administered one or more times per day. In an embodiment, the effective amount is administered once daily. In some embodiments, the effective amount can be about 400 mg to about 600 mg given once daily. In another embodiment, the effective amount is administered twice daily. The effect amount can be administered one or more times per week. In some embodiments the effective amount is administered 1 day per week. In other embodiments, the effective amount is administered 2 to 7 days per week. The effective amount can be administered more than one time per month. In some embodiments, the effective amount is administered 2 times per week.

In some embodiments, the effective amount of an autphagic inhibitor or pharmacuetical formulation thereof, can be administered in a dosage form. The effective amount can be divided into multiple dosage forms. For example, the effective amount can be split into two dosage forms and the one dosage forms can be administered, for example, in the morning, and the second dosage form can be administered in the evening. Although the effective amount is given over two doses, in one day, the subject receives the effective amount. In some embodiments the effective amount is about 400 to about 600 mg per day.

The dosage form can be formulated for oral, vaginal, intravenous, transdermal, subcutaneous, intraperitoneal, or intramuscular administration. The effective amount can range from about 1 mg/kg to about 200 mg/kg. In some embodiments, the effective amount ranges from about 10 mg/kg to about 60 mg/kg. The effect amount can be administered with or without food. Administration with food is such that there is food present in the stomach at the same time that the effective amount is administered or shortly thereafter. In other embodiments, an effective dose of about 400 mg to 600 mg can be administered orally once daily with food or a glass of milk. In some embodiments, an initial effective dose of about 400 mg to about 600 mg can be administered orally once daily with food or a glass of milk until an improvement in at least one symptom is achieved, which is followed by a maintenance dose of about 50% of the initial dose given orally once daily.

Assays

Also described herein are assays for detecting biomarkers of endometriosis or endometriotic lesion, diagnosing, and/or prognosing endometriotic lesions and endomentriosis. Alteration of expression and/or activation of ATG-5, ATG-7, ATG-9, DJ-1(Park7), hVps34, beclin-1, p-ULK1, ATG1 (ULK1), p-mTOR, mTOR, integrin, Src, FAK, ILK, rkB, AKT, LC3A, LC3 B, TSC1, TSC2, HO-1, PTEN, ARID1A, PIK3CA, K-RAS, BCL-2, ATG16, ATG12, ATG10, ATG3, LC3-1, ATG4, EVI1, RON, EGFR, SnoN, SkiL TGFβRII, p53, Smad2/3, p-ERK, ERK, PARP, cleaved PARP, p62, ferritin, E-cadherin, N-cadherin, vimentin cytokeratin-18 and/or combinations thereof. can be involved in the pathogenesis of endometriotic lesions. Evaluation of one or a combination of the aforementioned biomarkers can provide previously unappreciated information that can aid in an improved, more accurate, and/or earlier diagnosis or prognosis than conventional techniques.

Capture Molecules

Described herein are capture molecules configured to specifically bind a biomarker that can be involved in the pathogenesis of endometriosis and/or endometriotic lesions. The capture molecules can be an antibody or fragment thereof, aptamer, affibody, polynucleotide, peptide, or polypeptide. In some embodiments, the capture molecule is a polynucleotide. In other embodiments, the capture molecule is an antibody or fragment thereof. The antibody can be a polyclonal antibody. Methods of producing polyclonal antibodies are generally known in the art. In some embodiments, the antisera containing a polyclonal antibody is affinity purified against an epitope or antigen the polyclonal antibody was raised against to obtain only the antibody(ies) or fragment(s) thereof that specifically binds the epitope or antigen. Methods of affinity purification of polyclonal antibodies are generally known in the art. The antibody can be a monoclonal antibody. Methods of producing monoclonal antibodies are generally known in the art. In some embodiments, the antibody is contained in an antiserum or culture media. In other embodiments, the antibody is provided as a lyophilized or dried product that can be reconstituted to a desired concentration.

The antibody can be used at any concentration or dilution. In some embodiments, the antibody is diluted 1:1 to 1:500,000 in a suitable diluent. Suitable diluents are generally known, are commercially available, and include but are not limited to water, dimethyl sulfoxide (DMSO), ethanol and mixtures thereof. The diluent can contain one or more preservatives, protease inhibitors, salts, and pH indicators, blocking substrates, including but not limited to bovine serum album.

Biomarkers

The capture molecules described herein can be configured to specifically bind to a biomarker as described herein. In some embodiments, the biomarker can be involved in the pathogenesis of endometriosis. The biomarker can be involved in the autophagic pathway, the development of anoikis resistance, and/or the activation status of a cell. The biomarker can be a oligonucleotide, polynucleotide, peptide, polypeptide, lipid, fatty acid, a polysaccharide, primary metabolite, secondary metabolite, terpenes, or combinations thereof.

The biomarkers involved in pathogenesis of endometriotic lesions can be ATG-5, ATG-7, ATG-9, DJ-1(Park7), hVps34, beclin-1, p-ULK1, ULK, ATG1, p-mTOR, mTOR, p-AMK, AMK, integrin, Src, FAK, ILK, rkB, PI3K, AKT, LC3A (LC3-1), LC3 B (LC3-II), TSC1, TSC2, HO-1, PTEN, ARID1A, PIK3CA, K-RAS, PI3K111, BCL-2, ATG16, ATG12, ATG10, ATG3, LC3-1, ATG4, EVI1, RON, EGFR, SnoN, SkiL TGFβRII, p53, Smad2/3, p-ERK, ERK, PARP, cleaved PARP, p62, ferritin, E-cadherin, N-cadherin, vimentin cytokeratin-18 and/or combinations thereof.

Assays Using the Capture Molecules

The capture molecules described herein can be used in an assay to detect and/or quantify an amount of one or more biomarkers present in a sample or component thereof obtained from a subject. The sample can be a bodily fluid, an amount of bodily tissue, organ or bone, cell obtained from a subject, population of cells obtained from a subject, or a cell or population of cells obtained from a subject and cultured in vitro.

The assay can contain the steps of contacting a sample or component thereof with a capture molecule as described herein that is configured to specifically bind to a biomarker as described herein and detecting the presence of specific binding of the biomarker by the capture molecule as compared to a control. The control can be an assay control, a negative control capture molecule (specifically binds to a molecule not involved in the pathogenesis of endometriotic lesions), positive control capture molecule (specifically binds to a molecule known to be involved in the pathogenesis of endometriotic lesions), a negative control sample (a sample derived from a non-endometriotic tissue, subject, cell, or population of cells), a positive control sample (a sample derived from an endometriotic tissue, cell, or population of cells or subject with endometriosis). The assay can be configured to be used to aid in the diagnosis, treatment, or prognosis of endometriosis and endometriotic lesions by the specific capture molecule or combination of capture molecules included in the assay.

The assay can also contain the step of processing the sample prior to contacting the sample or component thereof with the capture molecule. The step of processing the sample, where the sample is whole blood, can contain the step of processing the whole blood to form a processed blood plasma fraction. Methods of obtaining blood plasma from whole blood are generally known in the art. In these embodiments, the processed blood plasma fraction is contacted with the capture molecule as opposed to the whole blood. In other embodiments, the step of processing the sample, where the sample is whole blood, can contain the step of processing the whole blood to form a processed white blood cell fraction. Methods of obtaining a white blood cell fraction or buffy coat are generally known in the art. In these embodiments, the processed white blood cell fraction is contacted with the capture molecule as opposed to whole blood.

The assay can also contain the step of processing a tissue sample prior to contacting the tissue sample with the capture molecule. The tissue can be fixed in a suitable fixing solution prior to contacting the capture molecule. Suitable fixing solutions are generally known in the art and include, but are not limited to, paraformaldehyde and dilutions thereof. The tissue can be embedded in a suitable substrate prior to contacting the capture molecule. Suitable substrates include, but are not limited to, paraffin, agar, gelatin, or other wax The sample or component thereof can be processed using any suitable chemical method, physical method, or combinations thereof to release, concentrate, separate and/or isolate the biomarker(s) or other components of the sample prior to contacting the sample with the capture molecule.

The assay can also contain the step of quantifying or calculating an amount of a biomarker present in the sample and/or the step of quantifying an amount of biomarker that is specifically bound to a capture molecule. In some embodiments, the amount of biomarker present in the sample is quantified by quantifying the amount of biomarker that is specifically bound to a capture molecule. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

In some embodiments, the step of detecting the presence of specific binding of the biomarker by the capture molecule and/or the step of detecting, measuring, and/or quantifying the amount of biomarker specifically bound by the capture molecule is performed, at least in part, using a method selected from an array, polymerase chain reaction (PCR), quantitative PCR (qPCR), real-time PCR, real-time qPCR, flow cytometry, a western blot, an enzyme linked immunosorbant assay, immunohistochemistry, immunocytochemistry, in situ hybridization, nucleotide sequencing, mass spectrometry, 1-D gel electrophoresis, 2-D gel electrophoresis, high-performance liquid chromatography, liquid chromatography, affinity chromatography, or combinations thereof.

In further embodiments, the assay can contain the steps of contacting a sample or component thereof as described herein with a plurality of capture molecules, where each capture molecule is configured to specifically bind to a biomarker that can be involved in the pathogenesis of endometriotic lesions, and detecting the presence of specific binding of at least one biomarker by at least one of the capture molecules in the plurality of capture molecules. In some embodiments, the plurality of capture molecules in the assay is configured such that biomarkers related to the autophagic pathway, development of anoikis resistance, activation status of the cell, or combinations thereof that may be present in a sample or component thereof can be evaluated by the assay. In some embodiments, the plurality of capture molecules can be configured such that the autophagic biomarkers LC3A, ATG7, ATG5, beclin-1, and hVps34 can be detected. In some embodiments, the plurality of capture molecules is configured such that the activation status biomarkers p-ULK/ATG1, p-mTOR, pAMK can be detected. In further embodiments, the plurality of capture molecules is configured such that the autophagic biomarkers LC3A, ATG7, ATG5, beclin-1, and hVps34 and the activation status biomarkers p-ULK/ATG1, p-mTOR, pAMK can be detected.

The assay can be configured such that each capture molecule in the plurality of capture molecules is configured to each specifically bind to a different biomarker. In other embodiments, the assay can be configured such that at least two of the capture molecules specifically bind to a different biomarker. In further embodiments, the assay can be configured such that at least two of the capture molecules specifically bind to the same biomarker. In embodiments where the assay contains the step of contacting a sample obtained from a subject with a plurality of capture molecules, the assay can further contain any additional steps as described herein, including, but not limited to, quantifying the specific binding of one or more biomarkers by one or more capture molecules and processing the sample or component thereof.

Arrays

Also described herein are arrays, including, microarrays that can be used to detect one or more molecules of interest (biomarkers) present in a sample. In an array, one or more capture molecules are attached to or operatively linked to a support in essentially discrete locations on the support. The capture molecules are as described herein. The discrete locations on the support where the capture molecule(s) are attached to or operatively linked are individually referred to as a feature of the array and collectively as features. The features can be arranged in any desired arrangement on the support. The arrangement can be such that each feature has its own coordinate so as to allow identification of the capture molecule and/or biomarker detected at any given discrete location in the array according to the coordinate of the feature. These arrays can also be referred to as "ordered arrays". The features can be arranged on the support to be 0.01 nm to 1 cm apart from another feature on the support. A single feature can contain a single capture molecule (singleplex) or can contain more than one capture molecules (multiplex).

The support can be solid or semi-solid. The support can be rigid or be flexible. The support can contain one or more specialized layers that affect the functionality or performance of the array. The support can be two-dimensional or three-dimensional. The support can be made of glass, such as silicon dioxide or borosilicate; plastic, such as polystyrene, nylon, polyvinylidene difluoride; a fibrous material, such as cellulose, carboxy methyl cellulose, or nitrocellulose; a gel, such as agarose, a hydrogel, or polyacrylamide, The support can be formed into any desired shape, including but not limited to a square, a rectangle, a circle, a cube, a rectangular prism, or other regular or irregular polygonal shape or its corresponding three-dimensional shape. The support can have a length, a width, a height, a radius, and/or a diameter. The length of the support can range from about 1 µm to about 10 cm. The height of the support can range from about 1 µm to about 10 cm. The width of the support can range from about 1 µm to about 10 cm. The radius of the support can range from about 1 µm to about 10 cm. The diameter of the support can range from about 1 µm to about 10 cm.

The support can contain a single layer to which the capture molecule is attached or operatively linked. In these embodiments, the support can also be referred to as the surface layer. In other embodiments, the support can contain more than one layer. In embodiments with more than one layer, the layer to which the capture molecule is attached or operatively linked is referred to as the surface layer. The surface layer can be modified to affect the interaction and/or reduce non-specific binding between a capture molecule and the support and/or the capture molecule and the biomarker. In some embodiments, surface layer is modified to enhance the interaction between the capture molecule and the surface layer and/or the interaction between the capture molecule and its corresponding biomarker. The modification of the surface layer can also reduce non-specific binding by the capture molecule and/or the biomarker.

In some embodiments, the surface layer is modified with a chemical modification. Suitable chemical modifications include, but are not limited to, reactive hydroxide groups, reactive primary, secondary, tertiary, and/or quaternary amine groups, a monolayer of a reactive antibody including but not limited to anti-glutathione S-transferase (anti-GST) antibodies, reactive epoxide groups, reactive methacrylate groups, aldehyde reactive groups, reactive A/G proteins that bind immunoglobulins, and 3-D film coatings, which are polymeric coatings containing activated covalent binding sites. In some embodiments, 3-D film polymeric coatings include, but are not limited to, polysaccharides and hydrophilic polymers. In some embodiments, the 3-D film activated covalent binding sites include, but are not limited to, N-hydroxy succamide esters. The surface layer can be modified to be positively charged, neutral, or negatively charged. The surface layer can be modified to be hydrophilic, hydrophobic, or to contain a mix of hydrophobic and hydrophilic regions. In some embodiments, the modifications are patterned on the surface layer to form discrete functionalized areas to which the capture molecule is attached or operatively-linked. In some embodiments having mixed hydrophobic and hydrophilic regions, the hydrophilic regions are separated by hydrophobic regions. In other embodiments, having mixed hydrophobic and hydrophilic regions, the hydrophobic regions are separated by hydrophilic regions.

In some embodiments, the surface layer is a gel, including but not limited to agarose, a hydrogel, or polyacrylamide. In some embodiments the support contains multiple discrete gel surface layers. These gel surface layers are also referred to as pads and can be arranged on the support in an ordered arrangement such that each gel pad is a feature of the array. In some embodiments, the same capture molecule(s) are attached to or operatively linked to all the gel pads forming the surface layer of the support. In other embodiments, at least two of the gel pads have at least one different capture molecule attached or operatively linked thereto.

The support can be configured to have one or more three dimensional discrete indentations or depressions in the surface layer. The capture molecule(s) can be attached or operatively linked to the indentation. The three dimensional indentations can be square, rectangular, round, or irregular shaped. The three dimensional indentations can form wells or channels. One or more indentations can be connected to another indentation by a three dimensional connector channel extending between the one or more wells. In some embodiments, the connector channel is a microfluidic channel. In some embodiments, the microfluidic channel contains wicking paper. A dimension of the indentation can range from about 1 µm to about 10 cm. In some embodiments, a length of an indentation ranges from about 1 µm to about 10 cm. In further embodiments, a width of an indentation can range from about 1 µm to about 10 cm. In additional embodiments, a height of an indentation can range from about 1 µm to about 10 cm. In other embodiments, the radius of an indentation can range from about 1 µm to about 10 cm. In further embodiments, the diameter of an indentation can range from about 1 µm to about 10 cm. The indentations can be so dimensioned so as to hold a specific volume. In some embodiments, the specific volume ranges from about 1 nL to about 1,000 mL. In a single array, the indentations can all be about the same dimension. In other embodiments, at least two of the indentations differ in at least one dimension. Any surface of an indentation can be modified as described above with respect to modification of the surface layer.

The support can also contain additional layers beneath the surface layer and within the support. The additional layers can be directly beneath the surface layer or contain other layers, such as the support, between the additional layer and the surface layer. The additional layer can improve the signal to noise ratio, affect signal production produced by the binding of a capture molecule to a biomarker or other substrate, and affect other properties or performance parameters of the array. In some embodiments the additional layer is a dielectric layer. The dielectric layer can improve the reflection of the signal produced upon binding of a capture molecule and a biomarker.

In some embodiments, the array is a tissue microarray, which refers to a block of paraffin or other tissue embedding material that contains at least two tissue samples, where the tissue samples are positioned at discrete locations and arranged in a known order. The tissue samples can be core biopsies. The block can then be sliced and a slice of this block can be attached to or operatively linked to a suitable solid support. Suitable solid supports are described elsewhere herein. The block or slice thereof can then be contacted with a capture molecule and specific binding of a biomarker and the capture molecule can be detected. In some embodiments, more than one slices of the block are attached or operatively linked to the solid support.

Methods of Diagnosing and Prognosing Endometriosis and Endometriotic Lesions

Also described herein are methods of diagnosing and prognosing endometriosis and endometriotic lesions of a subject. The methods of diagnosing and/or prognosing endometriosis and endometriotic lesions of a subject can be performed using one or more of the capture molecules, assays, kits, and arrays described herein.

Some methods of diagnosing and/or prognosing endometriosis and/or endometriotic lesions can include the steps of contacting a sample or component thereof with a capture molecule configured to bind a biomarker as described herein, detecting the presence of specific binding of the biomarker by the capture molecule, and diagnosing a stage, symptom, presence, and/or state of endometriosis and/or an endometriotic lesion when the presence of specific binding of the biomarker by the capture molecule is detected as compared to a control. In some embodiments, LC3A, LC3B, ATG7, ATG5, hVps34, and/or DJ1 (Park 7) can be detected in the sample. The sample can be a bodily fluid, an amount of bodily tissue, organ or bone, cell obtained from a subject, population of cells obtained from a subject, or a cell or population of cells obtained from a subject and cultured in vitro. The sample or component thereof can be obtained from subject having or suspected of having endometriosis or a endometriotic lesion.

The control can be an assay control, a negative control capture molecule (specifically binds to a molecule not involved in the pathogenesis of endometriotic lesions), positive control capture molecule (specifically binds to a molecule known to be involved in the pathogenesis of endometriotic lesions), a negative control sample (a sample derived from a non-endometriotic tissue, subject, cell, or population of cells), a positive control sample (a sample derived from an endometriotic tissue, cell, or population of cells or subject with endometriosis).

Other methods of diagnosing and/or prognosing endometriosis and/or an endometriotic lesion can include the steps of contacting a sample or component thereof with a capture molecule configured to bind a biomarker as described herein, detecting the presence of specific binding of the biomarker by the capture molecule, and diagnosing a stage, symptom, presence, and/or state of endometriosis and/or an endometriotic lesion when the presence of specific binding of the biomarker by the capture molecule is not detected as compared to a control.

Further methods of diagnosing and/or endometriosis and/or an endometriotic lesion can include the steps of contacting a sample or component thereof with a capture molecule configured to bind a biomarker as described herein, detecting the presence of specific binding of the biomarker by the capture molecule, quantifying an amount of biomarker specifically bound by the capture molecule, and diagnosing and/or prognosing a subject with endometriosis or an endometriotic lesion when the amount of specifically bound biomarker is greater than a control. In some embodiments, the amount of LC3A, LC3B, ATG7, ATG5, hVps34, and/or DJ1 (Park 7) can be greater than the control. The amount can be an absolute amount or a relative amount. The amount can be relative to a control amount, a reference amount, and/or a standard amount. An absolute amount can be calculated from a standard curve. The amount of specifically bound biomarker can be about 0% to about 50% greater than the control, 50% to 100% greater than the control, about 100% to about 500% greater than the control, or greater than about 500% than a control.

Other methods of diagnosing and/or prognosing endometriosis and/or an endometriotic lesion can include the steps of contacting a sample or component thereof with a capture molecule configured to bind a biomarker as described herein, detecting the presence of specific binding of the biomarker by the capture molecule, quantifying an amount of biomarker specifically bound by the capture molecule, and diagnosing and/or prognosing a subject with endometriosis or an endometriotic lesion when the amount of specifically bound biomarker is less than the control. The amount can be an absolute amount or a relative amount. The amount can be relative to a control amount, a reference amount, and/or a standard amount. An absolute amount can be calculated from a standard curve. The amount of specifically bound biomarker can be about 0% to about 50% less than the control, 50% to 100% less than the control, about 100% to about 500% less than the control, or less than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

In other methods of diagnosing endometriosis and/or prognosing an endometriotic lesion can include the steps of contacting a sample or component thereof as described herein obtained from a subject with a plurality of capture molecules, where each capture molecule is configured to specifically bind to a biomarker as described herein, detecting the presence of specific binding of at least one biomarker by at least one of the capture molecules in the plurality of capture molecules, and diagnosing and/or prognosing endometriosis and/or endometriotic lesions if the presence of at least one of biomarker bound by at least one of the capture molecules of the plurality of capture molecules is detected. In other embodiments, diagnosing endometriosis and/or endometriotic lesions occurs if the presence of at least two, three, or four biomarkers bound by one or more capture molecules of the plurality of molecules is detected. In some embodiments, the plurality of capture molecules in the assay is configured such that biomarkers related to the autophagic pathway, development of anoikis resistance, activation status of the cell, or combinations thereof can be evaluated by the method. In some embodiments, LC3A, LC3B, ATG7, ATG5, hVps34, DJ1 (Park 7), and/or combinations thereof can be detected in the sample.

The amount can be relative to a control amount, a reference amount, and/or a standard amount. An absolute amount can be calculated from a standard curve. The amount of specifically bound biomarker can be about 0% to about 50% less than the control, 50% to 100% less than the control, about 100% to about 500% less than the control, or less than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

In other methods of diagnosing and/or prognosing endometriosis and/or an endometriotic lesion can include the steps of contacting a sample or component thereof as described herein obtained from a subject with a plurality of capture molecules, where each capture molecule is configured to specifically bind to a biomarker as described herein, detecting the specific binding of at least one biomarker by at least one of the capture molecules in the plurality of capture molecules, quantifying an amount of a biomarker that is specifically bound by a capture molecule in the plurality of capture molecules, and diagnosing and/or prognosing endometriosis and/or endometriotic lesions if the amount of at least one of biomarker bound by the capture molecule is greater than a control. In other embodiments, diagnosing and/or prognosing endometriosis and/or endometriotic lesions occurs if the amount of at least two biomarkers bound by one or more capture molecules of the plurality of molecules is greater than the control. In some embodiments, the plurality of capture molecules in the assay is configured such that biomarkers related to the autophagic pathway, development of anoikis resistance, activation status of the cell, or combinations thereof can be evaluated by the method. In some embodiments, the amount of LC3A, LC3B, ATG7, ATG5, hVps34, DJ1 (Park 7), and/or combinations thereof can be greater than a control.

The amount can be relative to a control amount, a reference amount, and/or a standard amount. An absolute amount can be calculated from a standard curve. The amount of specifically bound biomarker can be about 0% to about 50% less than the control, 50% to 100% less than the control, about 100% to about 500% less than the control, or less than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

In other methods of diagnosing and/or prognosing endometriosis and/or an endometriotic lesion can include the steps of contacting a sample or component thereof as described herein obtained from a subject with a plurality of capture molecules, where each capture molecule is configured to specifically bind to a biomarker as described herein, detecting the specific binding of at least one biomarker by at least one of the capture molecules in the plurality of capture molecules, quantifying an amount of a biomarker that is specifically bound by a capture molecule in the plurality of capture molecules, and diagnosing and/or prognosing endometriosis and/or endometriotic lesions if the amount of at least one of biomarker bound by the capture molecule is less than a control. In other embodiments, diagnosing and/or prognosing endometriosis and/or endometriotic lesions occurs if the amount of at least two biomarkers bound by one or more capture molecules of the plurality of molecules is less than the control. In some embodiments, the plurality of capture molecules in the assay is configured such that biomarkers related to the autophagic pathway, development of anoikis resistance, activation status of the cell, or combinations thereof can be evaluated by the method.

The amount can be relative to a control amount, a reference amount, and/or a standard amount. An absolute amount can be calculated from a standard curve. The amount of specifically bound biomarker can be about 0% to about 50% less than the control, 50% to 100% less than the control, about 100% to about 500% less than the control, or less than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

In other methods of diagnosing and/or prognosing endometriosis and/or an endometriotic lesion can include the steps of contacting a sample or component thereof as described herein obtained from a subject with a plurality of capture molecules, where each capture molecule is configured to specifically bind to a biomarker as described herein, detecting the specific binding of at least one biomarker by at least one of the capture molecules in the plurality of capture molecules, quantifying an amount of a biomarker that is specifically bound by a capture molecule in the plurality of capture molecules, and diagnosing and/or prognosing endometriosis and/or endometriotic lesions if the amount of at least one biomarker bound by the capture molecule is less than a control and the amount of at least one biomarker bound by the capture molecule is greater than a control. In other embodiments, diagnosing and/or prognosing endometriosis and/or endometriotic lesions occurs if the amount of at least two biomarkers bound by one or more capture molecules of the plurality of molecules is less than the control and the amount of at least two biomarkers bound by one or more capture molecules of the plurality of molecules is greater than the a control. In some embodiments, the plurality of capture molecules in the assay is configured such that biomarkers related to the autophagic pathway, development of anoikis resistance, activation status of the cell, or combinations thereof can be evaluated by the method. In some embodiments, the amount of LC3A, LC3B, ATG7, ATG5, hVps34, DJ1 (Park 7), and/or combinations thereof can be greater than a control.

The amount can be relative to a control amount, a reference amount, and/or a standard amount. An absolute amount can be calculated from a standard curve. The amount of specifically bound biomarker can be about 0% to about 50% less than the control, 50% to 100% less than the control, about 100% to about 500% less than the control, or less than about 500% than the control. Specific binding of the biomarker and the capture molecule can result in a measurable, detectable, and/or quantifiable signal in binding assays, such as immunoassays. Methods of quantifying the amount of biomarker specifically bound to a capture molecule based on a measureable, detectable, and/or quantifiable signal in a binding assay are generally known in the art.

Any of the methods of diagnosing and/or prognosing described herein can also contain the steps of obtaining the sample from the subject prior to contacting or component thereof with a capture molecule or plurality thereof. In other embodiments, any of the methods described above can also contain the step of processing the sample as previously described herein.

In some embodiments of the methods of diagnosing and/or prognosing described herein, the step of detecting the presence of specific binding of the biomarker by the capture molecule and/or the step of detecting, measuring, and/or quantifying the amount of biomarker specifically bound by the capture molecule can be performed, at least in part, using a method selected from an array, polymerase chain reaction (PCR), quantitative PCR (qPCR), real-time PCR, real-time qPCR, flow cytometry, a western blot, an enzyme linked immunosorbant assay, immunohistochemistry, immunocytochemistry, in situ hybridization, nucleotide sequencing, mass spectrometry, 1-D gel electrophoresis, 2-D gel electrophoresis, high-performance liquid chromatography, liquid chromatography, affinity chromatography, or combinations thereof.

The methods of diagnosing and/or prognosing described herein can also contain the step of processing the sample prior to contacting sample with the capture molecule. The step of processing the sample, where the sample is whole blood, can contain the step of processing the whole blood to form a processed blood plasma fraction. Methods of obtaining blood plasma from whole blood are generally known in the art. In these embodiments, the processed blood plasma fraction is contacted with the capture molecule as opposed to the whole blood. In other embodiments, the step of processing the sample, where the sample is whole blood, can contain the step of processing the whole blood to form a processed white blood cell fraction. Methods of obtaining a white blood cell fraction or buffy coat are generally known in the art. In these embodiments, the processed white blood cell fraction is contacted with the capture molecule as opposed to whole blood.

The methods of diagnosing and/or prognosing described herein can also contain the step of processing a tissue sample prior to contacting the tissue sample with the capture molecule. The tissue can be fixed in a suitable fixing solution prior to contacting the capture molecule. Suitable fixing solutions are generally known in the art and include, but are not limited to, paraformaldehyde and dilutions thereof. The tissue can be fixed in a suitable substrate prior to contacting the capture molecule. Suitable substrates include, but are not limited to, paraffin, agar, gelatin, or other wax.

The sample or component thereof can be processed using any suitable chemical method, physical method, or combinations thereof to release, concentrate, separate and/or isolate the biomarker(s) or other components of the sample prior to contacting the sample with the capture molecule.

Kits

Kits Containing Autophagic Inhibitors

The autophagic inhibitors described herein can be presented as a combination kit. As used herein, the terms "combination kit" or "kit of parts" refers to the compound or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single dosage form (e.g. a tablet) or in separate dosage forms.

When the agents are not administered simultaneously, the combination kit can contain each agent in separate pharmaceutical formulations. The separate pharmaceutical formulations can be contained in a single package or in separate packages within the kit. In some embodiments, the combination kit also includes instructions printed on or otherwise contained in a tangible medium of expression. The instructions can provide information regarding the content of the autophagic inhibitor or pharmaceutical formulations containing the autophagic inhibitor contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions provide directions for administering the autophagic inhibitor or pharmaceutical formulation containing an autophagic inhibitor to a subject having endometriosis.

Kits Containing the Capture Molecules

Also described herein are kits containing one or more capture molecules described herein. In some embodiments, the kit can contain one or more antibodies or fragments thereof configured to specifically bind a biomarker described herein. The kit can contain polynucleotides configured to specifically bind a biomarker described herein The kit can also contain a reagent for performing an array, polymerase chain reaction (PCR), quantitative PCR (qPCR), real-time PCR, real-time qPCR, flow cytometry, a western blot, an enzyme linked immunosorbant assay, immunohistochemistry, immunocytochemistry, in situ hybridization, nucleotide sequencing, mass spectrometry, 1-D gel electrophoresis, 2-D gel electrophoresis, high-performance liquid chromatography, liquid chromatography, affinity chromatography, or combinations thereof. The kit can contain instructions fixed in a tangible medium of expression where the instructions provide for diagnosing and/or prognosing endometriosis and/or an endometriotic lesion.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Tissue Microarray for Evaluation of Autophagy in Endometriotic Lesions A tissue microarray (TMA) was used to evaluate autophagy in endometriotic lesions. The TMA contained endometriotic ectopic lesions from various sites together with eutopic endometrium. Specifically, the TMA contained endometriotic ectopic lesions from various sites together with eutopic (normal and from endometriosis patients) endometrium from specific phases of the endometrium cycle 30. A total of 164 core biopsies obtained from 83 tissue blocks were used to construct the tissue microarray (TMA). For most blocks, 2 different core biopsies were included in the TMA. The total number of cores on the TMA are 29 ovarian endometriosis, 16 fallopian tube endometriosis, 34 peritoneal endometriosis, 4 skin (umbilical) endometriosis, 7 gastrointestinal (GU), 22 eutopic endometrium of patients with endometriosis (EE), 14 control proliferative phase endometrium (PE), and 38 control secretory phase endometrium (SE).

Figures 2A, 2B:
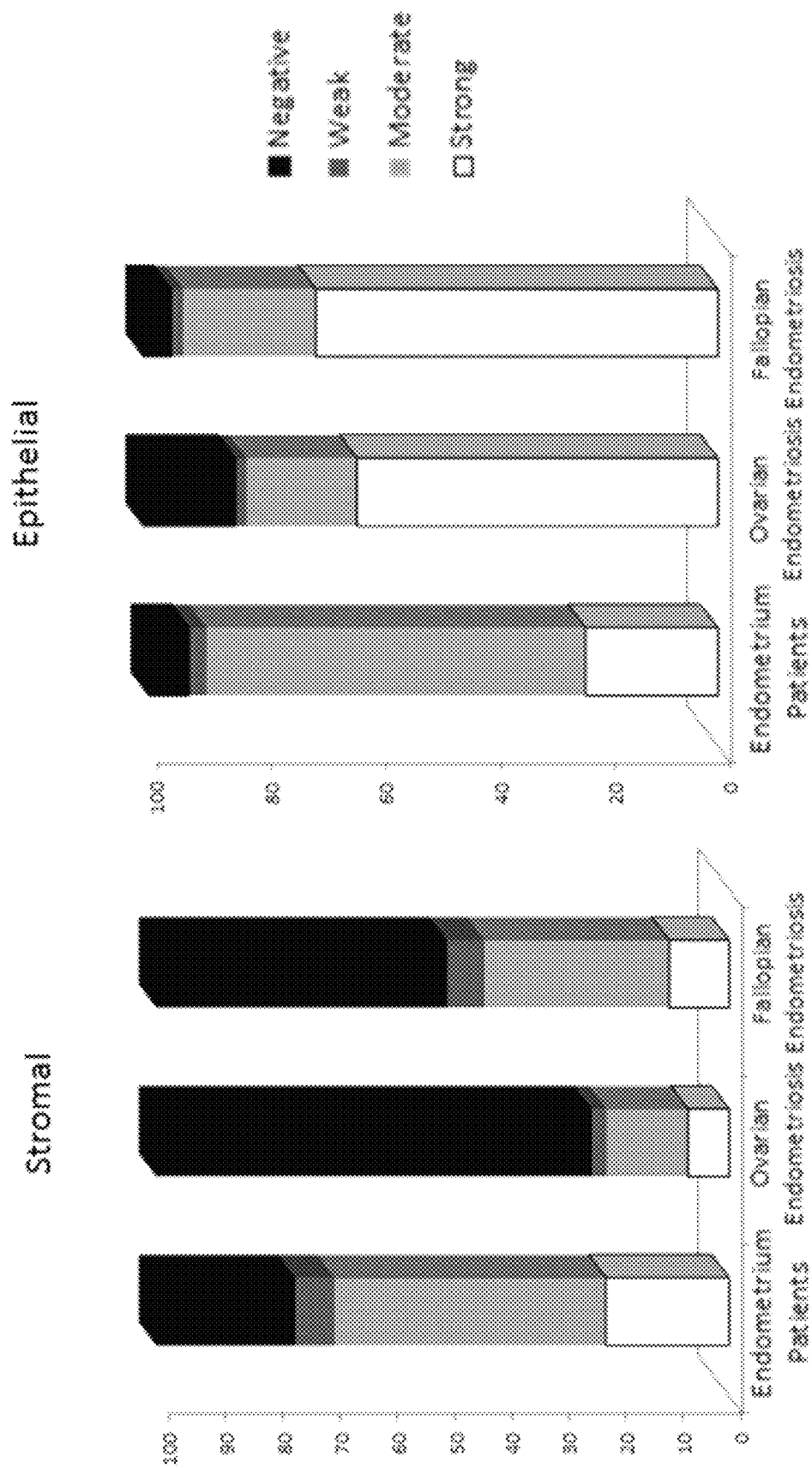
FIGS. 2A-2B demonstrates the results from a qualitative assessment of the intensity of LC3 staining of FIGS. 1A-1E. The intensity of LC3 staining in the stroma was assessed independently from the glandular epithelium. Results are presented as negative, weak, moderate, and strong staining patterns.
Figure 3:
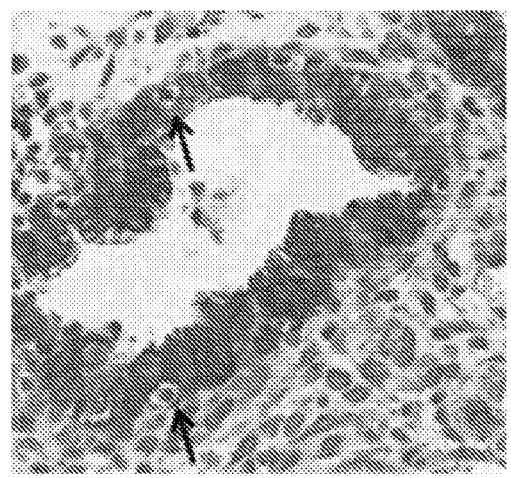
FIG. 3 demonstrates the formation of "stone-like" structures (SLS) in endometriotic lesions. Arrows indicate exemplary SLSs.
Figure 4:
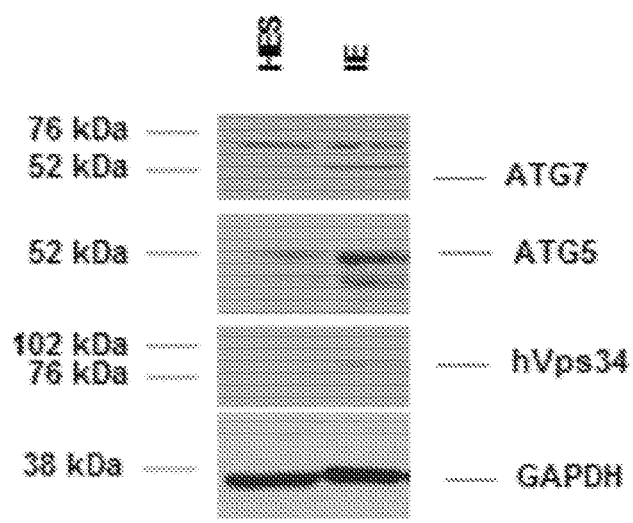
FIG. 4 demonstrates the results from an immunoassay in which protein expression of ATG7, ATG6, hVps34 in normal endometrium cells (HES) and immortalized endometriotic cells (IE) were evaluated. Expression is assessed relative to a GAPDH control.

As shown in FIGS. 1A-1E, the levels of LC3A were assessed using an antibody which detects both the soluble and autophagosomal-bound forms of the LC3A protein. There existed three patterns of LC3A immunoreactivity: (1) diffuse cytoplasmic, (2) cytoplasmic/perinuclear, and (3) "stone-like" structures (SLS) which are round large and densely stained amorphous components enclosed within cytoplasmic vacuoles. High levels of SLS LC3A structures were previously observed to be correlated with tumor aggressiveness and/or disease progression. The intensity of stromal LC3A expression was reduced in the ectopic lesions (ovarian and fallopian) relative to the intensity in the epithelial glands (FIGS. 2A-2B), which displays increased LC3A expression with clear SLS structures (FIG. 3). Furthermore, as presented in FIG. 4, relative to HES (a normal endometrial epithelial cell line), life-extended endometriotic cells (abbreviated "IE") displays increased expression of autophagic markers (i.e. ATG7, ATG5, and hVps34). Collectively, the results suggest that the glandular epithelia of endometriotic lesions have increased LC3-II expression, which can correlate with increased levels of autophagic flux in the epithelium of lesions.

Example 2: Effect of an Autophagic Inhibitor on Life-Extended Endometriotic Cells Life-extended endometriotic (IE) cells were treated with 25 μM chloroquine for up to about 96 hours. Cells were then stained with crystal violet and measured for overall growth at an absorbance of 570 n, using a Bioteck plate reader.

Figure 11:
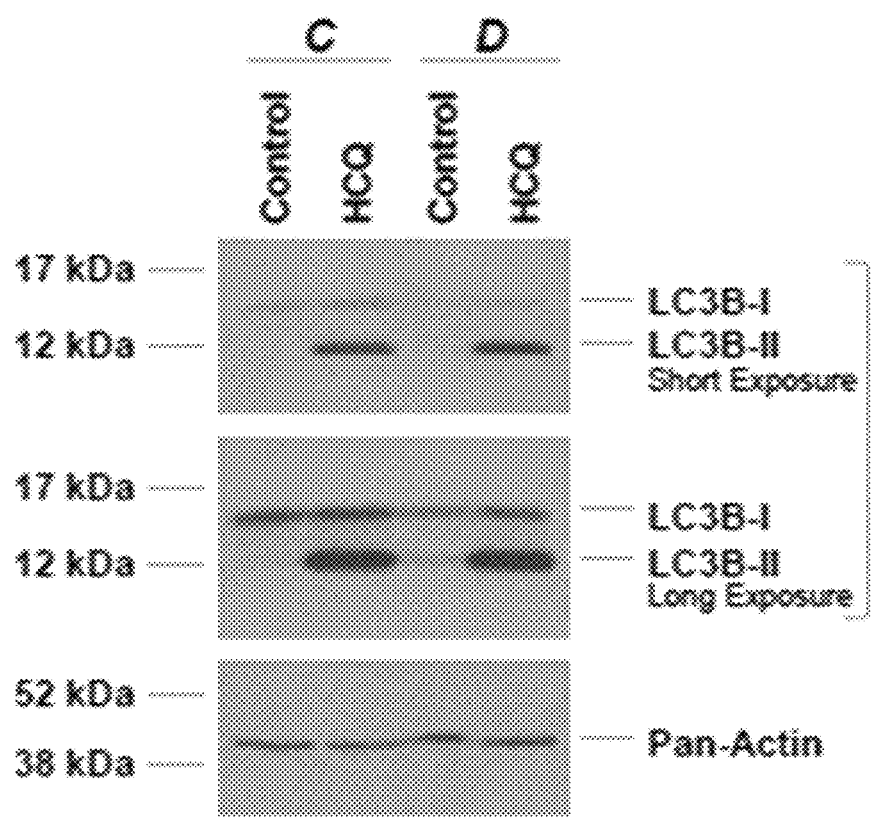
FIG. 11 shows an image of a western blot demonstrating protein content of LC3B-1, LC3B-11, and a control (Pan-Actin) in HCQ or control treated life-extended human endometriotic cells. Life-extended human endometriotic cells were isolated from two different leision types and thus treated separately (C and D).
Figure 12:
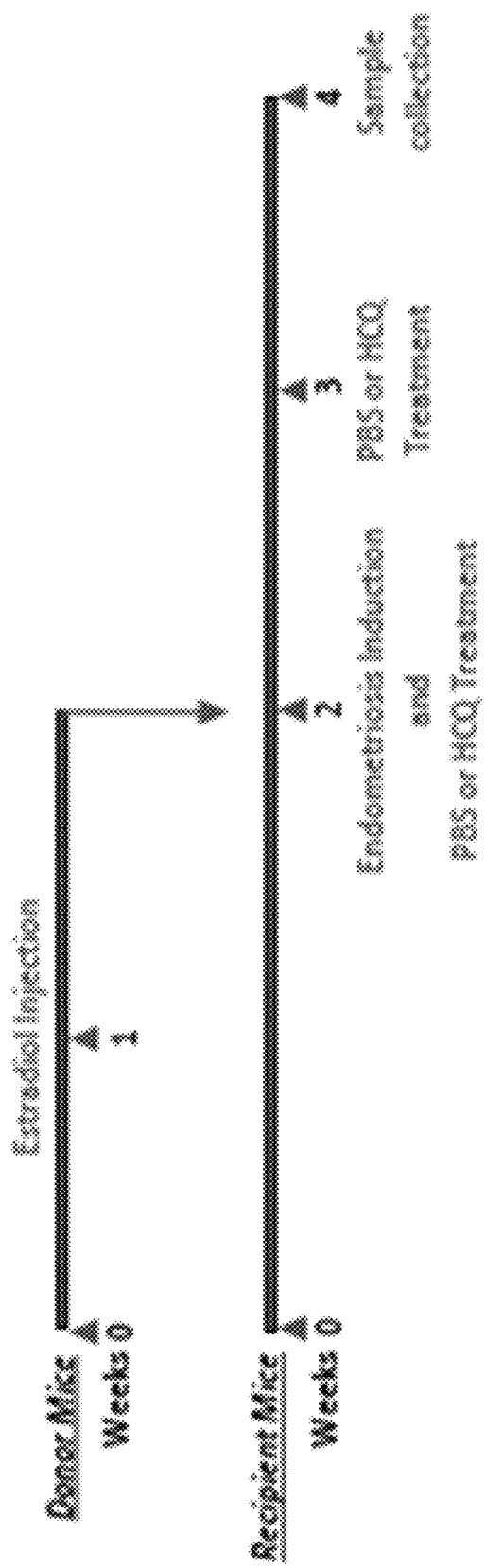
FIG. 12 shows a diagram of a treatment regime for mice to determine the effects of HCQ on endometriotic lesions.

Chloriquine is an inhibitor of autophagic flux, which inhibits the autophagosome-lysosome fusion and likely leads to an accumulation of autophagosomes in the IE cell line. Furthermore, it was observed that cellular survival was dramatically inhibited upon chloroquine (CQ) treatment (FIG. 11). Moreover, it was observed that there was also a marked increase in LC3-II levels (FIG. 12). These results suggest that life-extended endometriotic cells can be "addicted" to autophagy for cellular survival. Cells addicted to autophagy are dependent on autophagy for cell survival. In other words, without autophagy, cells addicted to autophagy succumb to cell death.

Example 3: Effect of Hydroxychloroquine on Endometriosis In Vivo

To determine the effect of hydroxychloroquine on endometriosis in vivo, mice (6-8 week old C57BL/6 background mice) were fed on a mouse diet and given ad libitum access to water and kept on a light/dark cycle of 12/12 h under controlled conditions. Prior to any invasive procedure, the mice were anesthetized using Isofluorane (initial vaporizer flow rate of 3-5%) implemented once prior to an invasive procedure. The mice were also given Ketoprofen (10 mg/kg) subcutaneously as a post-operative analgesic agent for the first 24 hours and then as needed. All surgical procedures were performed under sterile conditions.

Mice were ordered at 3-5 weeks of age to receive them and allow them to acclimate to the housing conditions prior to the start of the investigation when the mice are about 6 to about 8 weeks of age. As endometriosis is an estrogen dependent disease, donor mice were supplemented with estrogens (either in pellet-form or via injection of 17-β-estradiol) to closely represent the in vivo conditions as well as generating a uniform hormone profile in the absence of normal animal cycling. Donor mice used were C57BL/6 mice (wild type) (Jackson laboratories). All recipient mice were in the C57BL/6 genetic background. Donor mice were treated with 17-β-estradiol (estrogen dependency of the growth of endometriotic lesions is a well-known phenomenon). This will be administered 1 week prior to collection of uterine horns and endometrial fragment injection. Estrogen dependency of the growth of endometriotic lesions is a known phenomenon. Following 1 week of estrogen treatment, donor mice were euthanized, uterine horns removed and subdivided into 2 equal fragments that can then be minced and injected into 2 recipient mice as described below. One uterine horn can be injected into 1 recipient mouse, while the other uterine horn can be into the second recipient mouse. In this way, sufficient uterine horn tissue can be collected from a single donor mouse to be subdivided into 2 recipient mice.

Endometrial fragments were obtained by peeling off the serosa and myometrium gently followed by mincing using a razor blade. The fragments were suspended in about 0.6 ml of phosphate buffered saline and were injected with an 18-gauge needle through the abdominal wall below the umbilicus into the peritoneal cavity of recipient mice with a ratio of one donor to two recipients (equivalent quantities). This procedure was performed under anesthetic using Isofluorane (initial vaporizer flow rate of 3-5%) implemented once prior to the invasive procedure as well as Ketoprofen (10 mg/kg) subcutaneously as a post-operative analgesic agent for the first 24 hours and then as needed. All surgical procedures were performed under sterile conditions.

At two weeks post-induction, the lesions were developed and formed cyst-like structures. When the lesions had developed to this point, the mice were euthanized. Lesions were identified, removed, and analyzed.

Figure 5:
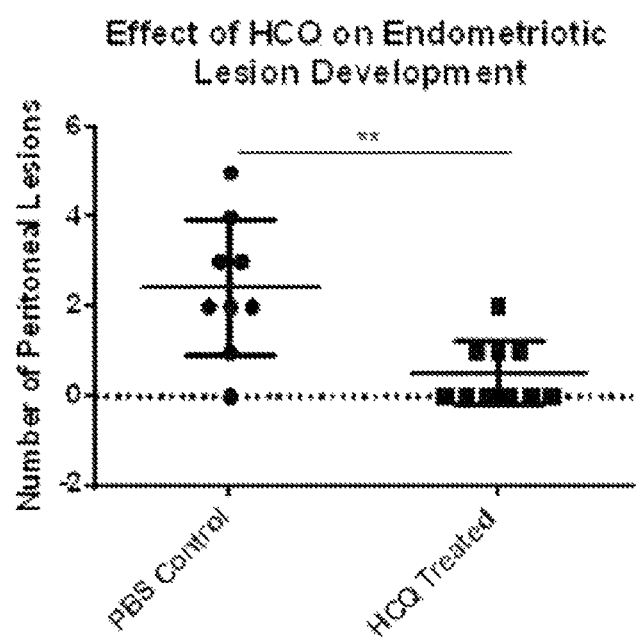
FIG. 5 demonstrates the effect of an autophagic inhibitor on endometriotic cells in vivo. The P value between the two groups was 0.0019.

To assess the effect of hydroxychloroquine on lesion formation, two groups of C57BL/6 mice were used: The first group received daily intraperitoneal injections with hydroxychloroquine at 60 mg/kg in 100 μl of PBS and the second group received 100 μl of PBS and a one-time treatment with hydroxychloroquine (60 mg/kg) ((HCQ) dissolved in PBS) on the day of endometrial fragment implantation. Mice were euthanized for evaluation of lesions on 14 days after the start of treatment. The abdomen was inspected and lesions were excised from surrounding tissue. Results are shown in FIG. 5, which demonstrates the effectiveness of hydroxychlorquine on endometriotic lesions.

Example 4: Development of Life-Extended Endometriotic Cells

Primary endometriotic were maintained in 1:1 mixture of Medium 199 and MCDB131 with 8% setal bovine serum and penicillin/streptomycin along with insulin/transferrin/selenium (ITS) (streptomycin (100 mg/mL; diluted 1:100 in complete culture media), and insulin (5 mg/mL)/transferrin (5 mg/mL)/selenium (5 μg/mL)). SV40 large T antigen was used to immortalize the primary cells. The LargeT antigen pBABE-puro vector was obtained from Addgene. Retroviral particles were generated utilizing HEK293T cells. These cells were transfected with pCGP and pVSVG vector. Collections of retroviral media were collected at 48 h and 72 h post-transfection. These particles were filtered (removal of HEK293T cells) and then used to infect the primary endometriotic cells. After infection, cells were treated with puromycin (2.5 μg/mL) to select for positively infected cells. Six colonies were isolated and were expanded and validated for future use.

Example 5: Characterization of the Life-Extended Endometriotic Cells

Life extended endometriotic cells were characterized prior to (primary Endometrial cells) and after large T antigen expression (life-extended). As demonstrated in FIGS. 6A and 6B Primary endometriotic cells derived from endometrial tissue of a patient having endometriosis (Primary C and D) were compared to endometrioid (TOV112D cells), clear cell ovarian cancer cell line (TOV21G), endometrial adenocarcinoma (MFE 296, MFE319, AN3-CA, KLE, HEC-1A), and serous epithelial ovarian carcinoma cell lines (OVCAR8, HEY, SKOV3) to determine the protein expression patterns (profiles) of tumor promoters (EVI1, RON, EGFR, SnoN, AKT), tumor suppressors (TGFβRII, Smad2/3, PTEN), autophagy markers (ATG5, ATG7, beclin-1, hVps34), epithelial markers (E-cadherin), and Stromal Markers (Ncadherin, vimentin). A normal immortalized ovarian surface epithelia cell (T80) was also evaluated in tandem. Protein expression was evaluated by western blot. All cells evaluated were mycoplasma-negative and STR (short tandem repeat) profiled to validate the cell lines and screen for HeLa cell contamination.

Figure 6A:
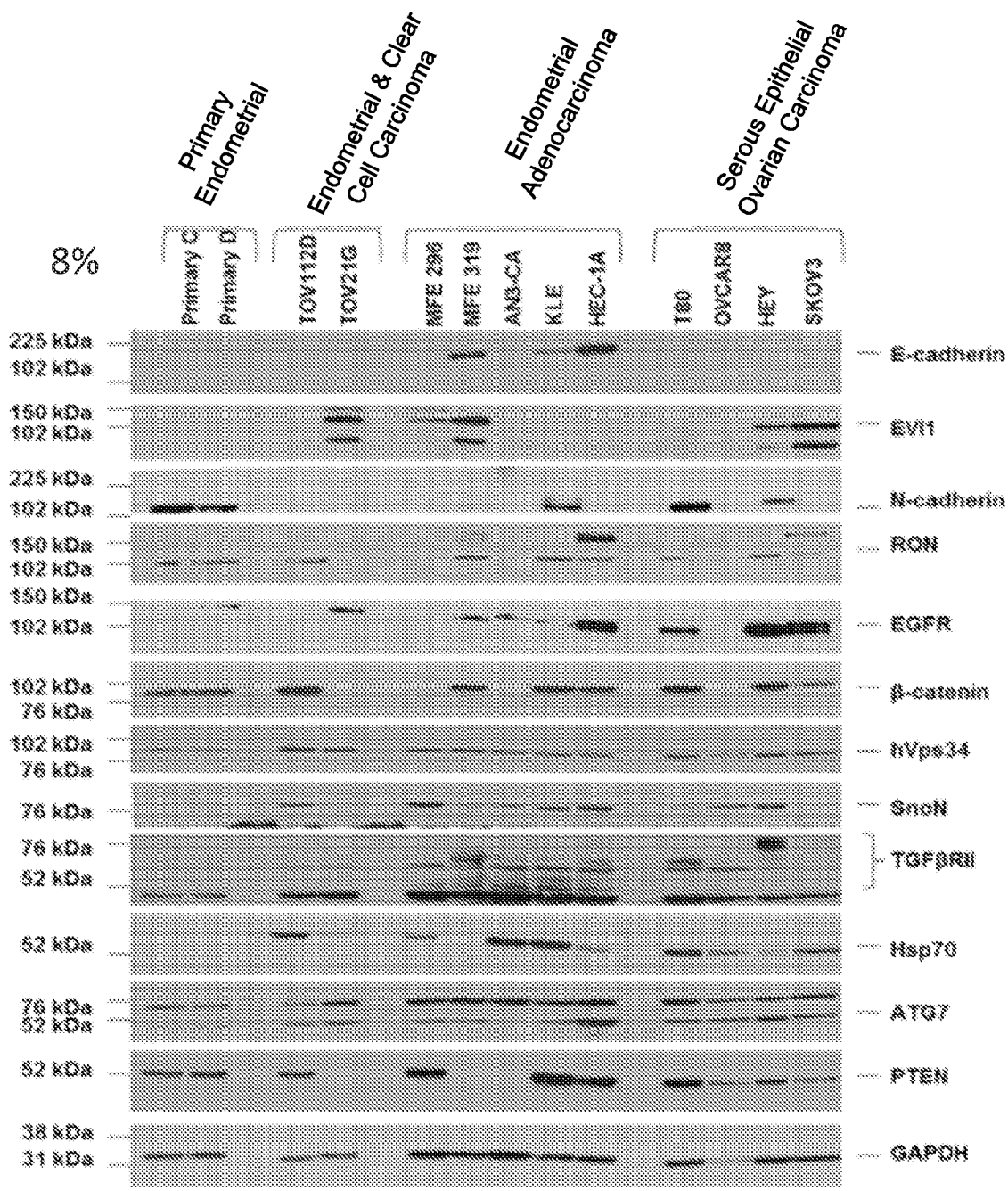
FIGS. 6A and 6B demonstrate the expression of various proteins in primary endometrial cell lines used to develop a life-extended endometrial cell line. Primary endometriotic cells were compared to endometrioid, clear cell, adenocarcinoma, and serous carcinoma cell lines to determine the expression patterns of tumor promoters (EVI1, RON, EGFR, SnoN, AKT), tumor suppressors (TGFβRII, Smad2/3, PTEN), autophagy markers (ATG5, ATG7, beclin-1, hVps34), epithelial markers (E-cadherin), and stromal markers (Ncadherin, vimentin).
Figure 6B:
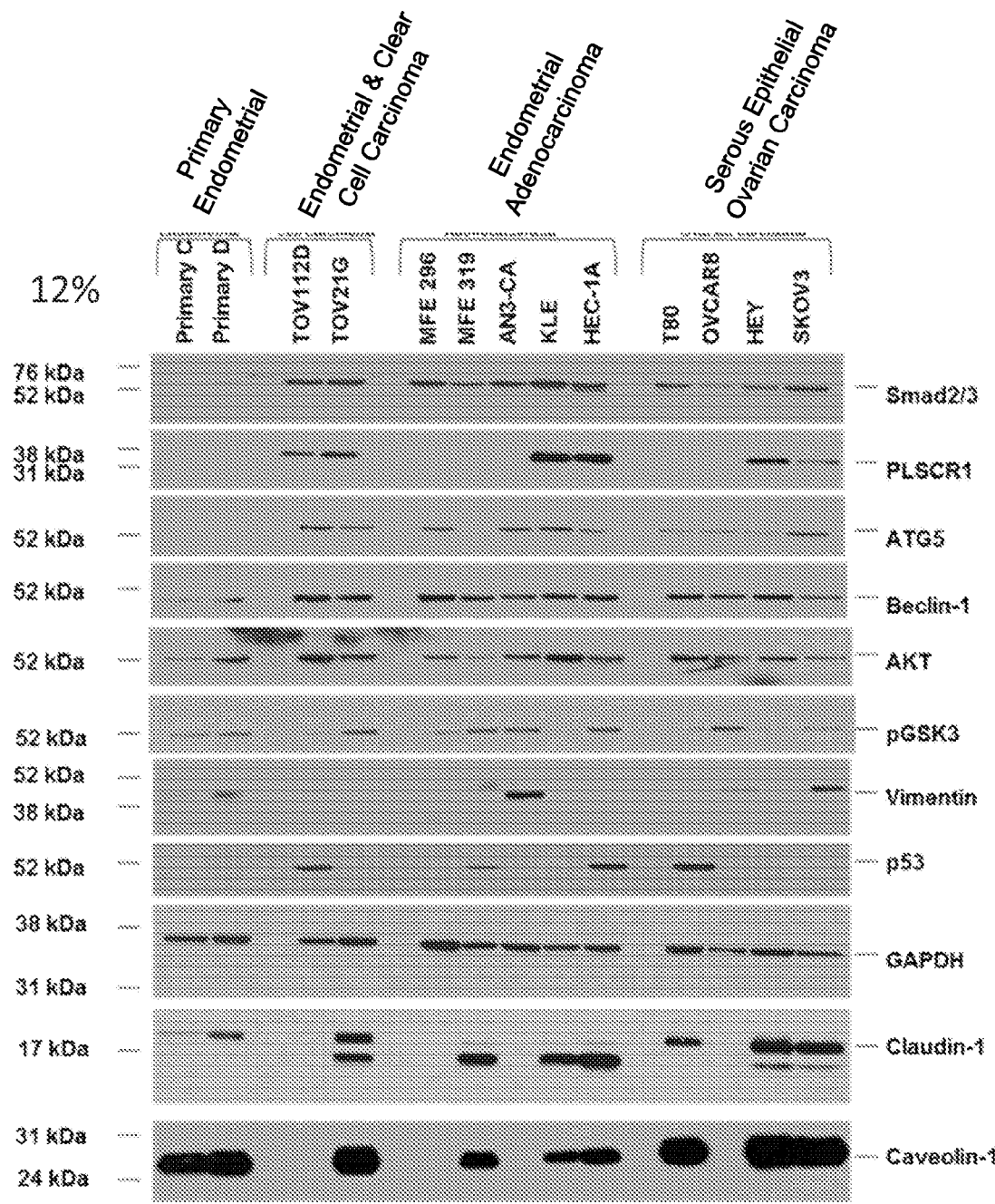

As demonstrated in FIGS. 6A and 6B, the primary cells expressed tumor suppressors PTEN and Smad2/3 with undetectable levels of the tumor promoters EVI1 and SnoN/SkiL. Expression of E-cadherin was not able to be detected expression in both the primary C and D cell lines although a low level of expression of the stromal markers, vimentin and N-cadherin, was observed. These results suggest that the primary cell lines contain characteristics of stromal cells. Indeed, visual observation of the primary cells under the light microscope clearly demonstrated the presence of two distinct cell types, one with honeycomb morphology representative of an epithelial-like endometriotic cell population with another cell type of a more elongated, fibroblast-like morphology. Furthermore, after several passages in culture, the population shifted greatly in favor of the stromal-like morphology suggesting that the stromal-like cell population were capable of outgrowing the slower growing epithelial population (data not shown). In addition, it was observed that the cell line growth capacity slowed markedly after 10 passages in culture, which hindered long-term studies.

Figure 7A:
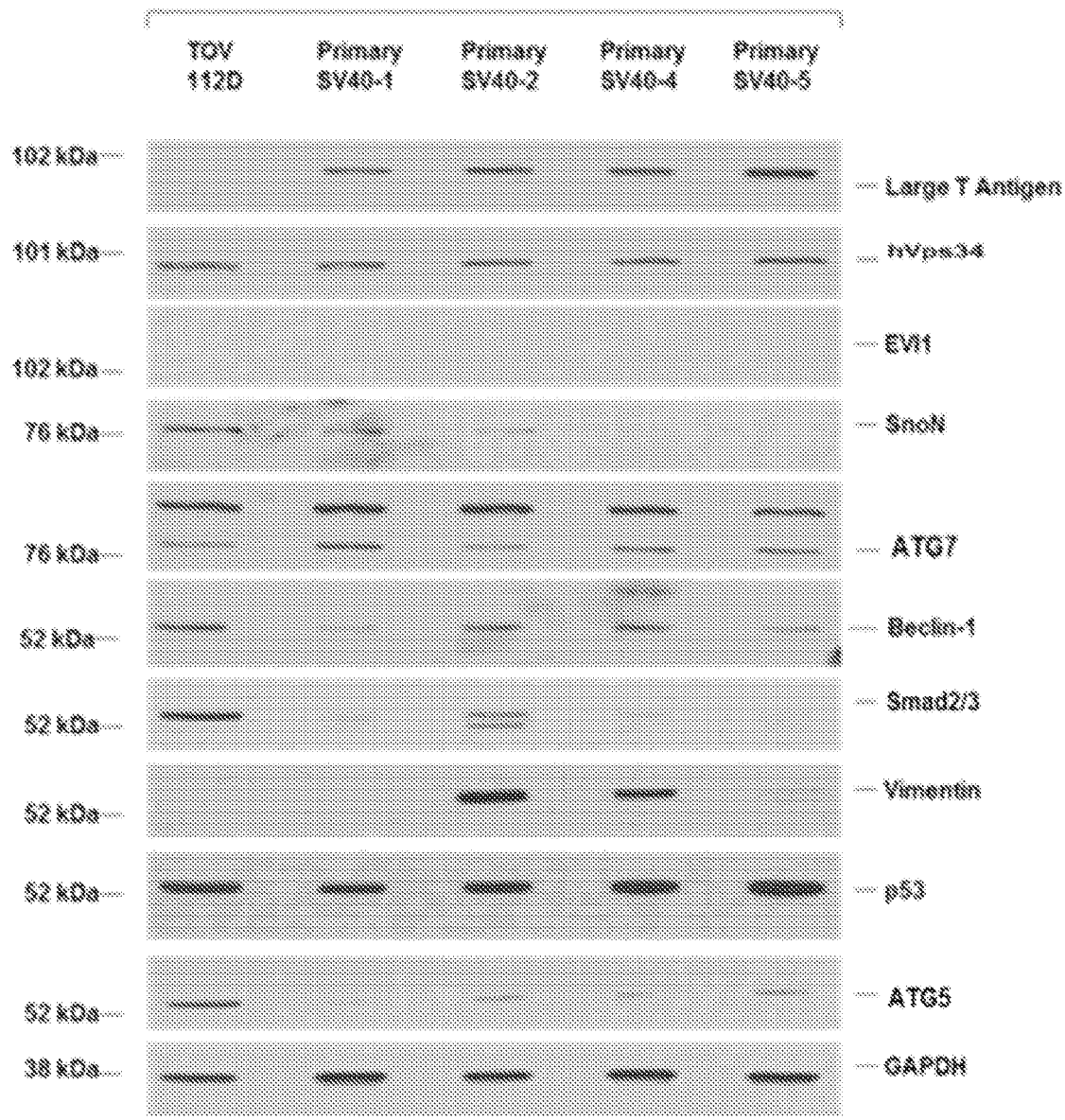
FIGS. 7A and 7B demonstrate expression of various proteins in primary endometrial cells lines used to develop a life-extended endometrial cell line. Primary D endometriotic cells were retrovirally infected with SV40 large T antigen and selected with puromycin. Individual colonies were picked and grown in culture for one month. Lysate was collected from each colony and assessed for expression of large T antigen. Other markers were used to assess change in cell expression due to SV40 large T antigen (EVI1, SnoN, and autophagy markers) as well as confirmation of positive selection of epithelial cells (absence of vimentin). Expression of p53 indicates inactivation via expression of large T antigen.
Figure 7B:
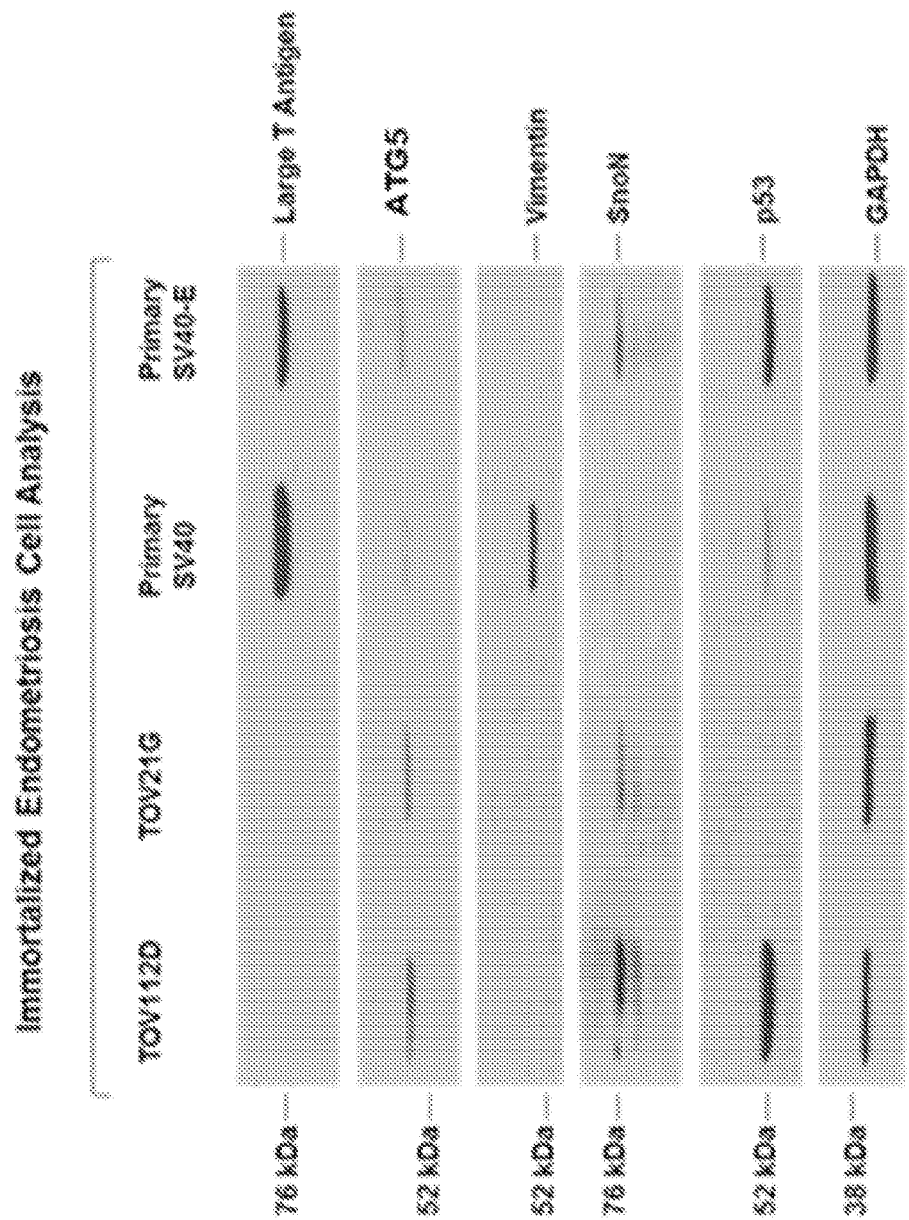

Primary D endometriotic cells were retrovirally infected with SV40 large T antigen and selected with puromycin. Individual colonies were picked and grown in culture for one month. Lysate was collected from each colony and assessed for expression of large T antigen. Other markers were used to assess change in cell expression due to SV40 large T antigen (EVI1, SnoN, and autophagy markers) as well as confirmation of positive selection of epithelial cells (absence of vimentin). Expression of p53 indicates inactivation via expression of large T antigen. The results of the protein expression analysis in these cells are shown in FIGS. 7A and 7B. Confirmation of the absence of vimentin and presence of cytokeratin-18 (Cy3) (epithelial marker) was performed via immunofluorescence. T80 cells serve as a positive control for Cy3 and SKOV3 a positive control for vimentin. These results are shown in FIGS. 8A-8L.

A decreased expression of the stromal marker vimentin (relative to primary cells) was observed (FIGS. 7A and 7B) in the life-extended cells (IE), which suggests the successful selection of the epithelial-like population of endometriotic cells. The epithelial nature of the selected populations was confirmed via immunofluorescence staining for cytokeratin-18 (an epithelial marker) and vimentin (a mesenchymal marker) (FIGS. 8A-8L). T80 cells were utilized as a positive control for cytokeratin-18 and a negative control for vimentin. SKOV3 ovarian cancer cells were utilized as a positive control for vimentin and cytokeratin-18. These results suggest that endometriotic SV40 large T antigen expressing cells had strong expression of cytokeratin-18 with undetectable expression of vimentin.

As demonstrated in FIGS. 7A and 7B, stable expression of SV40 Large T antigen does not significantly alter the protein expression of EVI1 and SnoN (tumor promoting singals), Smad2/3 (tumor suppressor), ATG7, ATG5, beclin-1, and hVps34 (autophagy markers) as compared to primary endomtriotic cells that do not express the SV40 large T antigen. As compared to clear cell ovarian cancer (TOV21G) and endometrioid ovarian cancer (TOV112D). The only observed difference in expression between these lines and the life-extended (IE) cells and these lines was the observed increase in p53. This increase could be due to the role of large T antigen in inactivating p53, which could result in an inability of p53 to turnover.

The life extended endometrial cells generated from transforming primary endometrial cells with SV40 Large T antigen (IE cells) were observed to have a unique STR profile. As Ras and PIK3CA are considered important mediators in the transition from endometriosis to clear cell ovarian cancer, the mutational status of the genes in the life extended (IE) cells was assessed. Briefly, genomic DNA from IE cells was isolated and primers for PIK3CA (specifically at exons 9 and 20) as well as K-Ras (specific for the GTP binding site) were synthesized and utilized for sequencing. Their sequences were compared to the normal sequence expression derived from T80 parental cells to confirm no mutations were present. In determine if the IE cells lack markers of other potentially contaminating cell types, genomic DNA from the IE cells was isolated and a short tandem repeat (STR) profiling analysis (via Genetica Laboratories) was completed. STR is the analysis of repeated segments of DNA (roughly 2-6 base pairs) spread through the genome. In brief, Genetica provides a highly sensitive DNA screen of the cell lines provided and compares them with available data bases. The service is useful for both human and mouse cell types and allows for certainty of cross contamination down to 5% of the DNA. The assessment included a survey of a database of cell lines including cells from ATCC. The analysis indicated that the IE cells were unique in origin from any other cell type in the databases available to Genetica.

Example 6

Abbreviations:

ATG, autophagy-related gene; BNIP3, BCL2/Adenovirus E1B 19 kDa Interacting Protein; CK8, cytokeratin 8; EIF2AK3, eukaryotic translation initiation factor 2-alpha kinase 3; ERα, estrogen receptor alpha; FBS, Fetal Bovine Serum; GABARAPL1, GABA(A) receptor-associated protein like 1; G-CSF, granulocyte colony-stimulating factor; GI, gastrointestinal tract; HCQ, hydroxychloroquine; IGF1, insulin-like growth factor 1; IP-10, 10 kDa interferon gamma-induced protein; IRGM1, immunity-related GTPase family M1; ITS, insulin transferrin selenium; LC3B, microtubule-associated protein 1 light chain 3 beta; PE, phosphatidylethanolamine; PIK3C3, phosphatidylinositol 3-kinase, catalytic subunit type 3; PBS, phosphate buffered saline; PRKAA1, AMP-activated, alpha 1 catalytic subunit; PR, progesterone receptor; PTEN, phosphatase and tensin homolog; SQSTM1, Sequestosome 1; STR, short tandem repeat; SV40, simian virus 40; TEM, transmission electron microscopy; TMA, tissue microarray; ULK1, unc-51 like autophagy activating kinase 1.

Introduction:

Endometriosis is a chronic, painful, and debilitating disease in which endometrium-like glandular and stromal cells grow outside the uterine cavity.[1, 2] It is an inflammatory and estrogen-dependent disease that affects 6-10% of women during their reproductive years and up to 50% of women receiving fertility treatments. [3] Sampson's hypothesis (the most accepted theory) states that shed endometrial tissue during menses reaches the peritoneal cavity by exiting the uterus through the fallopian tubes by retrograde menstruation. [4-6] These shed endometrial cells survive, implant, and grow at ectopic locations, developing into endometriotic lesions. [5, 7]

Epithelial cells normally undergo anoikis, a mechanism of programmed cell death, upon detachment from the extracellular matrix. [8] Without being bound to theory, autophagy could potentially alter the anoikis response in endometrial cells. This cellular pathway is involved in cellular homeostasis. [9, 10] Under conditions of stress, changes in autophagic flux can lead to altered cellular survival. [9, 10] Autophagy is a complex process that begins with the formation of double-membrane vesicles, termed autophagosomes, which engulf cytoplasmic components. Briefly, autophagosomes fuse with lysosomes to degrade and recycle their cargo comprised of oxidized proteins, lipids, and damaged organelles. Presently, there is limited evidence that autophagy contributes to the development and progression of endometriosis. In a surgical induction model of murine endometriosis, increased expression of ATG9A, an autophagic mediator that is involved in vesicle formation [11], was detected in the eutopic endometria from endometriosis-induced mice. [12] In human endometriomas (ovarian endometriosis), there was a reduction of LC3-II (the conjugated form of LC3) protein compared to control eutopic endometrial tissue. [13] In contrast, an independent study reported that the protein expression of LC3-II was elevated while p62 (which binds ubiquitinated cargo for degradation) was decreased in ovarian endometriomas compared to eutopic endometria of disease-free participants. [14]

This Example evaluates the therapeutic effects of a lysosomotropic and autophagic flux inhibitor, hydroxychloroquine (HCQ), [15-17] on human endometriotic cells and in an established mouse model of endometriosis. The results demonstrate a non-hormonal treatment for this still incurable and common disease.

Results:

Hydroxychloroquine Alters Human Endometrial and Endometriotic Cell Survival as Well as Lesion Number and Histopathology in a Mouse Model of Endometriosis.

Figure 37:
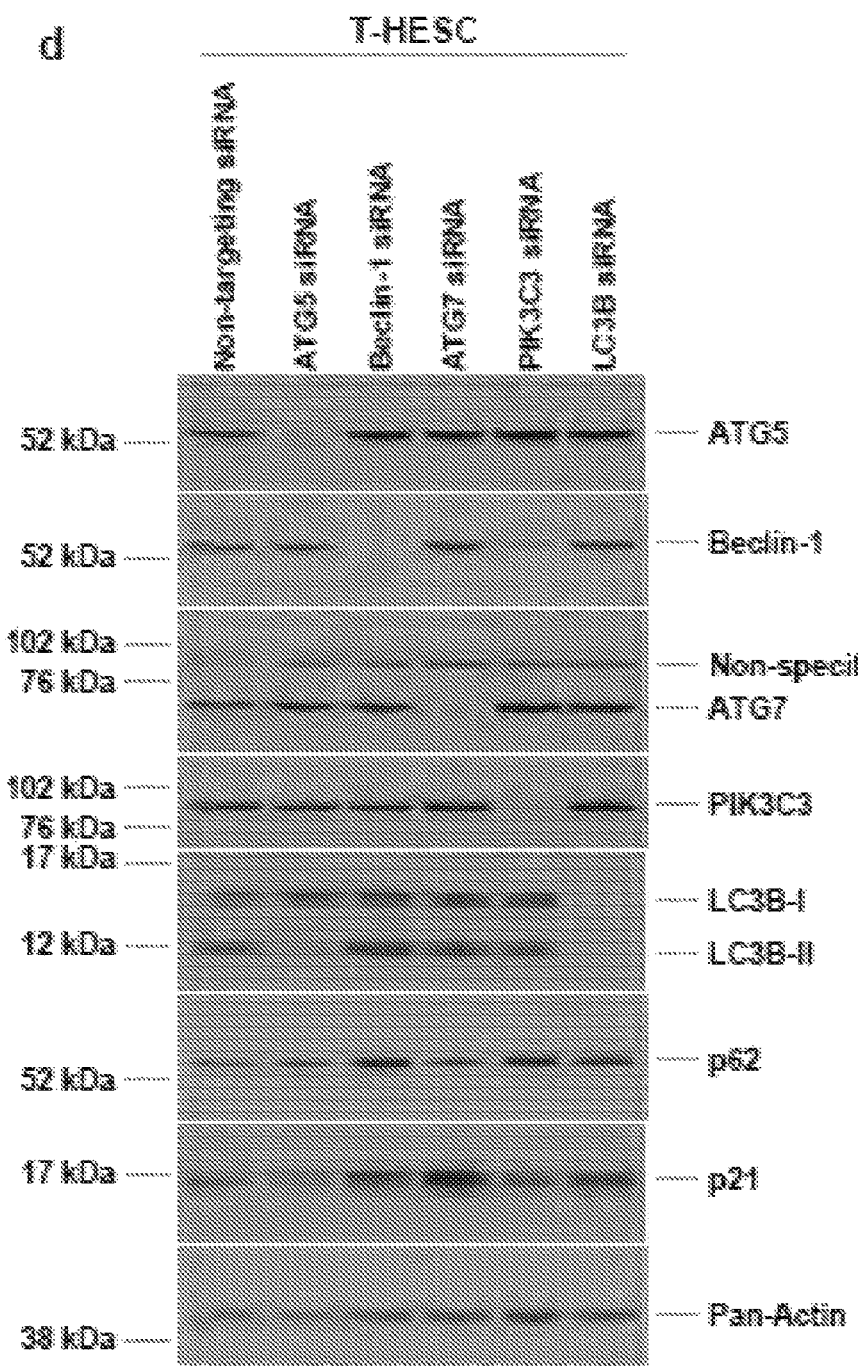
FIG. 37 shows an image of a representative western blot demonstrating the protein expression various autophagic markers and Pan-actin in T-HESC cells treated with various siRNAs.
Figure 38:
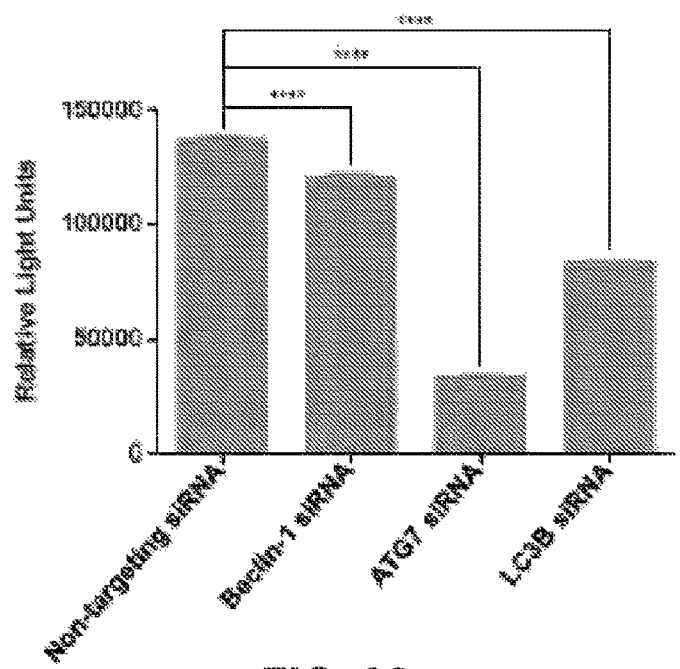
FIG. 38 shows a graph demonstrating cell survival (as expressed as relative light units) of T-HESC cells after being treated with various siRNAs.

To assess whether an autophagic flux inhibitor could alter the survival capacity of cells isolated from human endometriotic lesions, we treated life-extended human endometriotic cells (isolated from two individual patients derived from different types of lesions and thus were tested separately) with 25 µM hydroxychloroquine (HCQ). This dose was selected based on our previous studies. [18] As shown in FIGS. 9A and 9B, a marked reduction was observed in cell survival of human endometriotic cells from two different types of lesions ($p<0.0001$) following 5 days of HCQ treatment. To validate the activity of HCQ, a western blot analysis for LC3B was performed, which showed that LC3B-II increased with HCQ treatment in these human endometriotic cells (FIG. 9C). A similar reduction in cell survival and increase in LC3B-II protein was noted in the T-HESC human endometrial stromal cells (derived from myoma, FIGS. 37-38). To confirm the effect of autophagy inhibition, we performed siRNA knockdown for ATG5, beclin-1, ATG7, PIK3C3, and LC3B in human endometrial and endometriotic cells. Greater than 90% knockdown efficiency of the above described autophagic mediators in T-HESC cells was achieved (FIG. 37). Protein levels of p21 (a cyclin-dependent kinase inhibitor involved in cell cycle arrest) increased with siRNA targeting beclin-1, ATG7, and LC3B. Therefore, these autophagic mediators were investigated to evaluate their effects on cell viability using the CellTiter-glo assay in these cells. As shown in FIG. 38, the cell viability of T-HESC was significantly reduced in all of these knockdown conditions, particularly with ATG7. Without being bound to theory these observations suggest that the use of HCQ (or targeting autophagic mediators) can be detrimental to both human endometrial and endometriotic cell survival.

Figure 13:
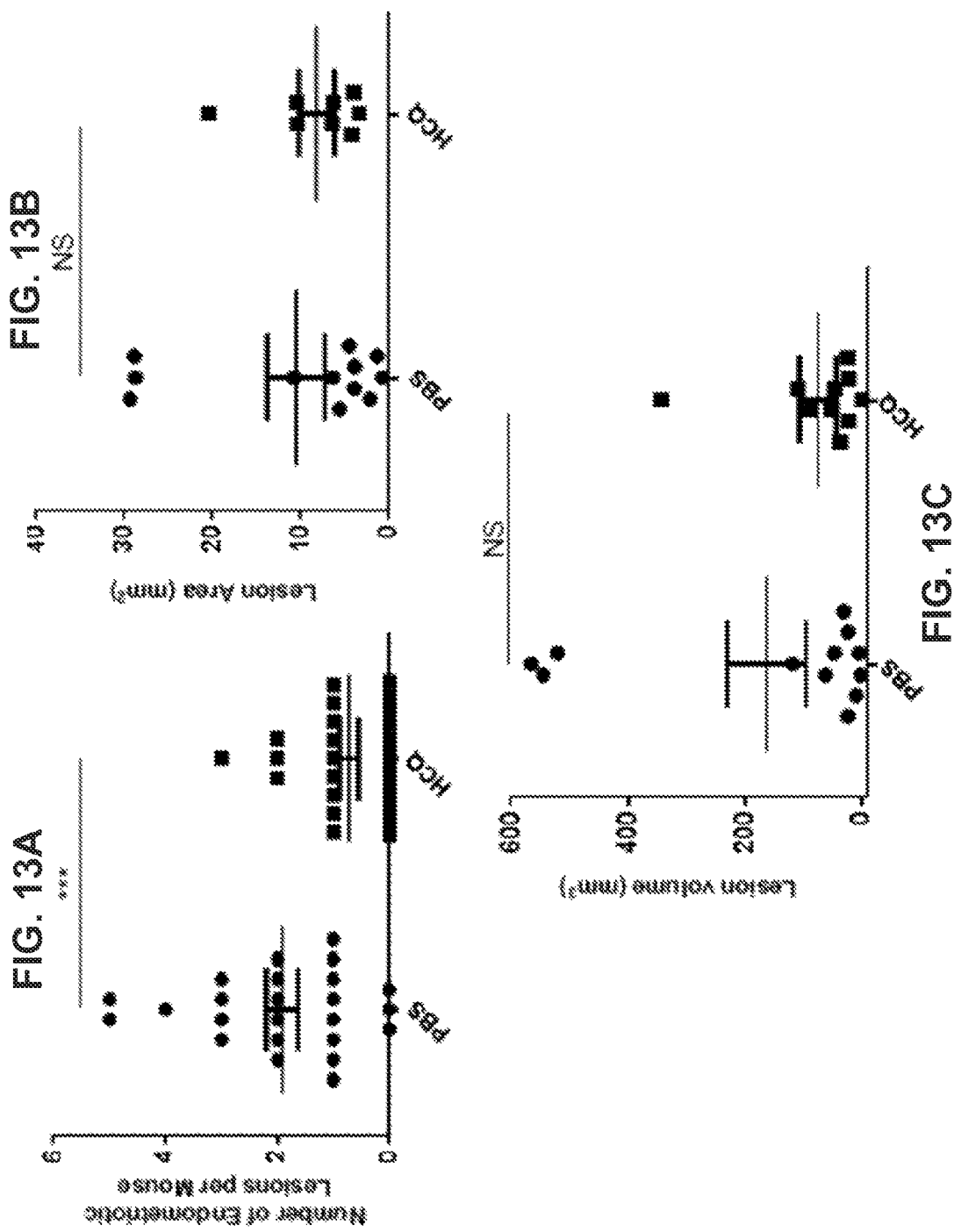
FIGS. 13A-13C show graphs demonstrating the number of endometriotic lesions per mouse (FIG. 13A), lesion area ($mm^2$) and lesion volume ($mm^3$) in mice treated with a control (PBS) or HCQ as set forth in FIG. 12.
Figure 14:
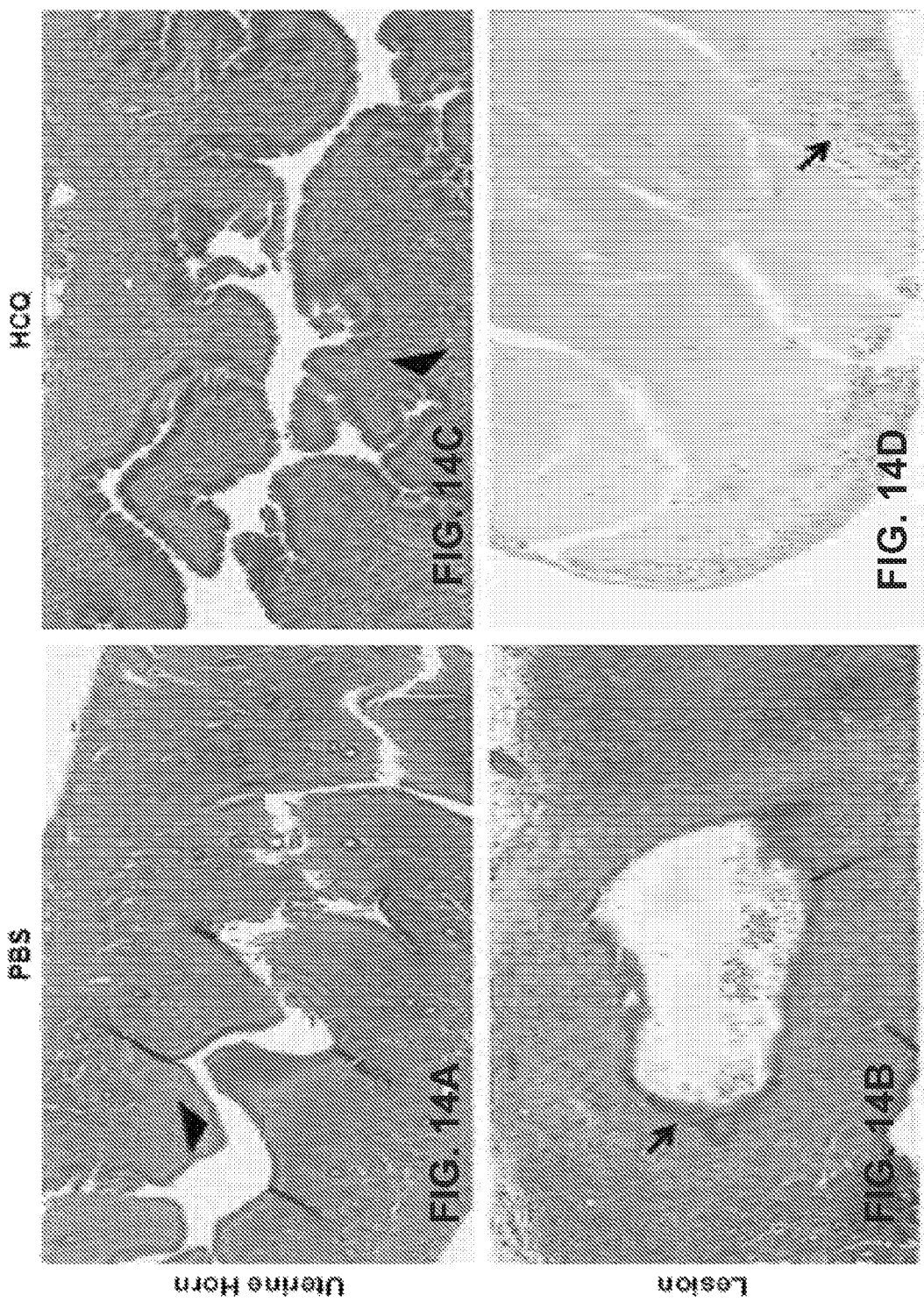
FIGS. 14A-14D show representative hematoxylin and eosin (H&E) stained tissue images of uterine horn tissue (FIGS. 14A and 14C) and lesion tissue (FIGS. 14B and 14D) in control (PBS) and HCQ treated mice treated according to the regimine set forth in FIG. 12. Black arrowheads indicated glandular compartments and plack arrows indicate epithelial cells within the lesions (p=0.03, per Fisher's exact test).
Figure 39:
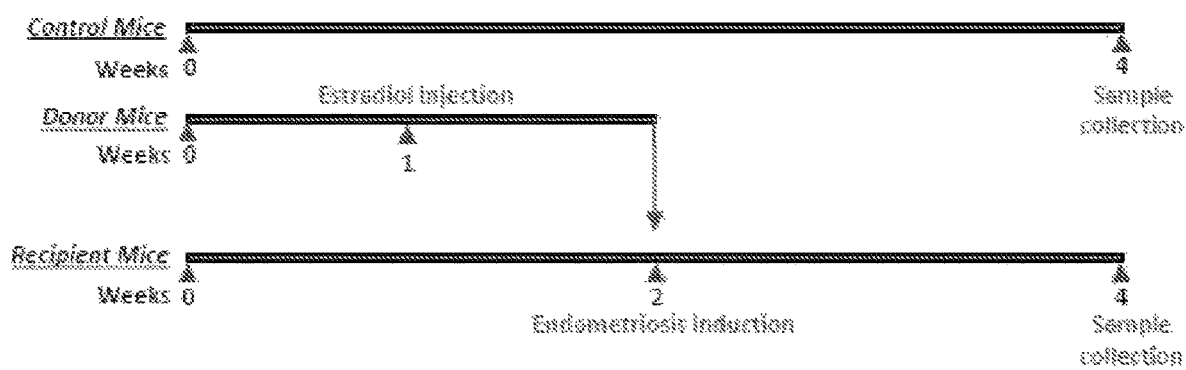
FIG. 39 shows a diagram demonstrating a treatment regine and sample collection time line.
Figure 40:
FIGS. 40A-40B show representative images of control (non-injected mice) or recipient mice. The white arrow indicates ectopic lesions. Mice were treated as set forth in FIG. 39.
Figure 41:
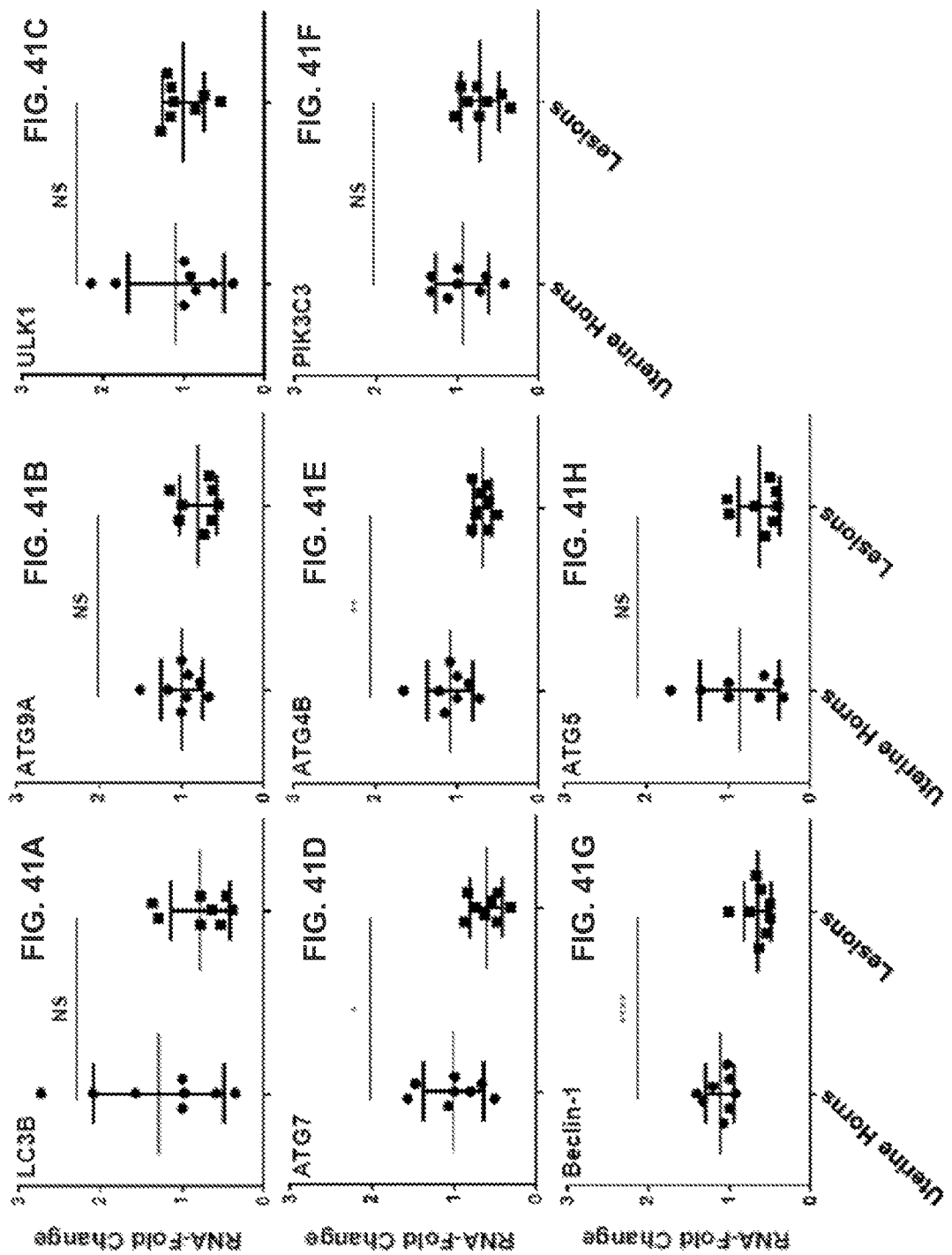
FIGS. 41A-41H show graphs demonstrating mRNA expression (expressed as Fold-change) of various autophagic markers in the uterine horns and lesions in the same recipient mouse. ● indicates individual reps of uterine horns from recipient mice, ■ indicates individual reps of lesions from the same recipient mice

To determine whether treatment with HCQ alters the formation of endometriotic lesions, an induced model of murine endometriosis in which mice receive injections of uterine horn fragments that develop into lesions within 2 weeks was utilized. [19, 20] Receipient (endometriosis-induced) mice were treated with 60 mg/kg HCQ21 or phosphate-buffered saline (PBS, FIG. 12). This treatment was repeated once every seven days post-induction. Mice that were neither injected with uterine horn fragments nor treated were used as controls (FIG. 39). All of the mice were euthanized at the same time (14 days after endometriosis induction for both the PBS and HCQ treatment groups). Ectopic lesions that developed in the recipient mice (white arrow, FIGS. 40A-40B) were counted, measured, and collected for RNA and protein analysis, as well as for histological staining. No lesions were observed in the control group (labeled as N, FIGS. 40A-40B). The majority (87.5%) of endometriosis-induced mice developed lesions. At the time of collection, we noted that the endometriotic lesions varied in size, color, and location across the treatment groups. As shown in FIGS. 13A-13C, there was a significant reduction in the number of lesions that developed in mice treated with HCQ compared to those treated with PBS ($p=0.0007$; PBS-treated mice, n=24 [with a total of 46 lesions] and HCQ-treated mice, n=25 [with a total of 18 lesions]).

A randomly selected subset of the collected lesions and uterine horns were processed for staining with hematoxylin and eosin (H&E) (pathologically confirmed endometriotic lesions from PBS and HCQ-treated mice, n=15 each; uterine horns derived from PBS-treated mice, n=10; and uterine horns derived from HCQ-treated mice, n=10). Interestingly, as shown in FIGS. 14A-14D, an irregular epithelium pattern was observed in 5 out of 10 uterine horns derived from HCQ-treated mice compared to those derived from PBS-treated mice. In addition, we noted that the ectopic growths from HCQ-treated mice did not histologically resemble endometriotic lesions (i.e., did not contain the expected glandular components) while those treated with PBS did (FIGS. 14A-14D, black arrowheads indicate glandular compartments while black arrows indicate epithelial cells within the lesions) ($p=0.03$, per Fisher's exact test). Together, these results demonstrate that HCQ reduces the number of endometriotic lesions and alters the cellular organization within these tissues.

Altered Levels of Peritoneal Macrophages and IP-10 Cytokine from HCQ-Treated Mice.

Figure 15:
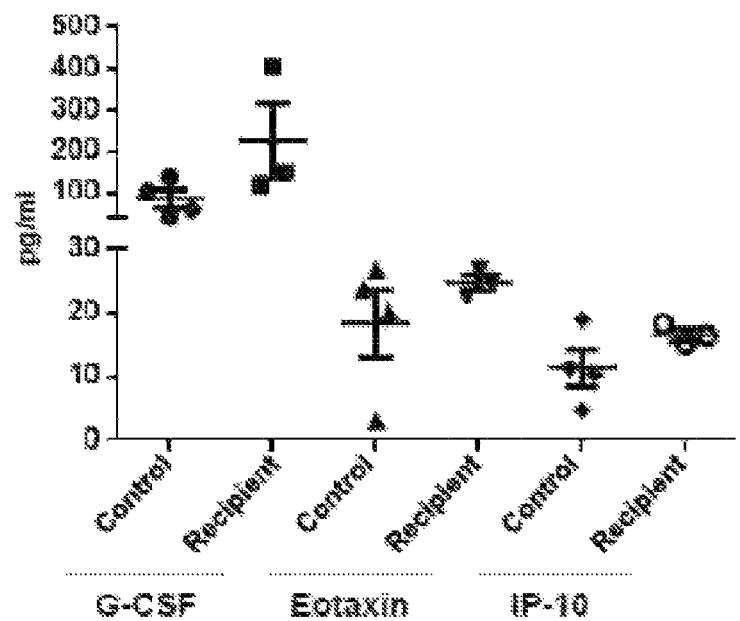
FIG. 15 shows a graph demonstrating the amount of the cytokines/chemokines G-CSF, eotaxin, and IP-10 (in pg/mL) present in the peritoneal fluid collected from control mice and recipient mice using a mouse cytokine and cehmokine magnetic bead panel assay.
Figure 16:
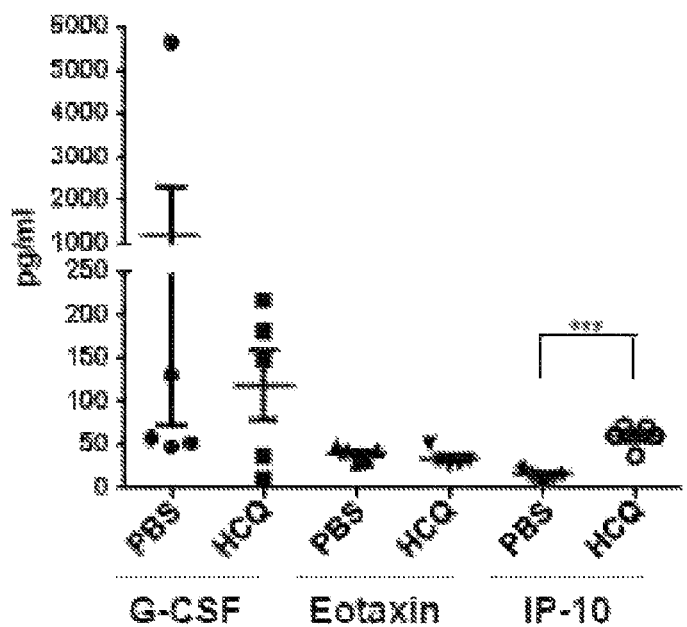
FIG. 16 shows a graph demonstrating the amount of the cytokines/chemokines G-CSF, eotaxin, and IP-10 (in pg/mL) present in the peritoneal fluid collected from control (PBS) treated mice and HCQ treated mice using a mouse cytokine and cehmokine magnetic bead panel assay.

To investigate changes in the inflammatory response to endometriosis, 32 cytokines/chemokines were quantified in the peritoneal fluid collected from control (n=4) and recipient (n=3) mice using a mouse cytokine and chemokine magnetic bead panel assay. Of the 32 analyzed cytokines/chemokines, it was identified that G-CSF, eotaxin, and IP-10 (also known as CXCL10) were within the sensitivity and detection limits of the assay. FIG. 15. In contrast, it was identified that IP-10 was significantly increased ($p=0.0079$) in peritoneal fluid obtained from HCQ-treated mice (n=5) compared to PBS-treated mice (n=5) while G-CSF and eotaxin remained unchanged (FIG. 16).

Figure 17A:
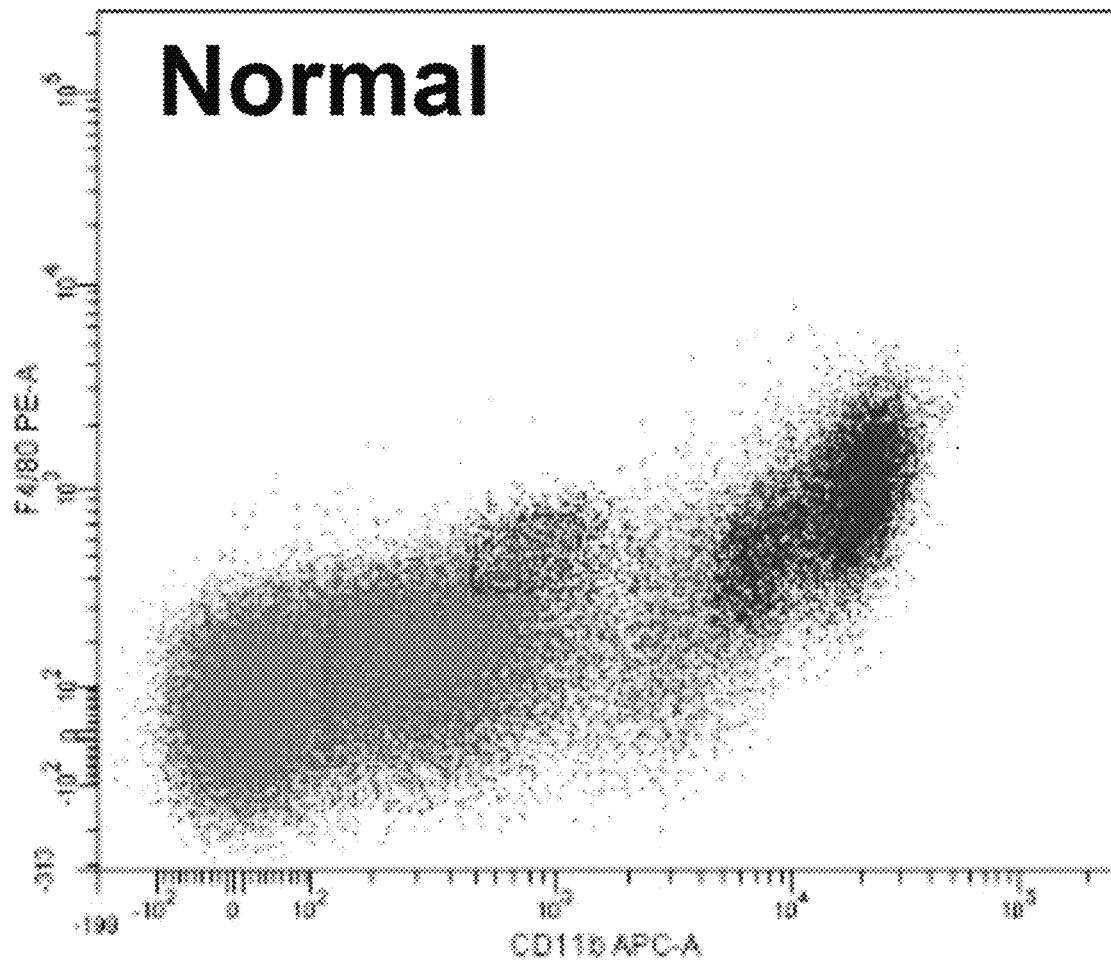
FIGS. 17A-17C demonstrate macrophages in the peritoneal cavity of control and endometriosis-induced mice at the time of sample collection (2-weeks post induction of endometriosis).
Figure 17B:
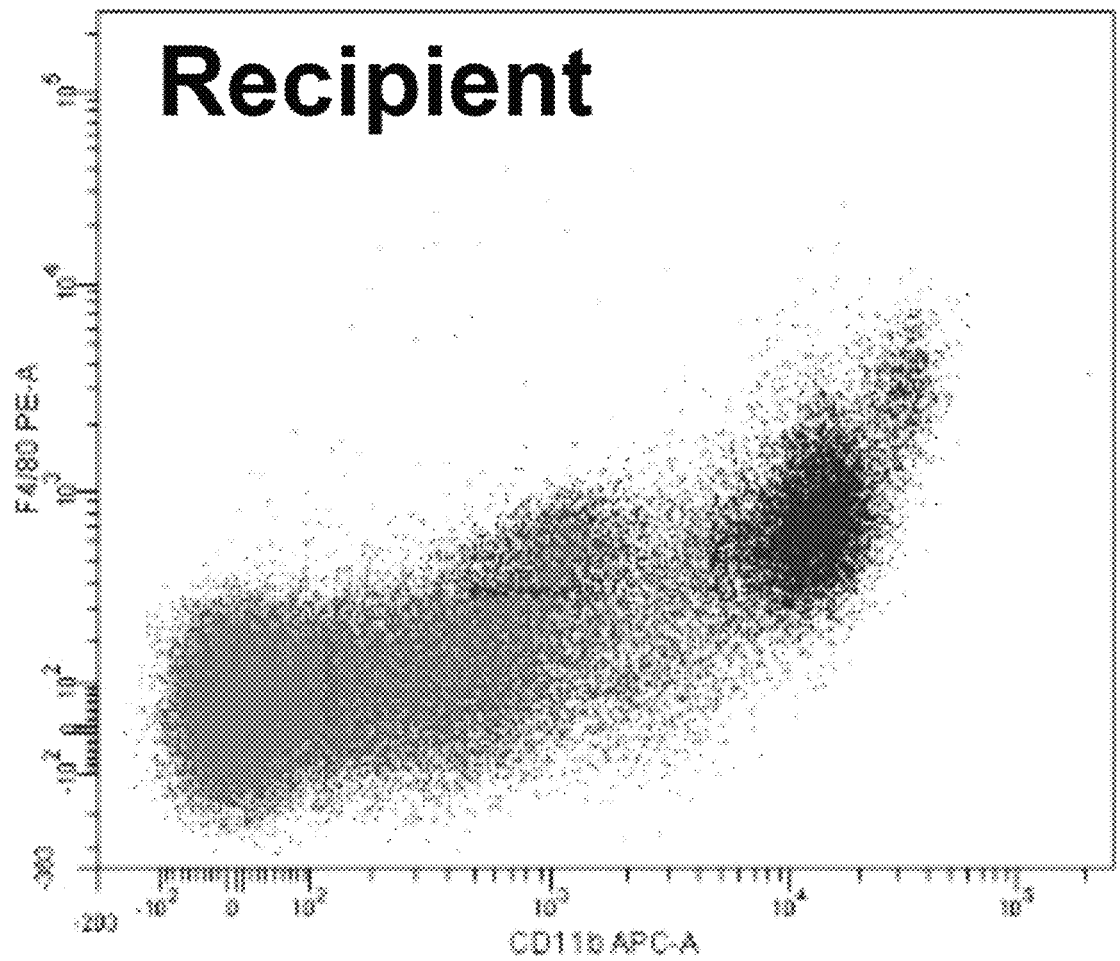
Figure 17C:
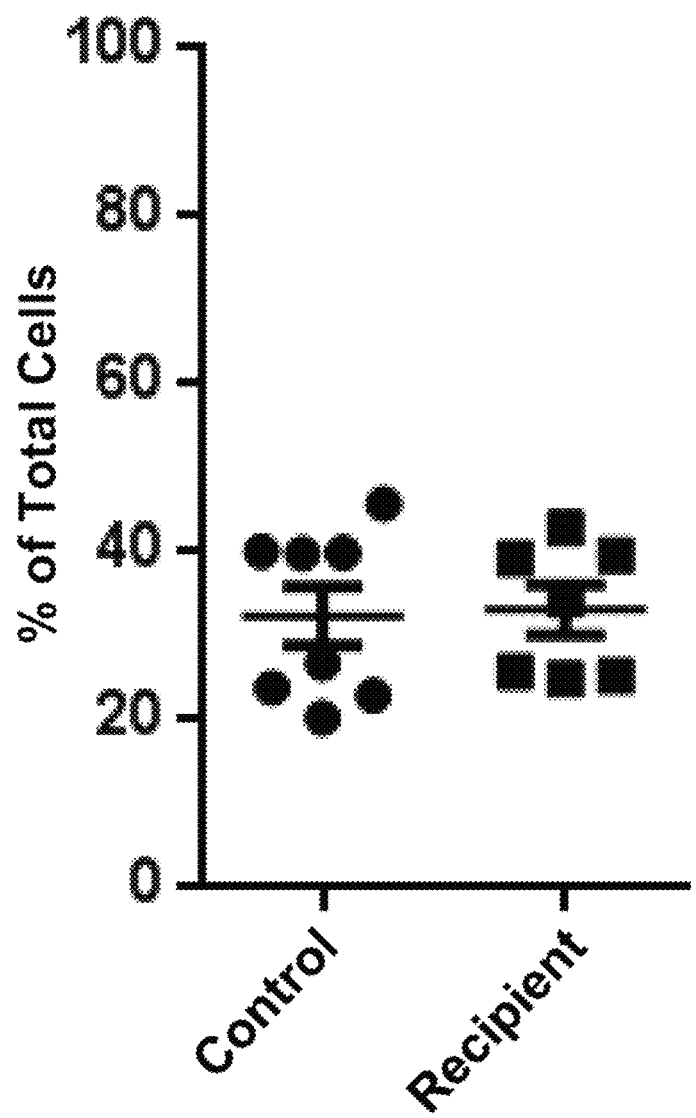
Figure 18A:
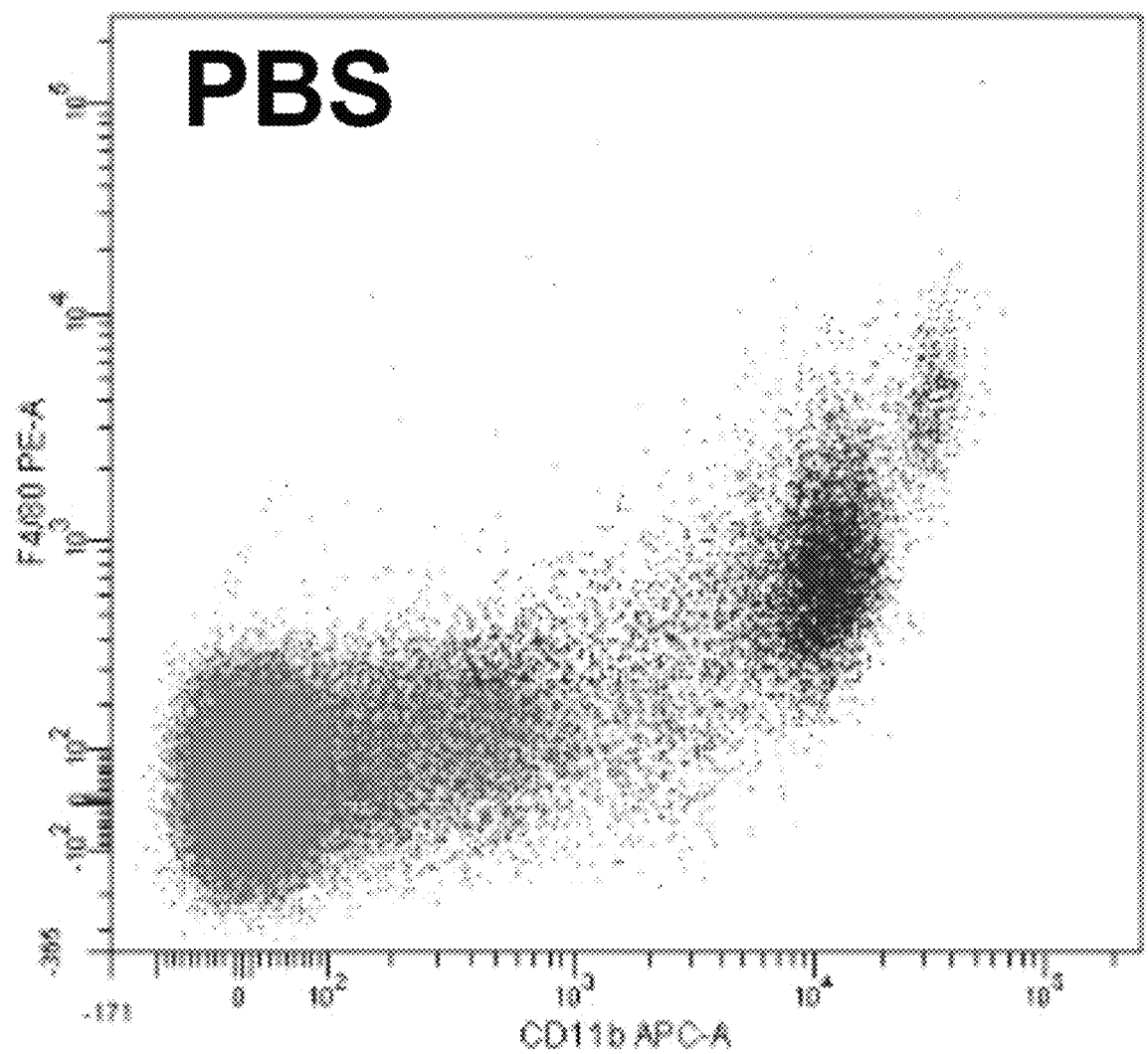
FIGS. 18A-18C demonstrate macrophages in the peritoneal cavity of control (PBS) treated and HCQ treated mice at the time of sample collection (2-weeks post induction of endometriosis).
Figure 18B:
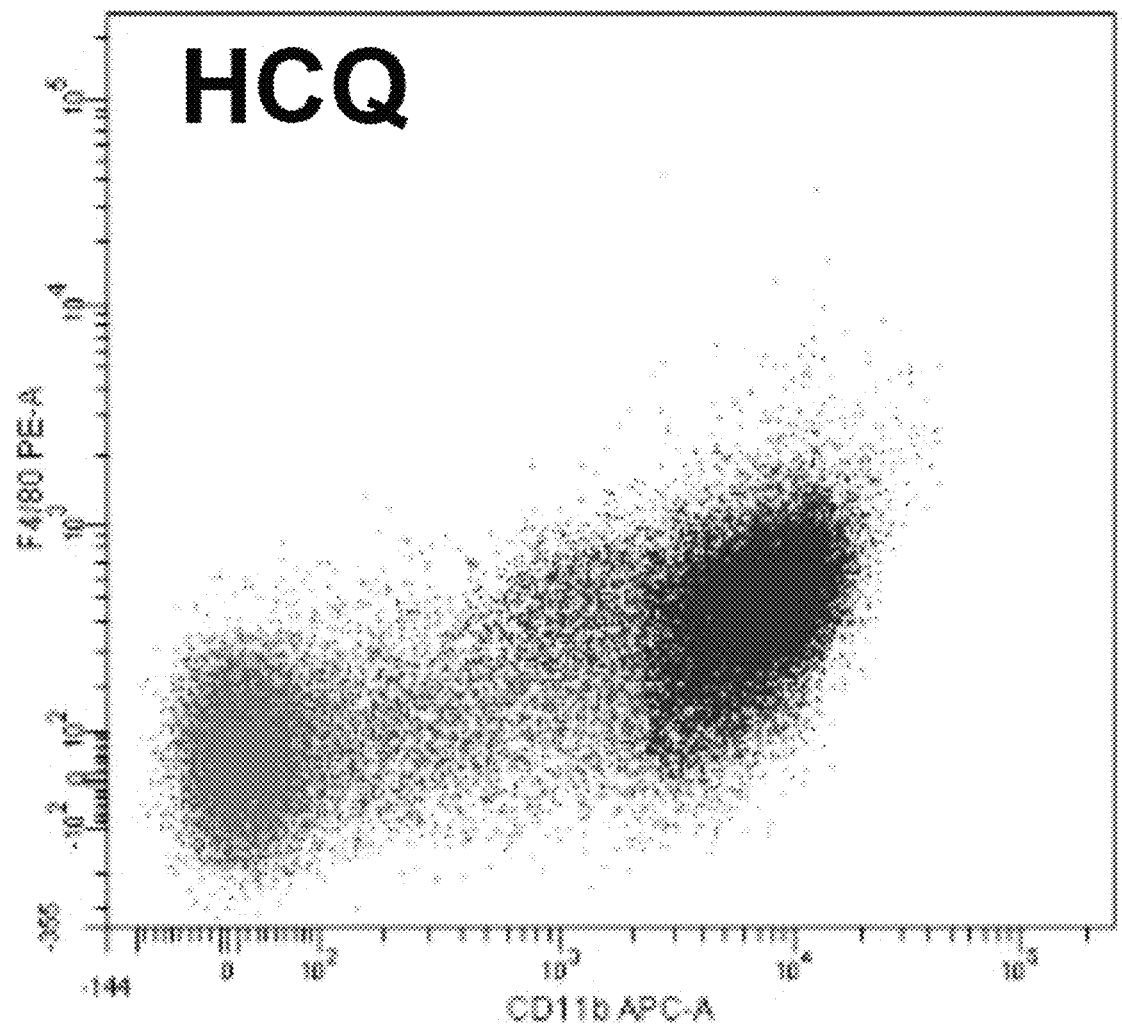
Figure 18C:
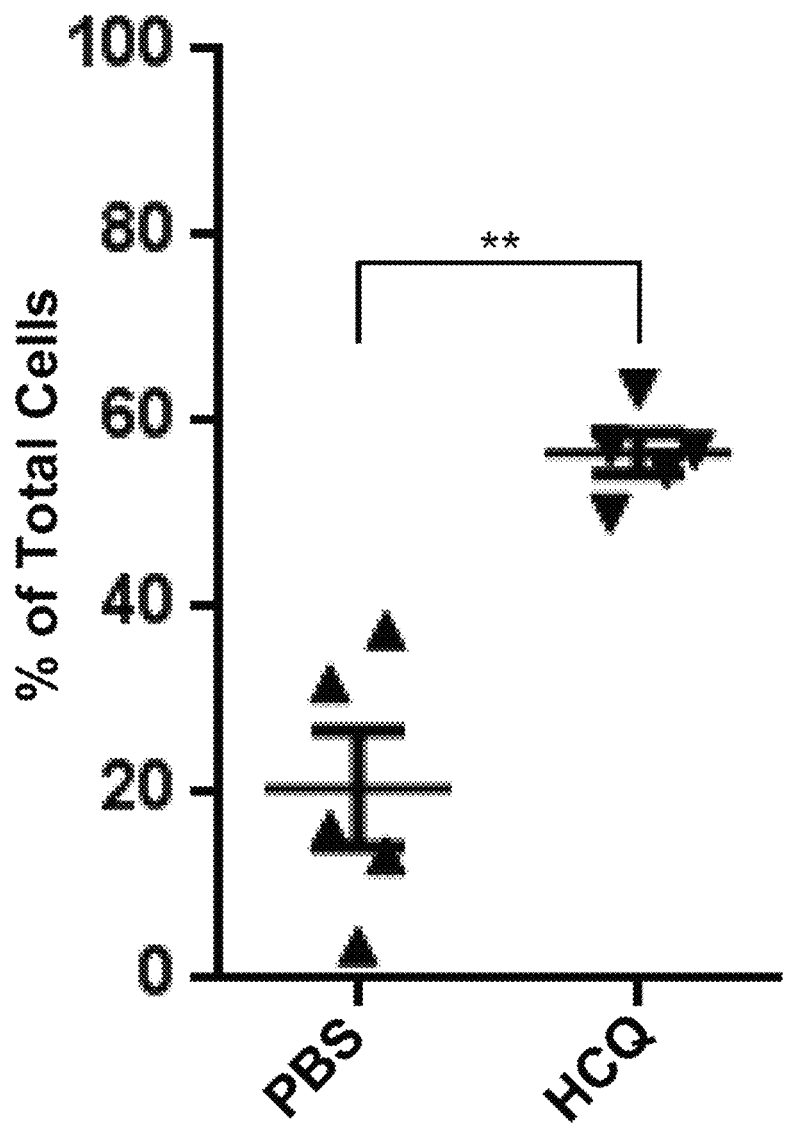
Figure 22J:
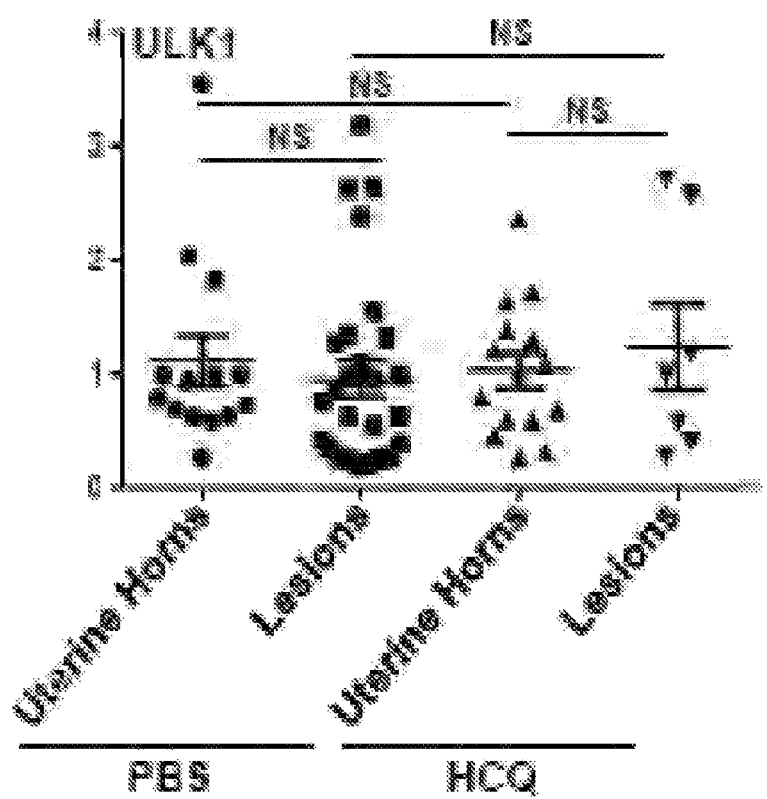
Figure 23:
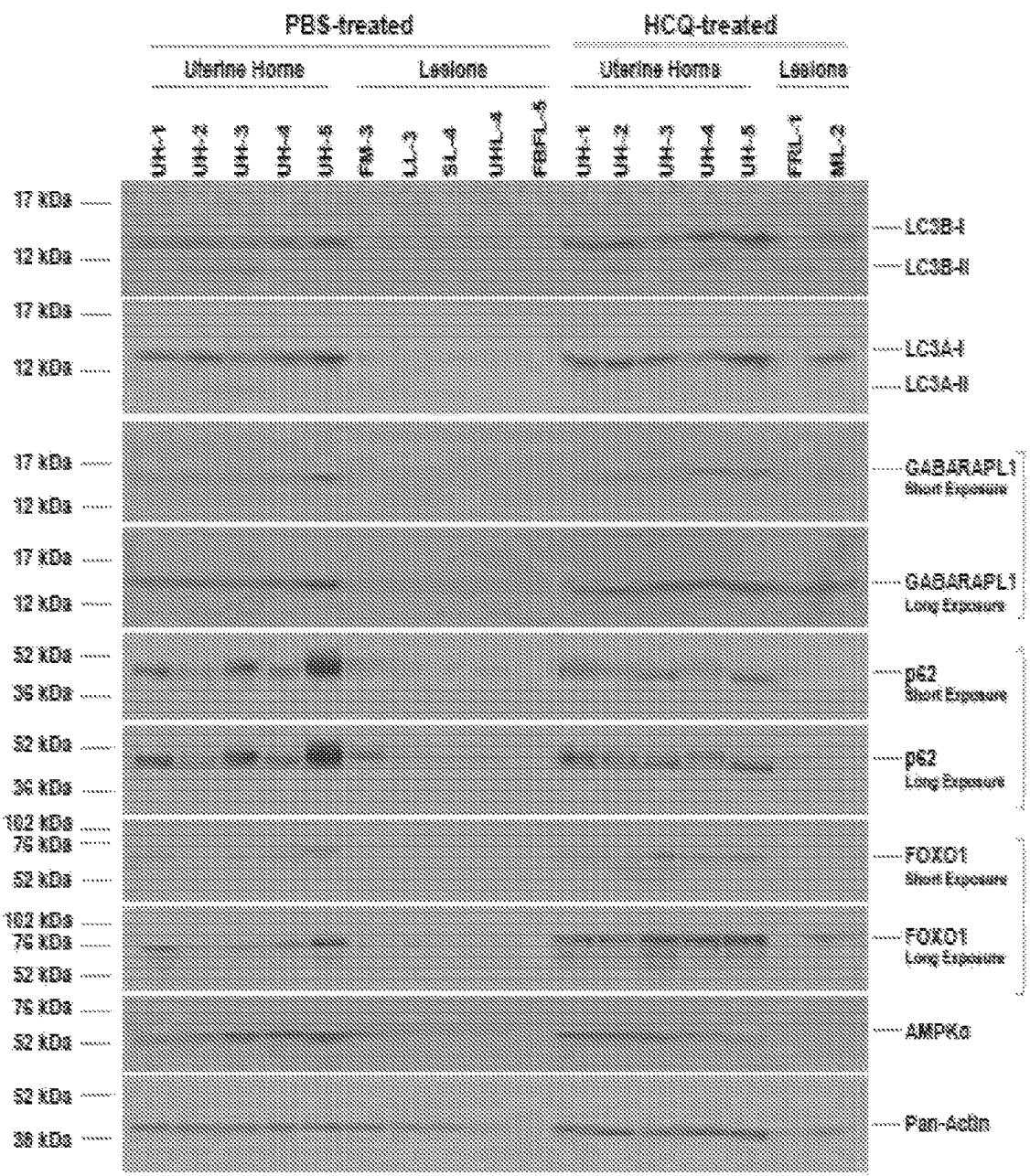
FIG. 23 shows a representative image of a western analysis analyzing protein levels of various autophagic markers in the uterine horns and lesions of mice treated with PBS or HCQ.
Figure 24:
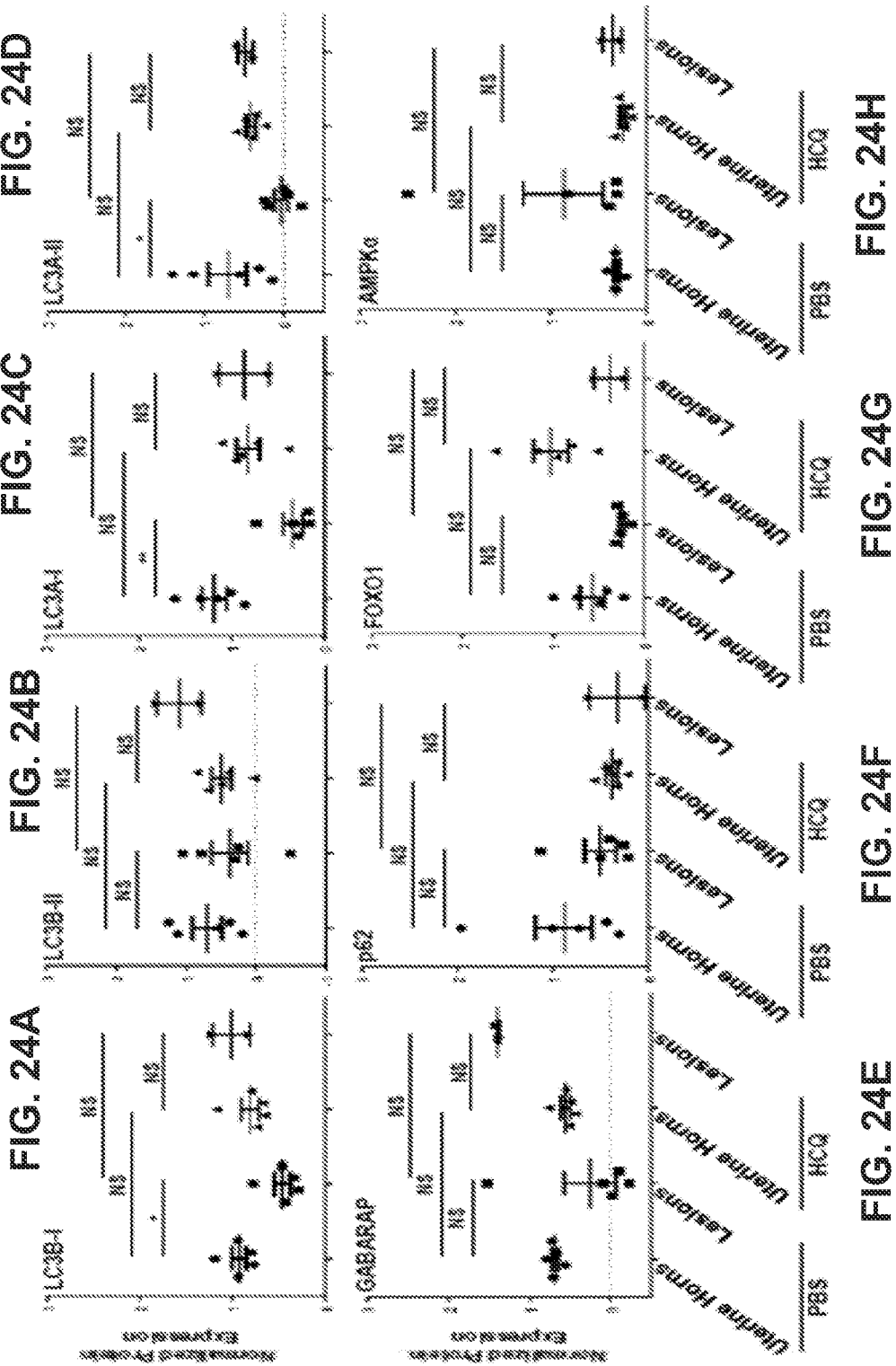
FIGS. 24A-24H show graphs demonstrating normalized protein expression of various autophagic markers in the uterine horns and lesions of mice treated with PBS or HCQ. ● indicates individual reps of uterine horns of mice treated with PBS, ■ indicated individual reps of lesions of mice treated with PBS, ▲ indicates individual reps of uterine horns of mice treated with HCQ, and ▼ indicates individual reps of lesions of mice treated with HCQ.

Macrophage numbers in control, recipient (untreated), PBS-treated, and HCQ-treated recipient mice was also evaluated. There was no significant change in the macrophage numbers present in the peritoneal cavity of control and endometriosis-induced mice at the time of sample collection (2 weeks post-induction), using the canonical macrophage markers CD11b and F4/80 (FIGS. 17A-17C). However, a significant increase (p=0.0079) in macrophage numbers in HCQ-treated mice compared to PBS-treated mice (FIGS. 18A-18C) was observed. These data indicate that HCQ alters the inflammatory response of endometriosis-induced mice.

HCQ Induces Cellular Disorganization in Murine Endometriotic Lesions and Eutopic Endometria.

To determine whether HCQ treatment alters the histopathology (tissue organization) of the recipient's uterine horns and other tissues, a murine tissue microarray (TMA) comprised of 113 cores and performed H&E as well as immunohistochemical staining was developed. The TMA contained uterine horns and ovaries from 10 PBS- and 10 HCQ-treated mice, as well as a mammary gland, a kidney, a lymph node and a small intestine from a PBS-treated mouse for use as antibody controls. Based on H&E staining, we observed that the luminal epithelium of the uterine horn endometrium from HCQ-treated mice had an irregular pattern (FIGS. 19A-19X). Vimentin and cytokeratin 8 (CK8) appeared to be appropriately localized to the stromal and epithelial compartments, respectively, independently of HCQ treatment. Estrogen receptor α (ERα) was primarily localized to the epithelial cell layer of the endometrial glands, while progesterone receptor (PR) appeared to be evenly distributed between the stromal and epithelial cell compartments. [24] However, the PR staining was comparatively much weaker to that for ERα. Again, no differences were noted in the tissues from PBS and HCQ-treated mice for ERα and PR staining pattern or intensity. LC3B expression appeared more intense in HCQ-treated mice relative to PBS-treated mice in both the stromal and epithelial compartments (FIGS. 19A-19X). The same immunohistochemical markers were also stained for in ovaries, but no marked differences in the intensity or localization pattern of any of these proteins in these tissues from HCQ-treated mice relative to those from PBS-treated mice were observed.

Induction of Endometriosis Down-Regulates mRNA and Protein Expression of Autophagic Markers in Ectopic Compared to Eutopic Murine Endometrium.

To determine whether the expression of autophagic mediators in uterine horns and lesions differs between PBS and HCQ-treated mice, real-time PCR was used to quantify the mRNA transcript levels of 10 major molecules involved in the autophagic pathway. In PBS-treated animals, it was determined that the mRNA levels of ATG5 (p=0.0294), ATG4B (p=0.0004), ATG2B (p=0.0440), and beclin-1 (p<0.0001) were significantly decreased in the analyzed endometriotic lesions compared to uterine horns (uterine horns from PBS-treated mice, n=14; lesions from PBS-treated mice, n=28; uterine horns from HCQ-treated mice, n=15; and lesions from HCQ-treated mice, n=7) (FIG. 4a). Due to limited sample availability, LC3B and ATG2B were analyzed using a smaller number of samples (i.e., For LC3B: uterine horns from PBS-treated mice, n=9; lesions from PBS-treated mice, n=18; uterine horns from HCQ-treated mice, n=10; and lesions from HCQ-treated mice, n=4. For ATG2B: uterine horns from PBS-treated mice, n=5; lesions from PBS-treated mice, n=10; uterine horns from HCQ-treated mice, n=5; and lesions from HCQ-treated mice, n=2). No significant differences were noted between lesions and uterine horns from HCQ-treated C57BL/6 mice (likely due to smaller lesion numbers available in the HCQ group although similar trends were apparent). However, lesions obtained from these HCQ-treated mice had a significant increase in ATG5 (p=0.0499) and ATG3 (p=0.0248) compared to lesions from PBS-treated mice (FIGS. 22A-22J). A certified pathologist confirmed epithelial and stromal components in the lesions analyzed. Lesions (independent blocks and not on the above-described TMA [see Materials and Methods section of this Example]) were also immunostained for CK8, vimentin, ERα, and PR, and LC3B (FIGS. 20A-20J). The epithelial cells of the glands were positive for CK8, ERα, and PR expression which provides supporting data that the collected lesions originated from endometrial tissue (FIGS. 20A-20J). An absence of glandular components was observed in four out of the seven stained lesions from HCQ-treated mice as demonstrated by CK8, ERα, and PR immunohistochemical staining. These results (with the H&E data presented in FIGS. 14A-14D) suggest that HCQ alters the organization of ectopic growths in the murine model of endometriosis. FIGS. 21A-21H displays representative images of positive and negative staining controls for the antibodies used.

The Balb/c mouse strain was also used for the induction model to demonstrate that the changes observed in autophagy gene expression are independent of the mouse genetic strain used. [20] In this model, it was identified that the mRNA levels of ATG7 (p=0.0174), ATG4B (p=0.0020), and beclin-1 (p<0.0001) were significantly reduced in endometriotic lesions (n=8) compared to uterine horns (n=8) derived from the same recipient mice (FIGS. 41A-41F).

Protein levels of autophagic markers were analyzed in both lesions and uterine horns from PBS and HCQ-treated mice (FIG. 23) from the following groups: (1) PBS-treated mice: uterine horns (n=15), (2) HCQ-treated mice: uterine horns (n=15), (3) PBS-treated mice: lesions (n=10), and (4) HCQ-treated mice: lesions (n=7). LC3B-I, LC3B-II, LC3A-I, and LC3A-II were decreased in lesions compared to uterine horns from both PBS- and HCQ-treated mice. Expression of GABARAPL1-I was detected in uterine horns collected from both groups of treated mice and was decreased in the lesions; however, the conjugated form, GABARAPL1-II, was not observed in any of the murine specimens. A decrease was also observed in p62 in endometriotic lesions relative to uterine horns that was independent of HCQ treatment. FOXO1 and AMPKα protein levels in the uterine horns were variable amongst the samples analyzed, although they were both reduced within the lesions (FIGS. 23 and 24A-H). To determine whether HCQ treatment altered expression of autophagic mediators in other organs, various tissue specimens (kidneys, thymus, spleen, lung, pancreas, heart, and liver) were harvested from each treatment group (5 PBS-treated mice and 5 HCQ-treated mice) and LC3B levels were assessed (FIGS. 46 and 47A-47H). The lung and heart showed differences in LC3B-II expression following HCQ treatment. Overall, these results suggest that the protein expression of autophagic mediators is dysregulated in endometriotic lesions.

RNA Expression of Autophagic Markers is Dysregulated in Eutopic Endometria Upon Induction of Endometriosis.

Figure 25:
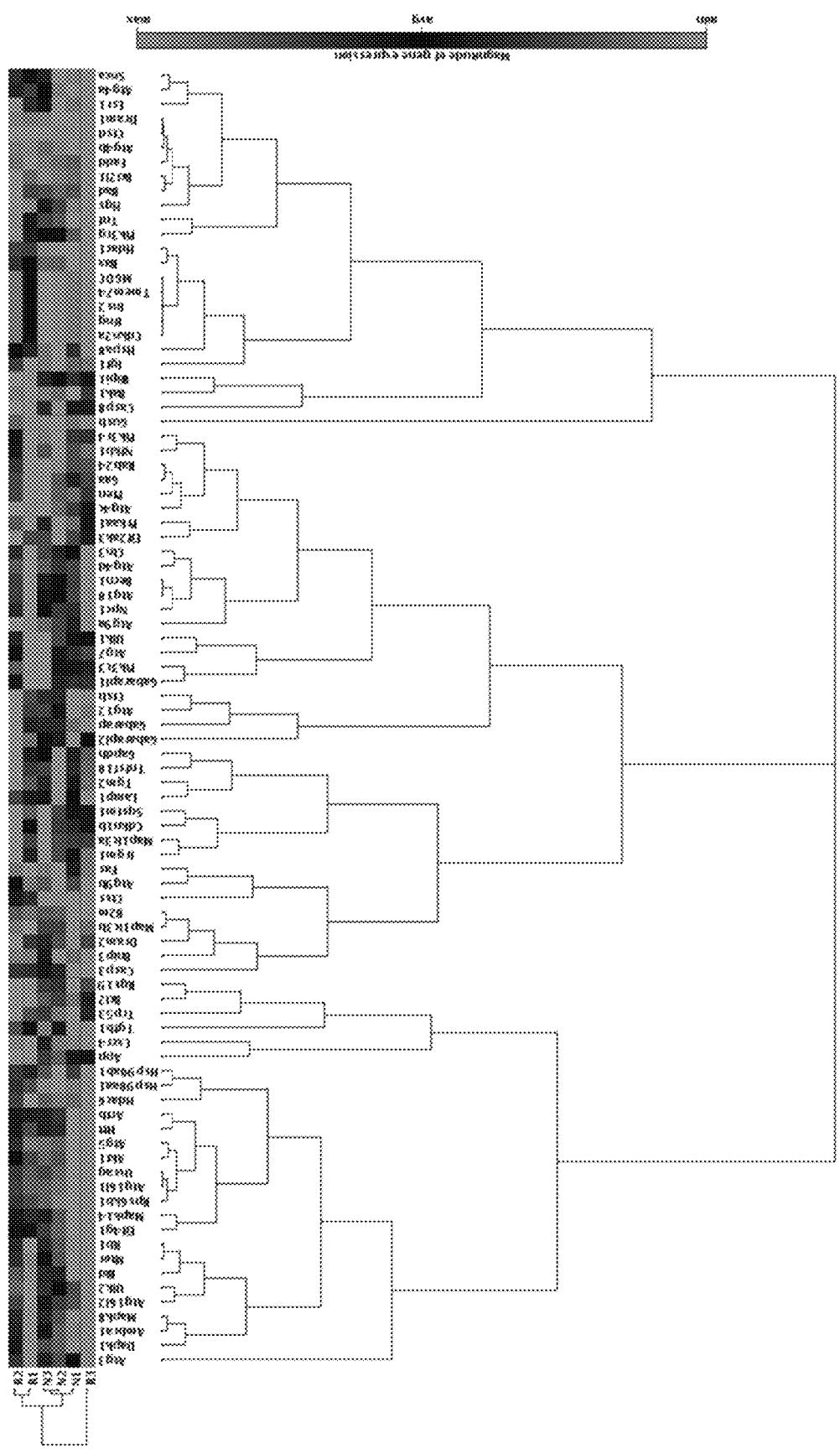
FIG. 25 shows a heat map demonstrating a comparison of RNA isolated from uterine horns of control mice to recipient mice.
Figure 26:
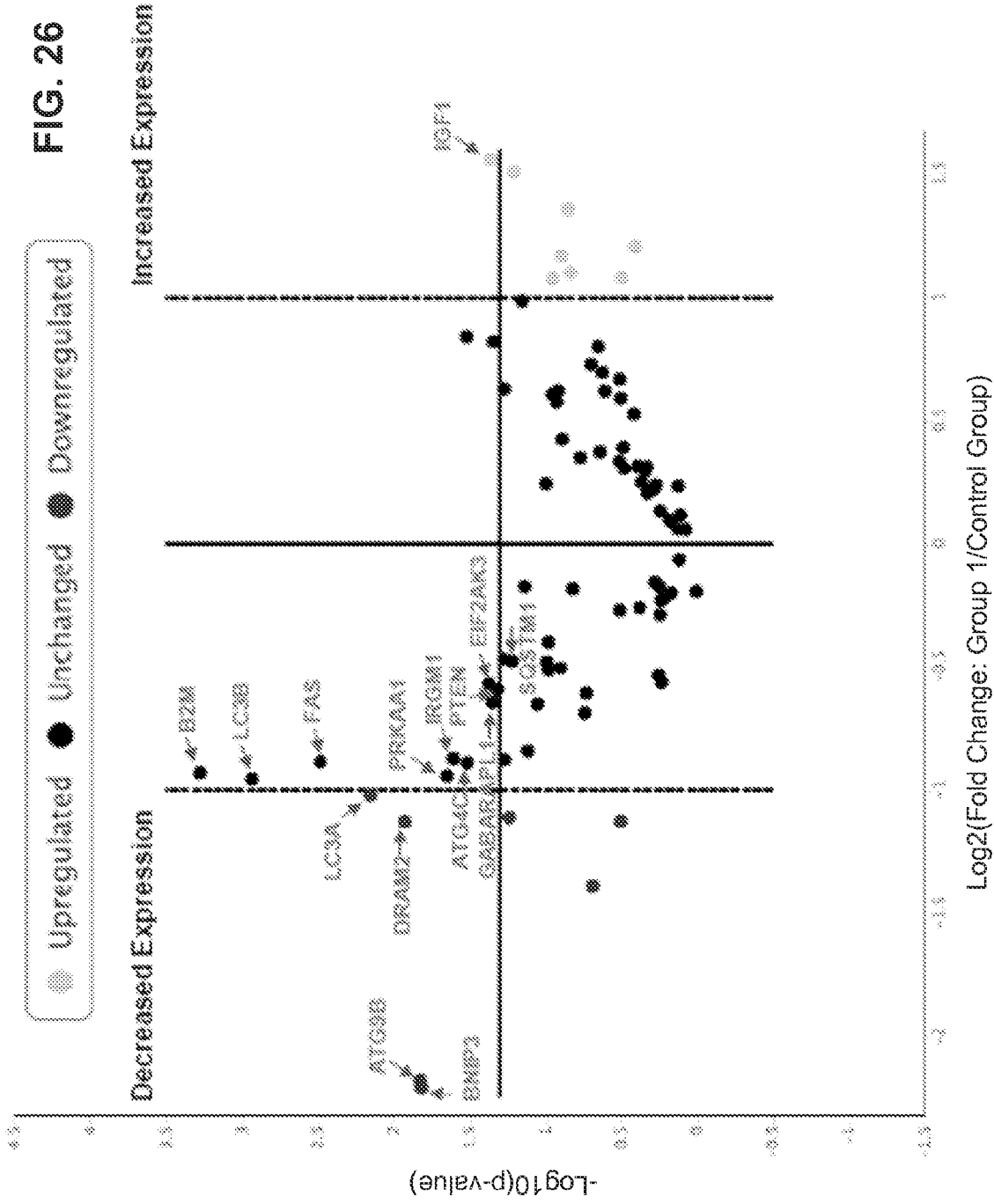
FIG. 26 shows a volcano plot that displays the fold-changes in autophagy genes in eutopic endometria between recipient and control mice.
Figure 27:
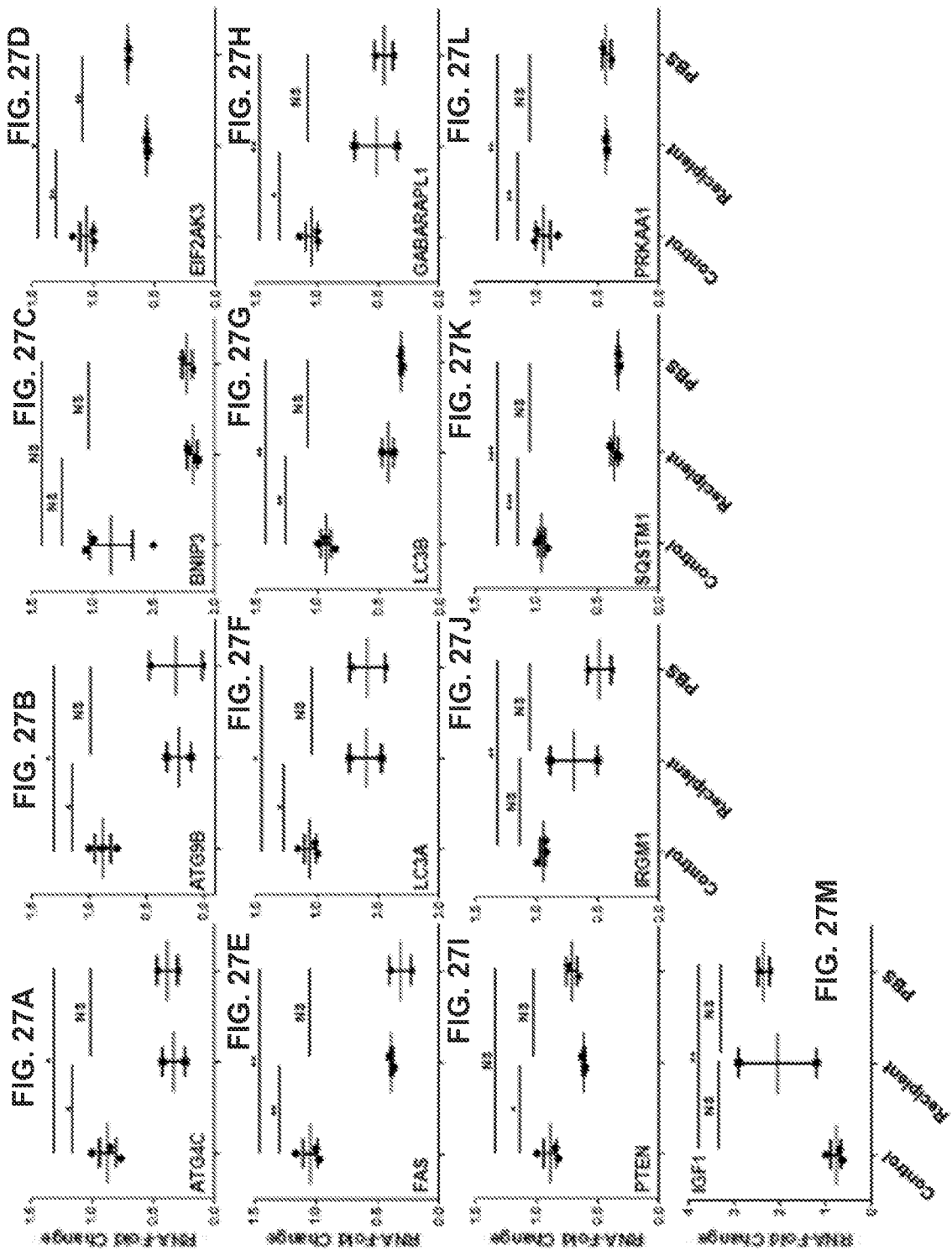
FIGS. 27A-27M show graphs demonstrating mRNA expression (expressed as a Fold-change) of various autophagic markers in PBS treated, control, and recipent mice. ● indicates individual reps of uterine horns from control mice, ■ indicates individual reps of uterine horns from recipient mice, and ▲ indicates individual reps from PBS treated mice.
Figure 28:
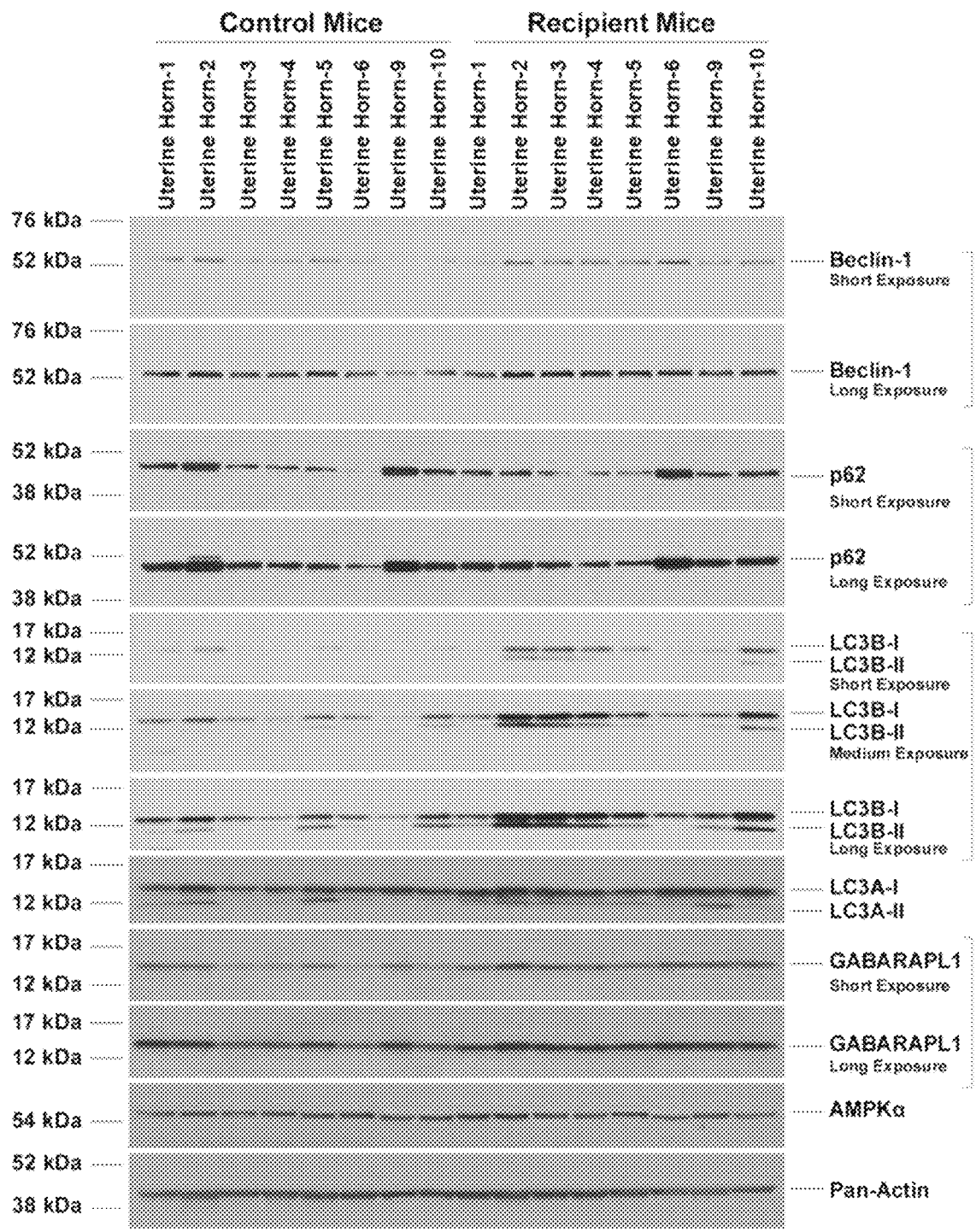
FIG. 28 shows a representative image of a western blot demonstrating protein expression of various autophagic markers in the uterine horns of control and recipient mice.
Figures 29A, 29E:
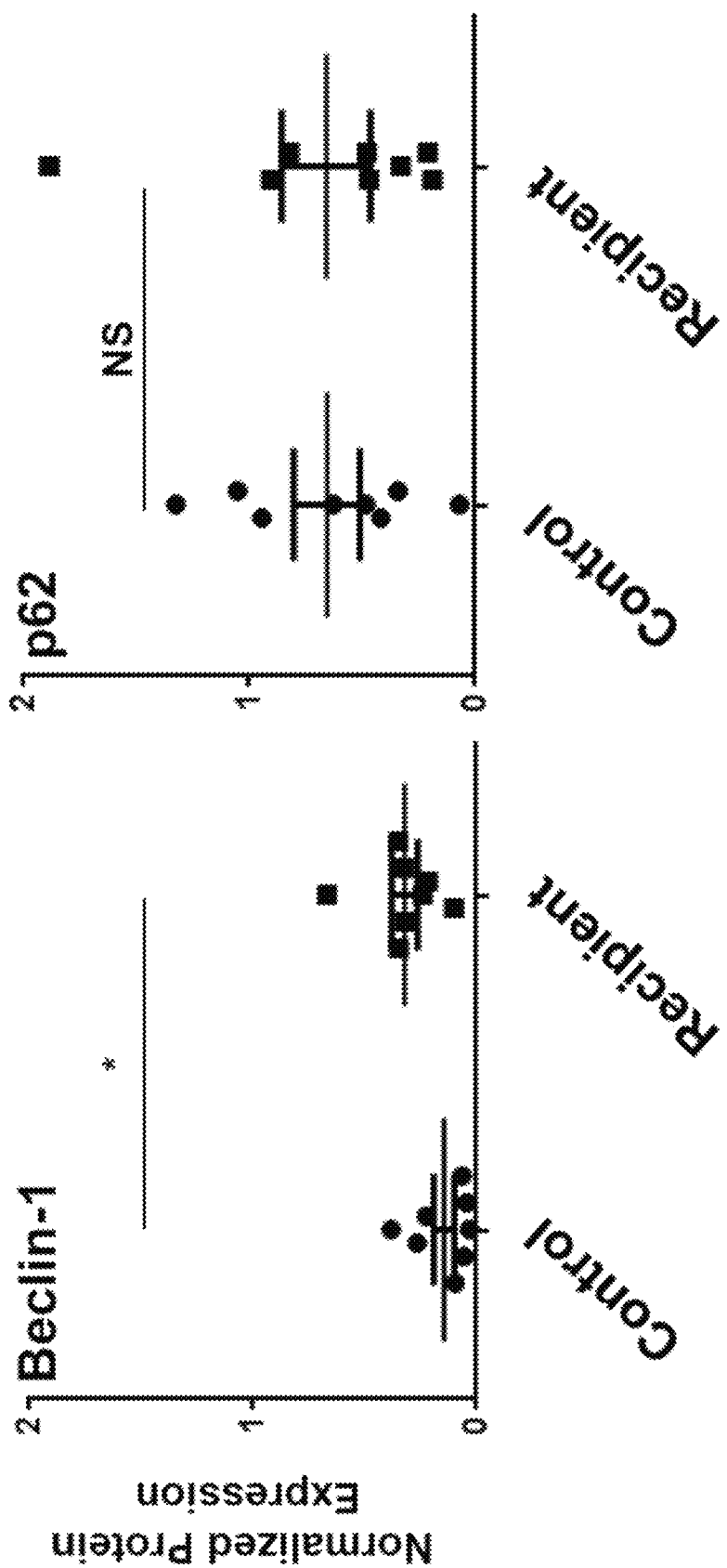
FIGS. 29A-29H show graphs demonstrating the normalized protein expression of various autophagic markers in control and recipient mice. ● indicates individual reps of uterine horns from control mice and ■ indicates individual reps of uterine horns from recipient mice.
Figures 29B, 29F:
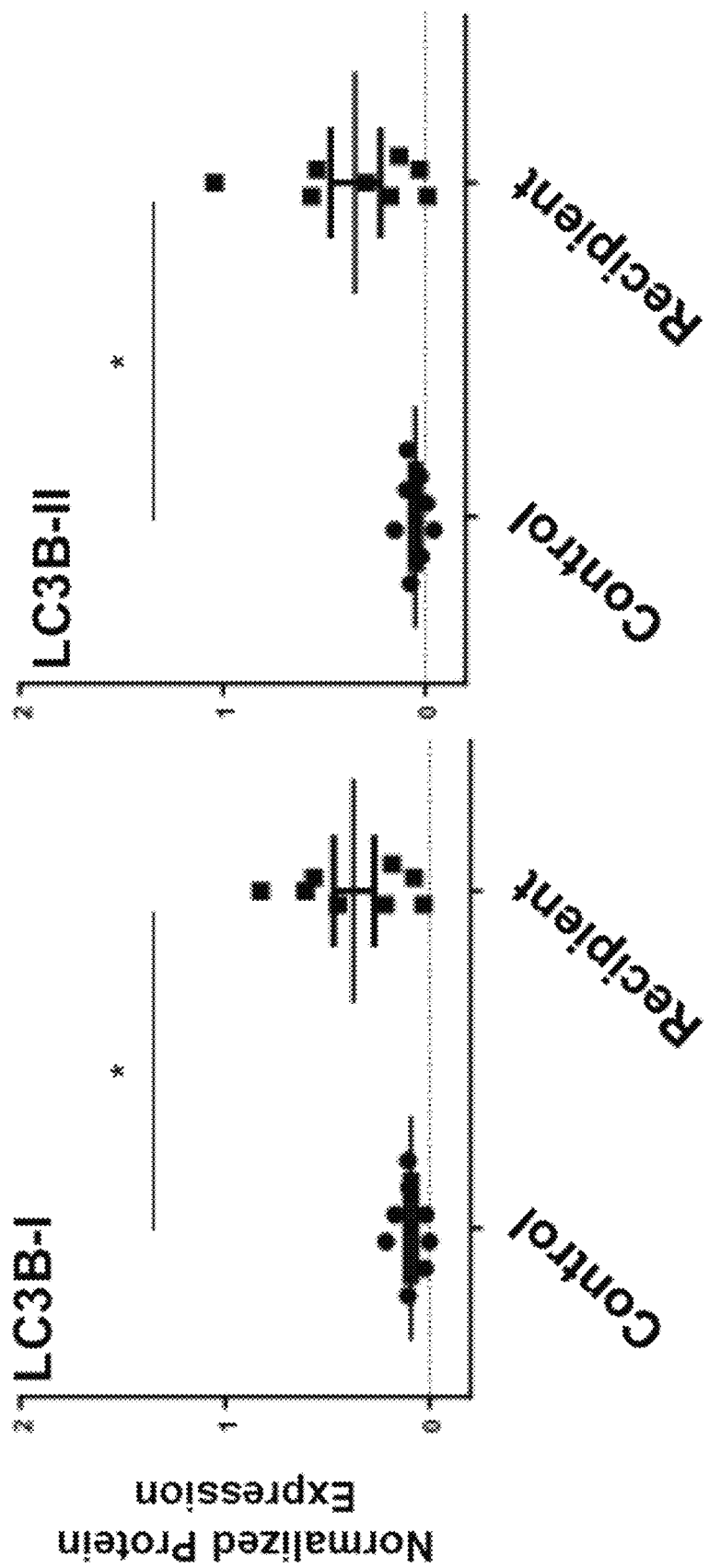
Figures 29C, 29G:
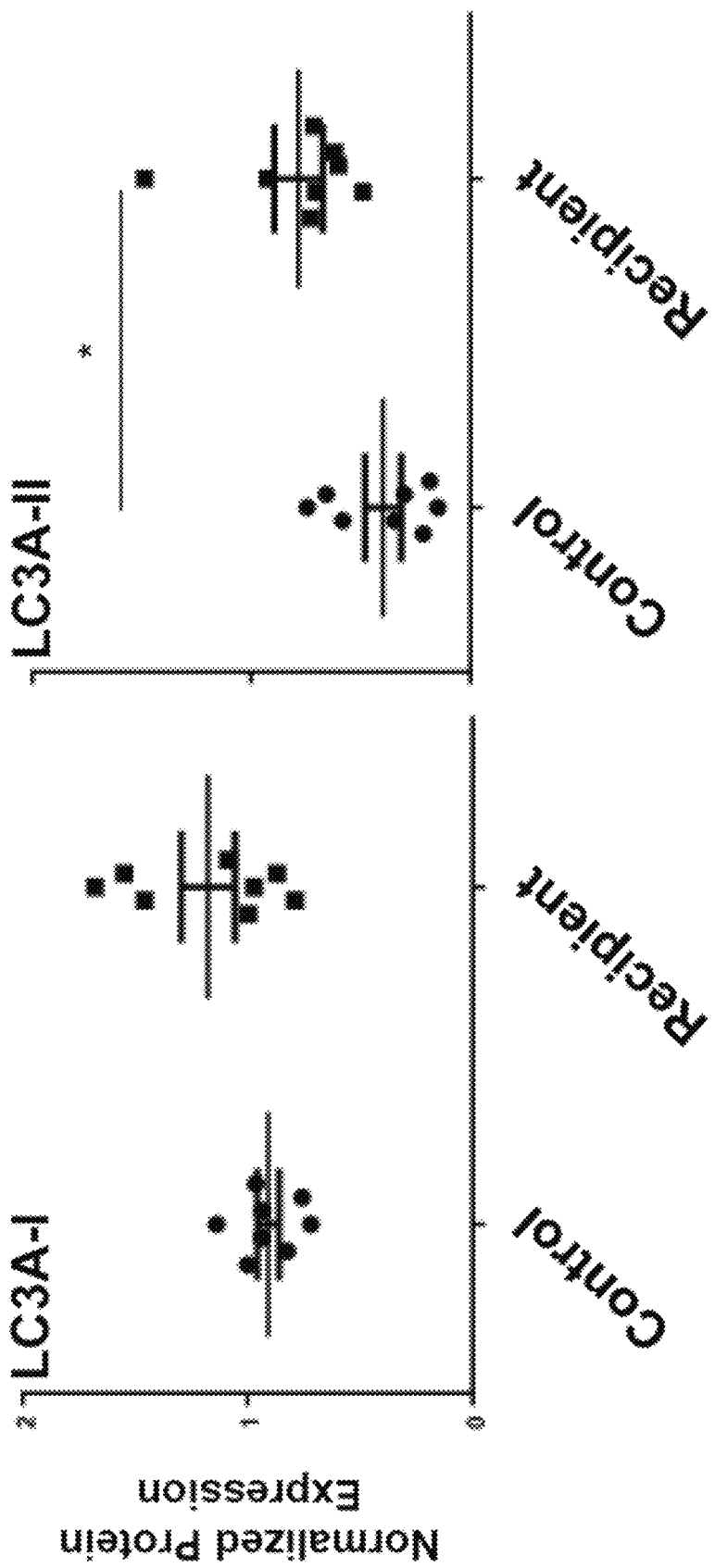
Figures 29D, 29H:
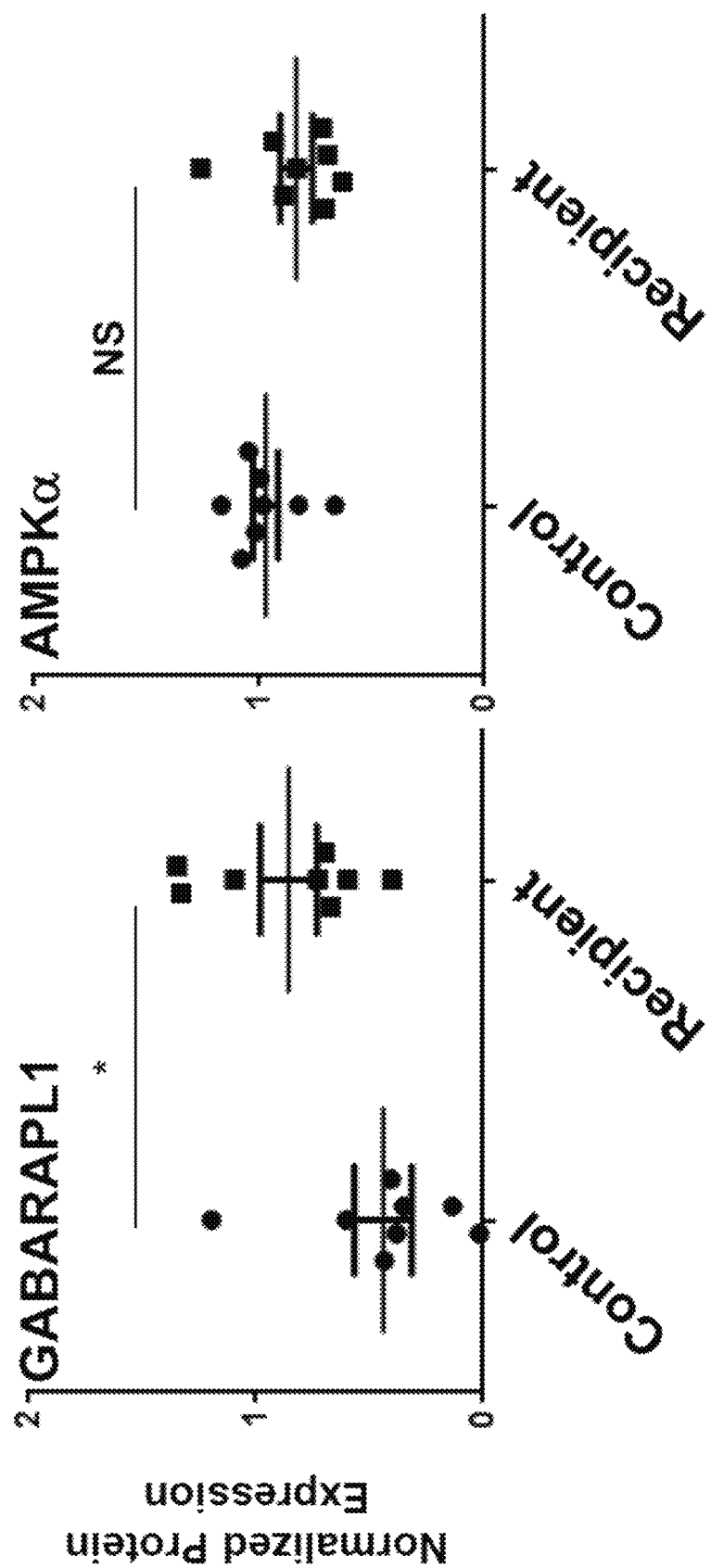
Figure 42:
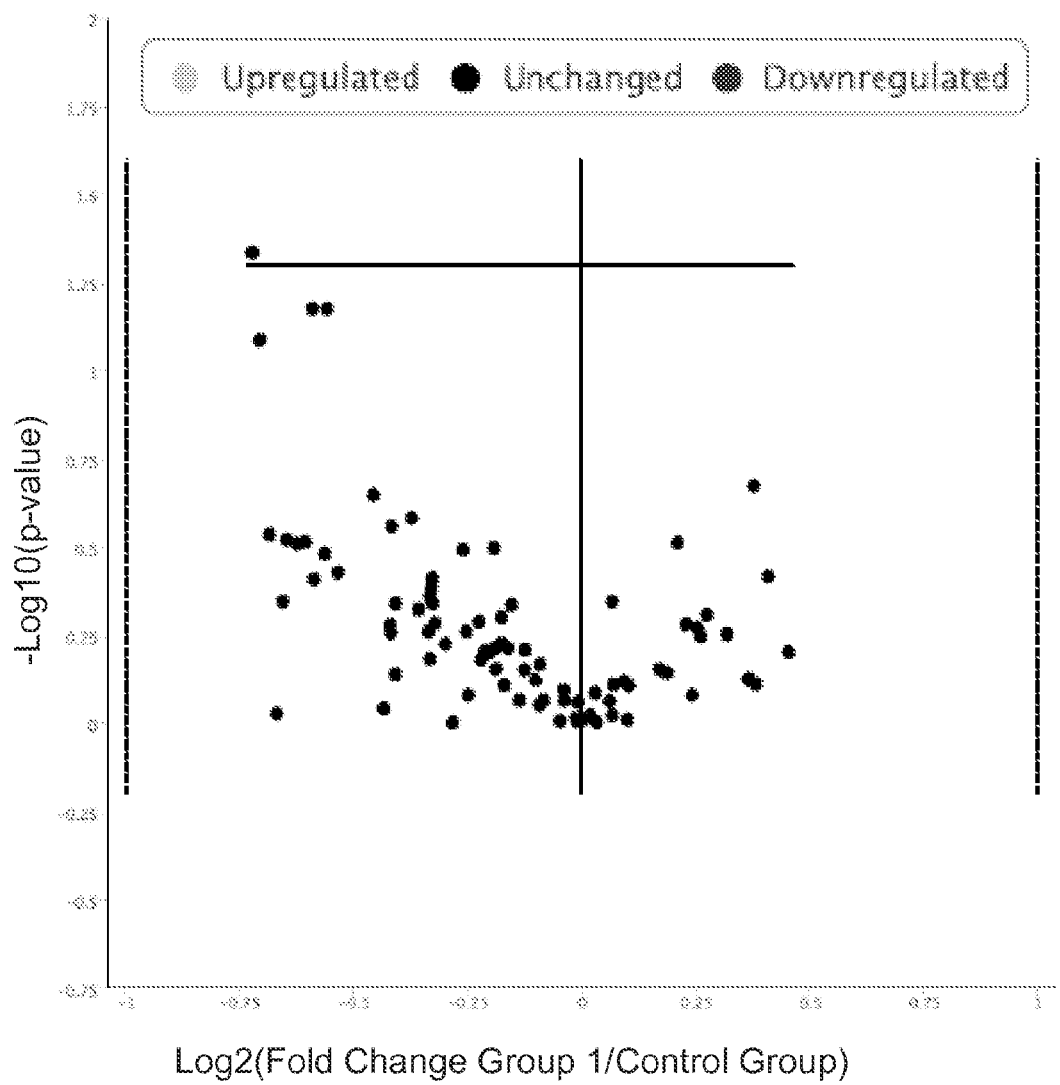
FIG. 42 shows a volcano plot demonstrating the fold-changes in autophagy genes in eutopic endometria between recipient and control mice.
Figure 44:
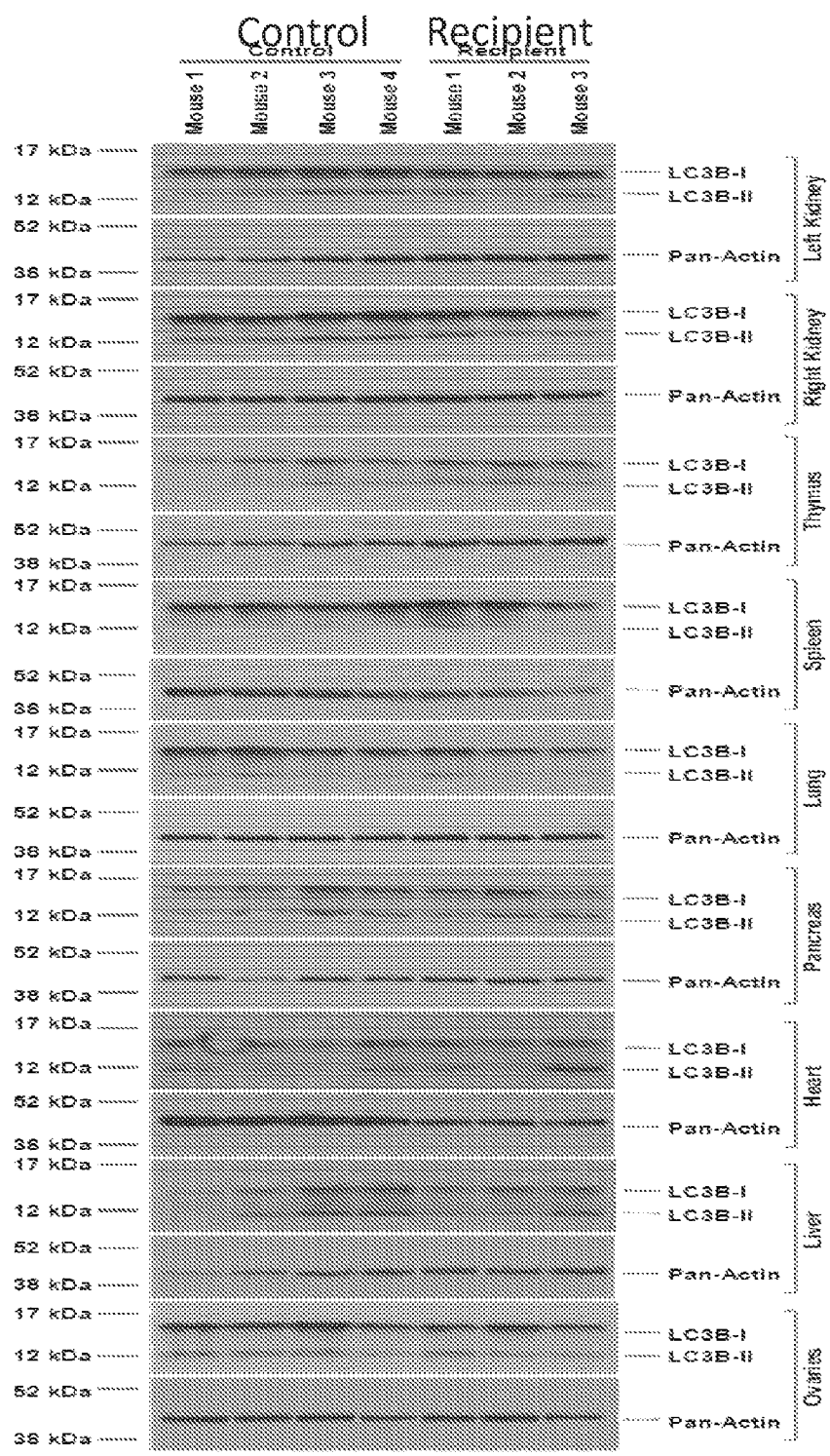
FIG. 44 shows images of representative western blots demonstrating LC3B-I and LC3B-II protein expression in various tissues of control and recipient mice.
Figure 45:
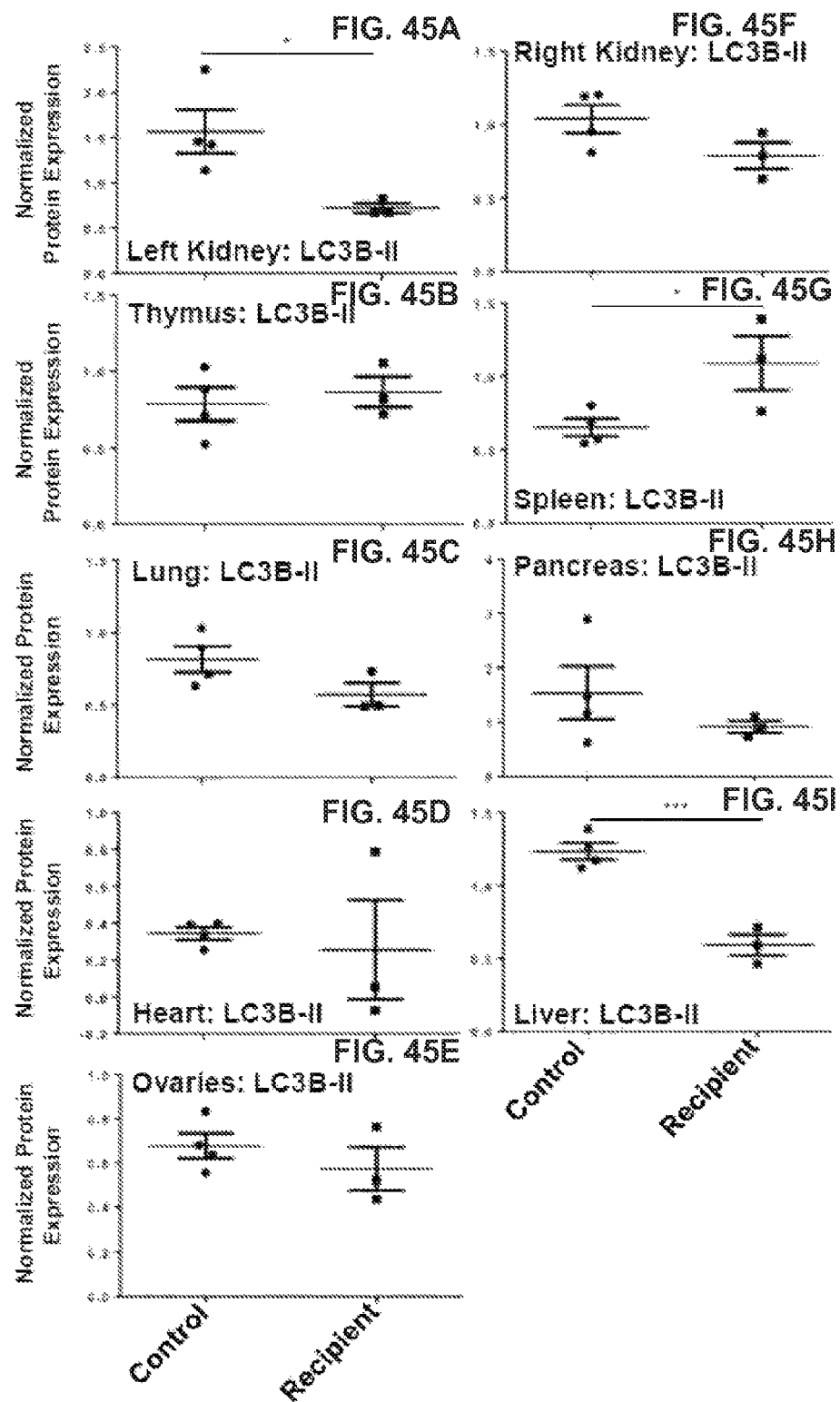
FIGS. 45A-45I show graphs demonstrating normalized protein expression of LC3B-II in various tissues of control and recipient mice.
Figure 46:
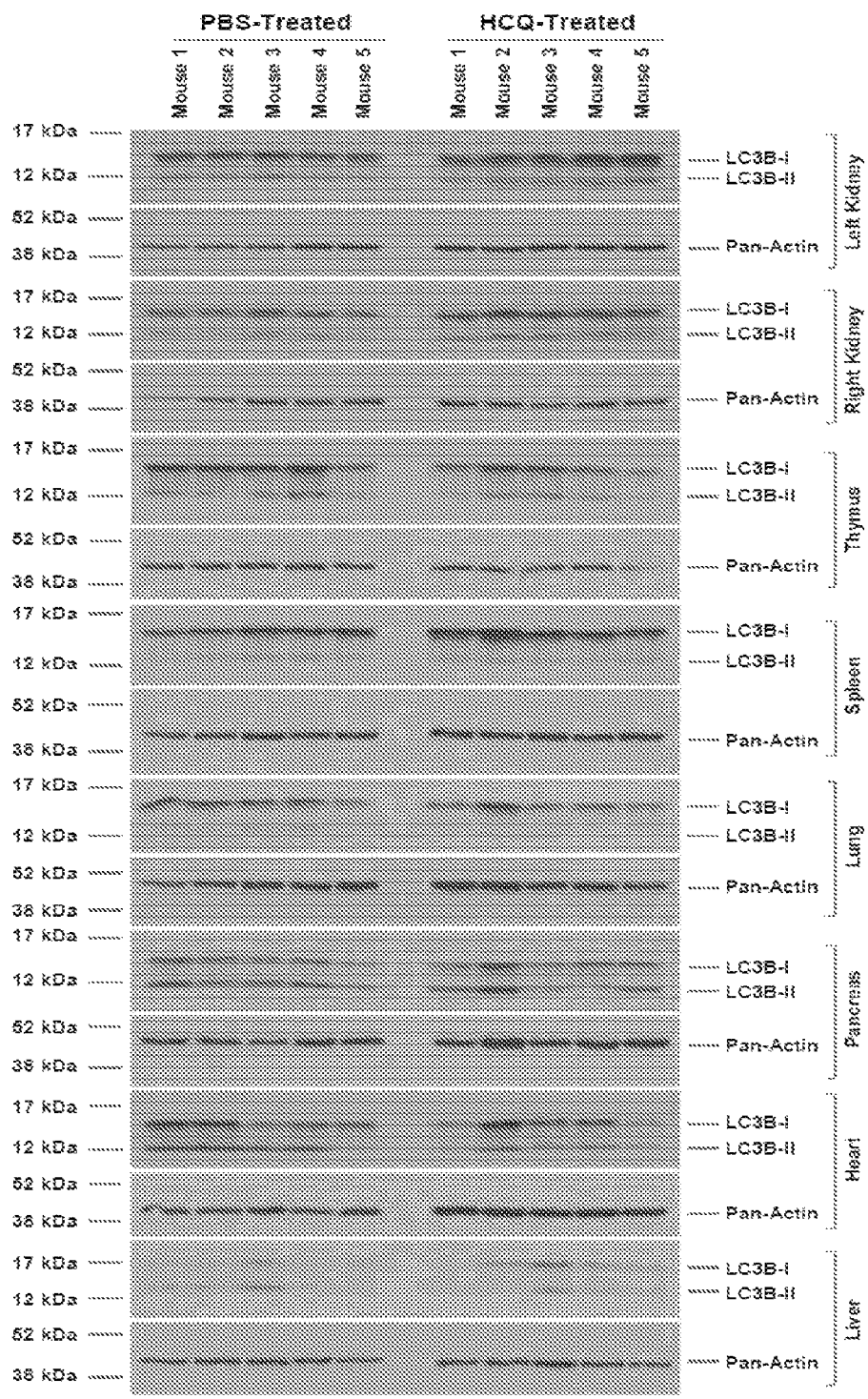
FIG. 46 shows images of representative western blots demonstrating LC3B-I and LC3B-II protein expression in various tissues of PBS treated and HCQ treated mice.
Figure 47:
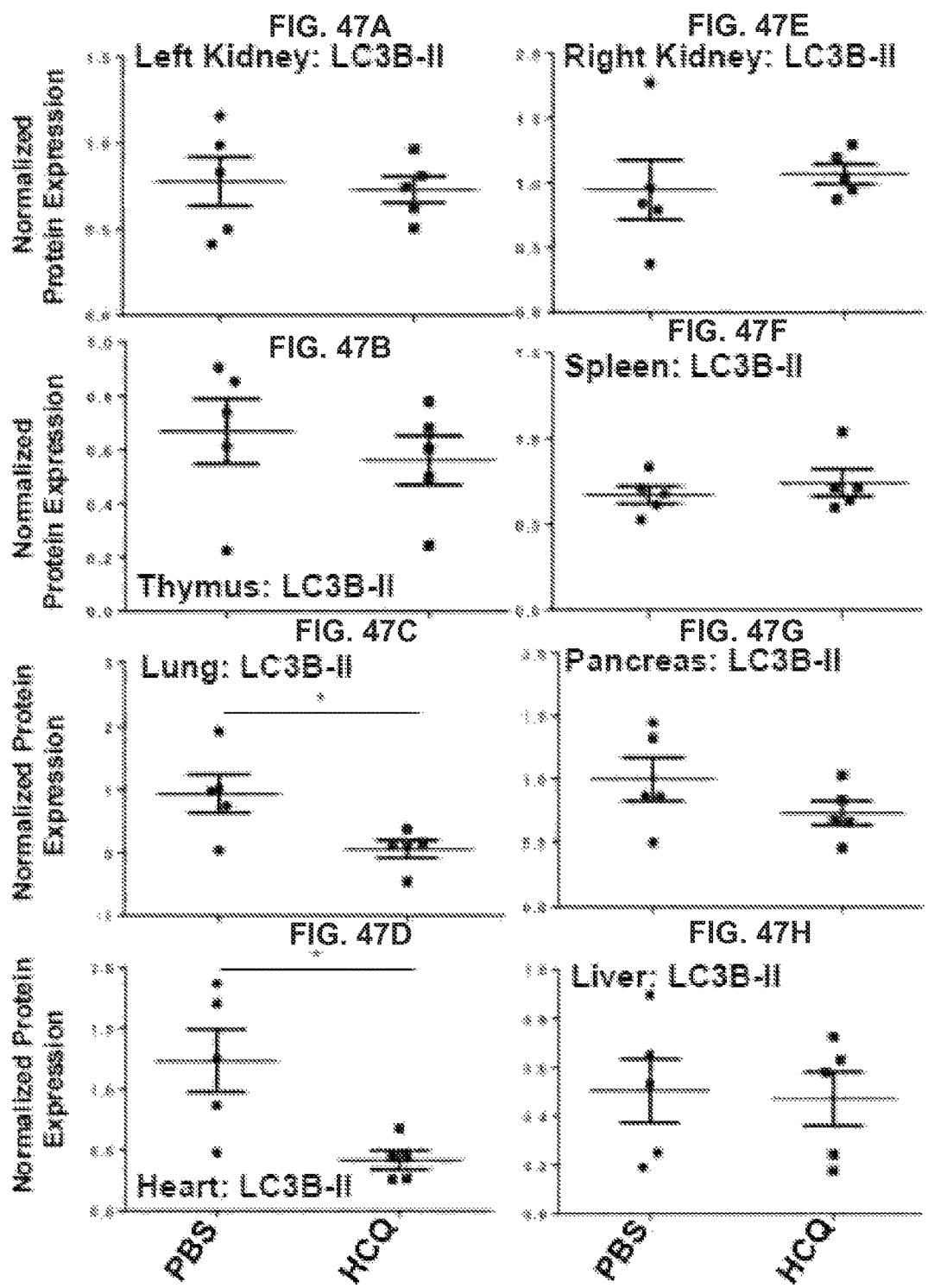
FIGS. 47A-47H show graphs demonstrating normalized protein expression of LC3B-II in various tissues of of PBS treated and HCQ treated mice.

Eutopic endometria from patients with endometriosis differs from the eutopic endometria from endometriosis-free subjects. [25, 26] To identify changes in the expression of key autophagic markers in this context, an RT2-PCR autophagy focused profiler array was used to analyze RNA isolated from uterine horns from control (non-induced) and recipient (untreated). The uterine horns from recipient mice were compared with those from PBS-treated recipient mice to verify there was no significant change that occurred upon intraperitoneal injection with PBS. Three representative samples were selected from each group based on RNA quality. A heat map comparing gene expression in RNA isolated from uterine horns from control mice to recipient mice is shown in FIG. 25. The results indicated that there is a subset of autophagy genes that is differentially expressed. A volcano plot is shown in FIG. 26 that displays the fold-changes in autophagy genes in eutopic endometria between recipient and control mice. Dysregulated genes were identified (with statistical significance) between these two groups of samples. IGF1 was the an autophagic marker that was significantly increased (p=0.044); the remaining 12 markers were all significantly decreased (BNIP3, p=0.015; ATG9B, p=0.015; LC3A, p=0.007; LC3B, p=0.0012; PRKAA1, p=0.023; ATG4C, p=0.031; FAS, p=0.003; IRGM1, p=0.025; GABARAPL1, p=0.045; PTEN, p=0.048; EIF2AK3, p=0.043; and SQSTM1, p=0.054). As shown in FIG. 42, significant changes upon PBS treatment in the RT2-PCR array were not observed.

To validate these "top hits" (i.e., increased by at least 2-fold with p<0.05) identified from the autophagic pathway RT2-PCR profiler array, we performed real-time PCR using TaqMan FAM-labeled probes/primers (FIGS. 27A-27M and 48) Using this approach, 10 of the 13 "top hits" were validated (FIGS. 27A-27M): ATG4C (p=0.0167), ATG9B (0.0113), EIF2AK3 (p=0.0068), FAS (p=0.0034), LC3A (p=0.0306), LC3B (p=0.0040), GABARAPL1 (p=0.0360), PTEN (p=0.0295), SQSTM1 (p=0.0008), and PRKAA1 (p=0.0065) were significantly reduced. It was observed that the expression of EIF2AK3 (p=0.0014) was increased (FIGS. 27A-27M). Taken together, these data suggest that autophagy is dysregulated in the eutopic endometria of endometriosis-induced mice.

Increased LC3 Protein and Lipid Droplets in Eutopic Endometria of Endometriosis-Induced Mice Compared to Eutopic Endometria of Controls.

To determine whether the RNA level changes of key autophagic markers observed between the eutopic endometria of endometriosis-induced mice (n=10) and non-induced (control) mice (n=10) translated to protein level changes, their protein levels were assessed via western blot analyses. As shown in FIGS. 28 and 29A-29H and 49, beclin-1 (2.20-fold change, p=0.0330), LC3B-I (4.00-fold change, p=0.0185), LC3B-II (6.76-fold change, p=0.0364), LC3A-II (1.97-fold change, p=0.0135), and GABARAPL1 (1.95-fold change, p=0.0334) were significantly increased in uterine horns from endometriosis-induced mice relative to those from control mice. LC3A-I and LC3B-I have an expected molecular weight of approximately 16 kDa, while LC3A-II and LC3B-II have an expected molecular weight of approximately 14 kDa.27. When GABARAPL1 expression was assessed, the conjugated form was not detected. While not being bound to theory, this observation suggests that the primary form expressed in these tissues is the cytosolic form (GABARAPL1-I). To assess if the increased levels of LC3B were specific to the uterine horns in the endometriosis-induced mice, LC3B protein levels were analyzed in homogenates prepared from kidneys, thymus, spleen, lung, pancreas, heart, liver, and ovaries from both recipient (n=3) and control (n=4) mice. Out of the nine tissues analyzed, only the left kidney, spleen, and liver appeared to show differences in LC3B-II levels (FIGS. 44 and 45A-45I).

Figure 30E:
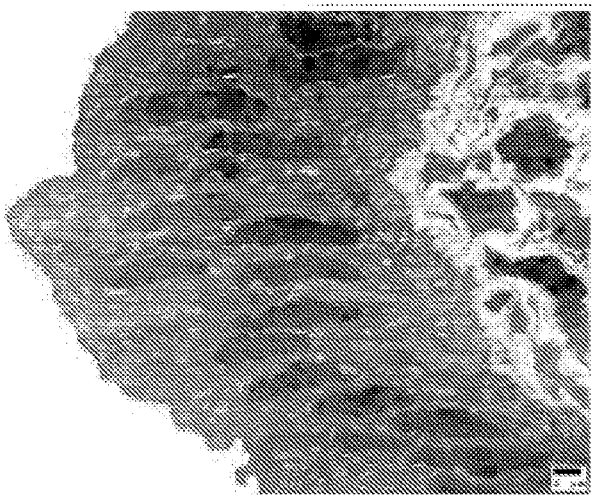
FIGS. 30A-30B show representative transmission electron microscopy (TEM) images of eutropic endometria of endondometriosis-induced mice (FIGS. 30E-30G) and control mice (FIGS. 30A-30D).
Figure 30F:
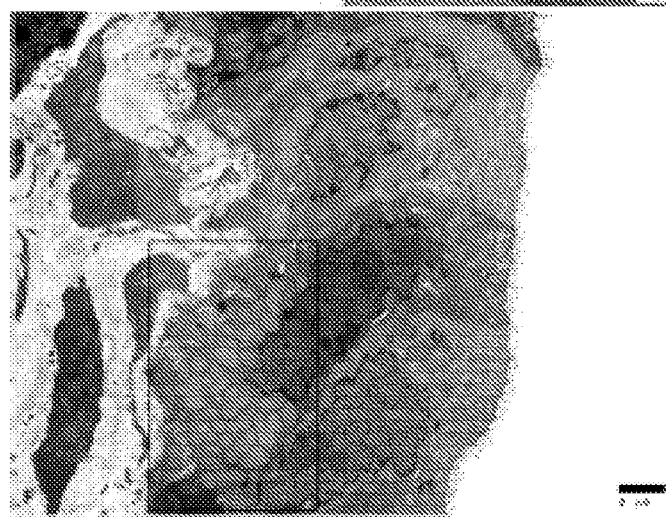
Figure 30G:
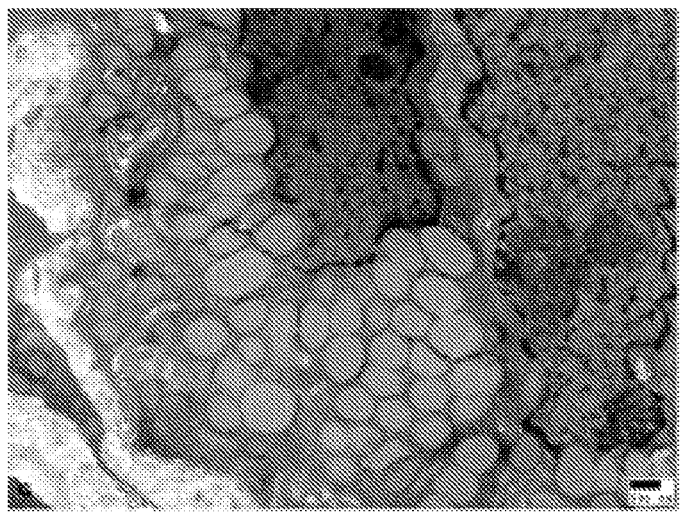

To test whether the observed increases in LC3A and LC3B correlated with an increase in autophagosome formation in the eutopic endometria of endometriosis-induced mice, TEM was performed (FIGS. 30A-30G). Although no autophagosomes were identified in eutopic endometria from control mice (FIGS. 30A-D) and eutopic endometria from endometriosis-induced mice (FIGS. 30E-G), an increase was observed in lipid droplet numbers in the epithelial cells of eutopic endometria from endometriosis-induced mice. In addition, it was also observed that more "unhealthy" electron-dense epithelial cells in uterine horns from endometriosis-induced mice (FIG. 30E) compared to control mice (FIG. 30A). Together and without being bound by theory, these results suggest that expression of autophagic mediators (i.e., LC3) is dysregulated in the eutopic endometria of endometriosis-induced mice which is associated with an accumulation of lipid droplets in the epithelial cells.

Immunohistochemical Staining of LC3B in the Epithelium and Stromal Components of Eutopic and Ectopic Endometrium in Patients with Endometriosis.

Figure 32A:
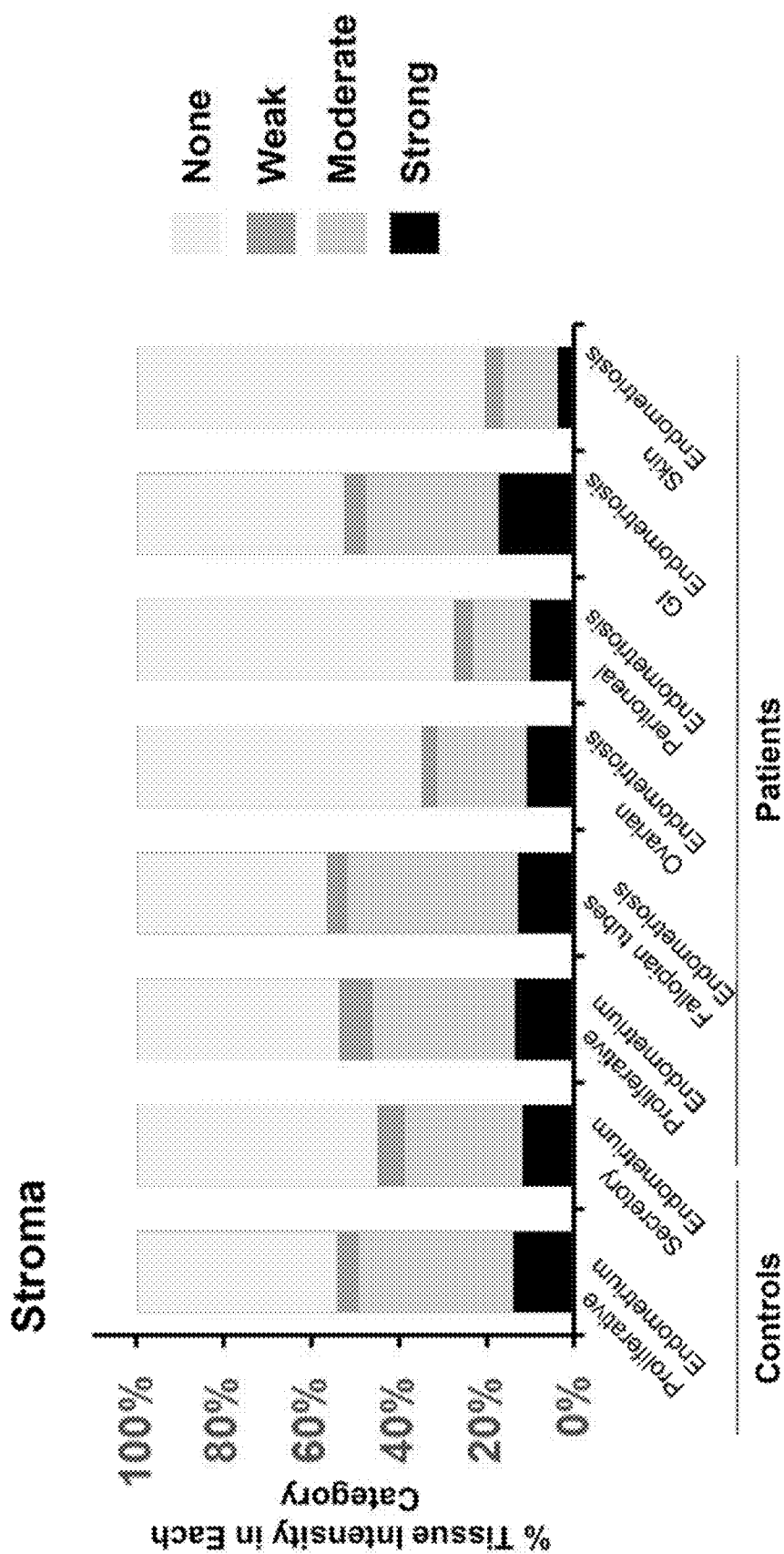
FIGS. 32A-32B show graphs demonstrating % tissue intensity in each category (none, weak, moderate, or strong) of stromal (FIG. 34A) and epithelial (FIG. 34B) expression.
Figure 32B:
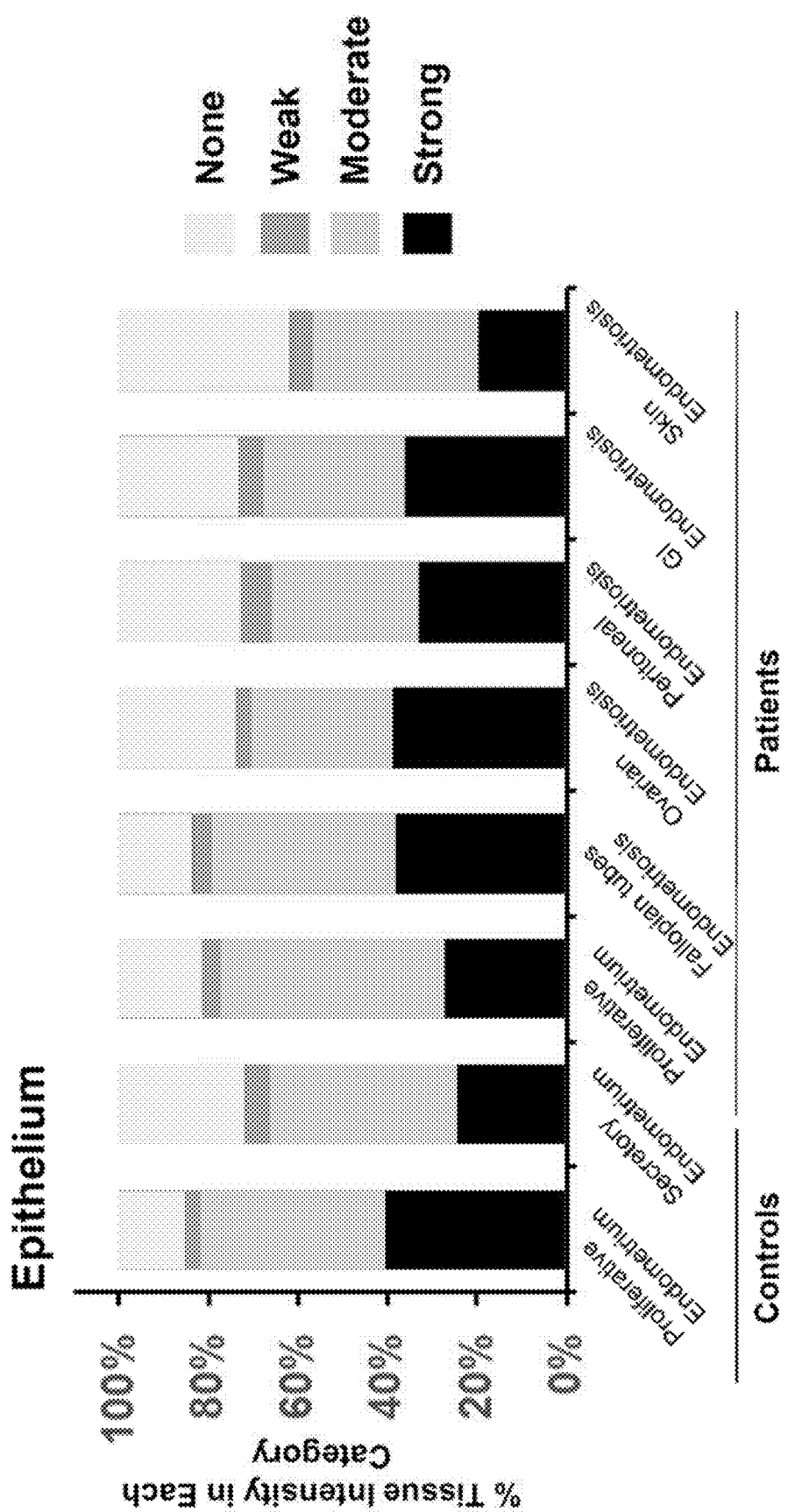
Figure 33:
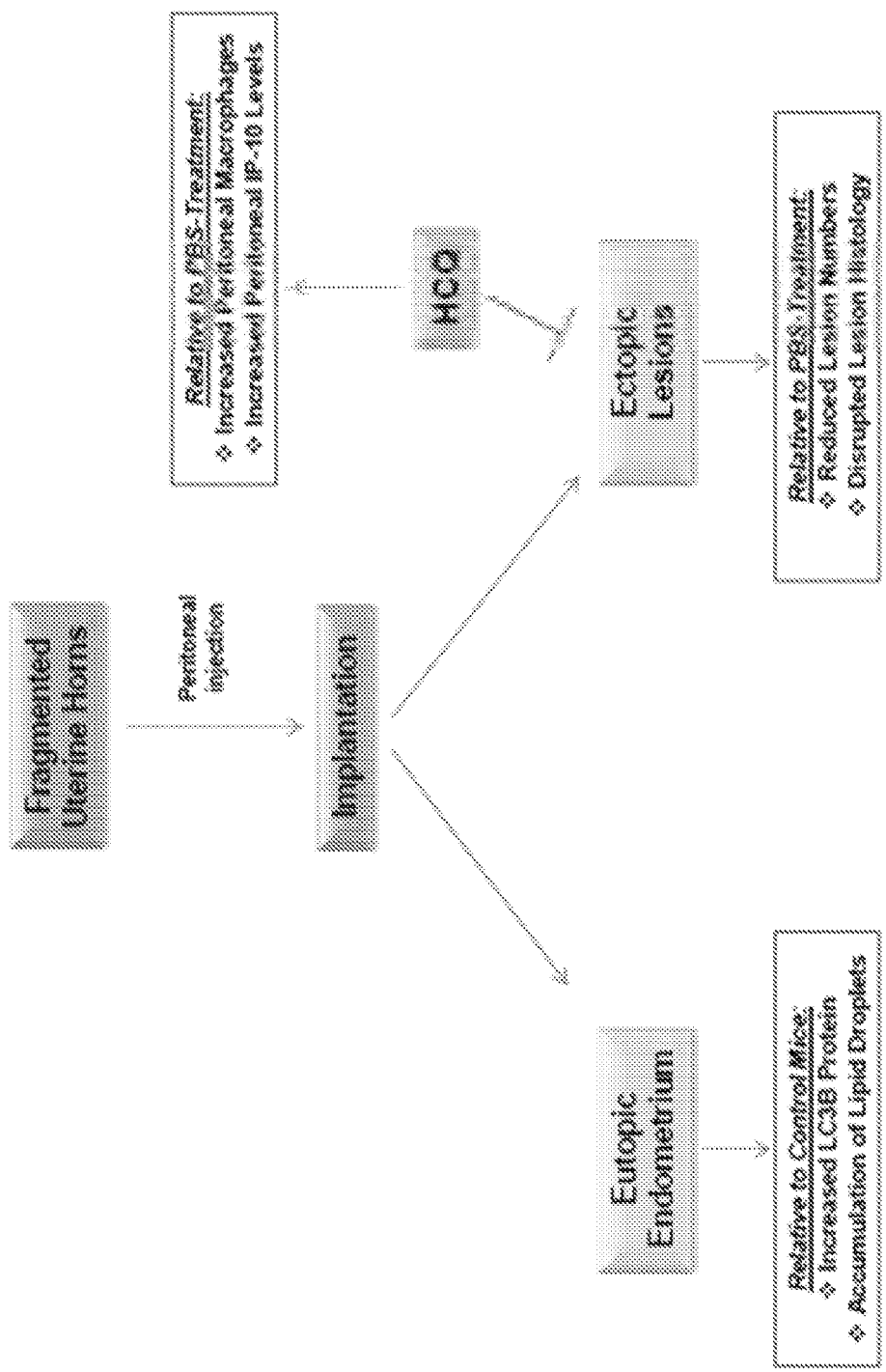
FIG. 33 shows a diagram summary of the observed effect of HCQ on endometriotic lesions.
Figure 36:
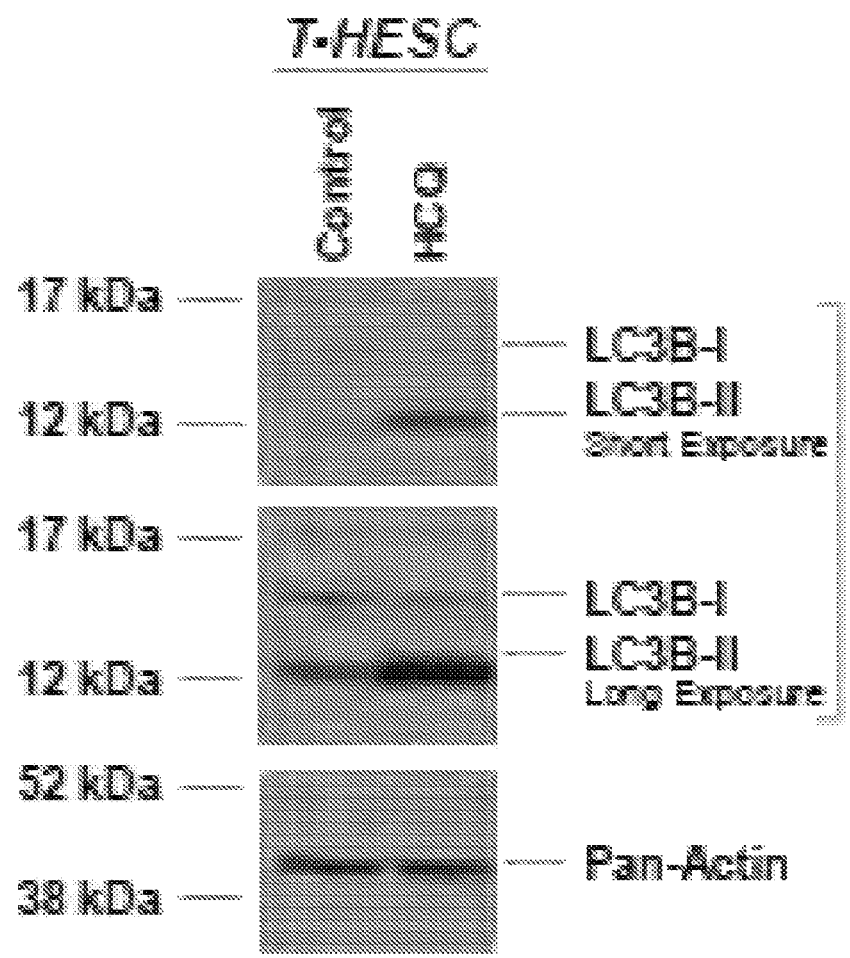
FIG. 36 shows an image of a representative western blot demonstrating LC3B-I, LC3B-II and Pan-actin protein expression control and HCQ treated T-HESC cells.

The cellular localization of LC3B within human eutopic and ectopic endometrium was assessed by applying an immunohistochemical (IHC) approach using a human endometriosis and endometrium tissue microarray. [28] Representative IHC images for endometrium (controls and patients) and lesions (fallopian tubes, ovaries, peritoneal, gastrointestinal, and skin) are shown (FIGS. 31A-31J). It was noted that LC3B was localized primarily to the epithelium although staining was also noted in the stroma. To quantify the intensity of LC3B expression at these specific cellular locations, we segmented the sections using the H-score system into strong, moderate, weak, or no expression (FIGS. 32A-32B). The proportion of strong expression was elevated in the epithelial cells of the proliferative endometrium from cases (40.6%) and those from ovarian and fallopian tube lesions (38.8% and 38.0%, respectively). The endometriotic tissue with the highest proportion of strong stromal expression was the gastrointestinal tract (GI) (17.4%), followed by proliferative endometrium from controls (14.1%), proliferative endometrium from endometriosis patients (13.6%), and secretory endometrium from controls (12.0%) (FIGS. 32A-32B). A significant difference in LC3B expression in the epithelium of secretory endometrium compared to proliferative endometrium (p=0.0193) was observed (FIG. 43B). A significant increase in the expression in the epithelium of fallopian tube and ovarian endometriotic lesions compared to epithelium from the secretory endometrium of controls (p=0.0220 and p=0.0097, respectively) was also observed. In the stroma of peritoneal endometriotic lesions, LC3B was decreased compared to the stroma of proliferative endometrium from controls (p=0.0101). In addition, relative to the stroma, positive LC3B immunostaining was significantly more elevated in the epithelial component of the lesions in the fallopian tube, ovarian, and peritoneum but not in lesions derived from the gastrointestinal tract and the skin (FIG. 43A). Together and without being bound by theory, LC3B expression and localization was predominant in the epithelium relative to the stromal components in all tissue types assessed.

Materials and Methods:

Ethics and Tissue Microarray.

All protocols in this study were approved by the Institutional Review Board (IRB) at the Ponce Research Institute (Ponce, Puerto Rico). Samples in the tissue microarray (TMA) were obtained in a de-identified fashion from archived samples at a private pathology laboratory (Southern Pathology Laboratories in Ponce, Puerto Rico). Details regarding the human tissue microarray (TMA) used in this study have been previously described. [28] Briefly, the TMA contains 164 cores, which is comprised of lesions (from the ovaries (n=29), fallopian tubes (n=16), peritoneum (n=34), skin (n=4), and gastrointestinal tract (n=7)), eutopic endometrium from endometriosis patients (n=22), as well as secretory (n=38) and proliferative (n=14) endometrium from endometriosis-free patients. The patients and controls recruited into this biobank were not currently or have been for at least 3 months prior to surgery on any hormonal medication.

Animal Handling.

C57BL/6 Mouse Model.

Five-week-old C57BL/6 female mice were purchased from Jackson laboratories. All animals were maintained under standard 12 h photoperiod; food and water were available ad libitum throughout the study. All experimental procedures and animal care were approved by the Animal Care and Use Committee (IACUC) of the University of South Florida (R IS00000101), in accordance with the principles described in the Guide for the Care and Use of Laboratory Animals of the National Institutes of Health. All surgical procedures were performed under aseptic conditions using anesthesia. The mouse model of endometriosis was performed as previously described. [19, 20] Donoranimals received a peritoneal injection of 3 µg/mouse of β-estradiol-17-valerate (Sigma, St. Louis, Mo.); the dose utilized was based on previously reported data.20 One week after estrogen injection, donor animals were euthanized and each uterine horn was collected and minced using a Kirkland Tissue Mincer (Kirkland Products) with sterile normal saline. The minced material was centrifuged at 1,500 rpm for 1 min. Endometriosis was induced by injecting the uterine horn fragments intraperitoneally into the recipient animal. Mice were then randomly divided into two groups: HCQ-treatment animals were intraperitoneally injected with 100 µl of 60 mg/kg of HCQ (# AC26301, Fisher Scientific, Pittsburgh, Pa.) while control treatment animals received an intraperitoneal injection of 100 µl sterile PBS. The dose for HCQ utilized was based on previously published data and was comparable to doses used in treating patients with autoimmune diseases. [21] A second HCQ treatment was administered one week after endometriosis induction, using the same dose. Two weeks after induction, mice were euthanized and tissues (including lesions) were snap-frozen into liquid nitrogen. Lesions were measured using a caliper. Volume of the lesions was calculated according to the formula: $4/3\pi r^2 R$. [52]

Balb/c Mouse Model

Eight-week-old Balb/c female mice were obtained from the Charles River Laboratories (Calco, Como, Italy) and handled as previously described [19, 20] and in accordance with the European Union guidelines as well as with the approval of the Institutional Animal Care and Use Committee of San Raffaele Scientific Institute (Protocol n. 484) (Milan, Italy). Briefly, donor mice were injected with 17β-estradiol (AMSA, Rome, Italy; 3 µg/mouse) and sacrificed one week later. The uterus was removed and fragmented, after scraping to remove the myometrium, using scissors. The endometrial tissues were weighed and resuspended in saline with ampicillin (1 mg/ml). Two recipient mice received an intraperitoneal injection, using a syringe containing half of the resuspension (Day 0). Mice were euthanized by administering a lethal dose of anesthetic on day 12. The abdomen was opened and lesions were isolated and collected by an operator blinded to the experiment.

Cell Culture of Life-Extended Human Endometriotic and T-HESC Cells, HCQ Treatment, siRNA Transfection, and Survival Assay.

Primary human endometriotic cells culture conditions and life extension have been previously described. [18] These cells were derived from two different types of lesions (two independent patients) which were assessed separately as described below. Briefly, cells were maintained in MCDB 131:Medium 199 (1:1 ratio) supplemented with 8% FBS, penicillin/streptomycin, and insulin/transferrin/selenium (ITS). Cells were life-extended using SV40 Large T antigen. Retroviral particles generated in HEK293T were used to infect the primary cells. Media containing puromycin (2.5 µg/ml) was used to select primary cells resistant colonies. In addition, we obtained the T-HESC cell line, which are human endometrial stromal cells derived from a uterine myoma (ATCC, Manassas, Va.). This cell line was maintained in phenol red-free DMEM/F12 (1:1) containing 8% charcoal-dextran treated FBS, 500 ng/mL puromycin, 1% ITS+ Premix (BD Bioscience, San Jose, Calif.), and 15 mM HEPES. The cell lines used in the present study were tested to be mycoplasma negative and STR (short tandem repeat) profiled (Genetica DNA Laboratories, Cincinnati, Ohio). Endometriotic cells were seeded at 50,000 cells/well in a 24-well plate, whereas T-HESC cells were seeded at 250,000 cells/well in a 6-well plate. A 50 mM hydroxychloroquine (HCQ) (# AC26301, Fisher Scientific, Pittsburgh, Pa., USA) stock was prepared in phosphate-buffered saline (PBS) (and 0.22 µm filter sterilized); it was used at a final concentration of 25 µM in complete media. [18, 53] Cells were treated for 18 hours with HCQ prior to protein harvest and western blotting analyses. For survival studies, cells were seeded at a density of 5,000 cells/well in a 96-well opaque plate and treated with 25 µM HCQ during five days. Cell viability was then assessed using CellTiter-glo reagent (Promega, Madison, Wis.). [18]

For siRNA transfection studies, T-HESC cells were seeded at 350,000 cells/well in a 6-well plate. After overnight adherence, cells were then transfected with either non-targeting control siRNA, ATG5, beclin-1, ATG7, PIK3C3, or LC3B siRNA according to previously described methods. [18, 54] The day after the second round of siRNA transfection, cells were re-seeded at 5,000 cells/well in opaque 96-well plates. Three days post re-seeding, cell viability was assessed using CellTiter-glo reagent as described above.

Immunohistochemistry of LC3B.

Samples in the TMA were collected in a de-identified fashion from archived samples in a Pathology Lab as described in Human Subjects above. Briefly, slides were deparaffinized and stained using the automated system Ventana Discovery XT (Ventana Medical Systems, Tucson, Ariz.) with EZ Prep solution. The heat-antigen retrieval method was performed at a pH of 8.0. The primary antibody, LC3 (AP1802a) which detects LC3B was obtained from Abgent (San Diego, Calif.) and diluted at a ratio of 1:25 in Dako antibody diluent (Carpenteria, Calif.) followed by a 32 min incubation at room temperature. Human breast cancer tissue was used as a positive control and the primary antibody was omitted for the negative control. Ventana OmniMap Anti-Rabbit Secondary antibody and the Ventana ChromoMap kit as the detection system were used. Hematoxylin was used as the counterstain.

The LC3 stained TMA was then scanned using the Aperio™ ScanScope XT (Vista, Calif.) with a 200× magnification and a 0.8 numerical aperture objective lens via the Basler tri-linear-array detection. Each core was then segmented using the TMA block software associated with the Spectrum program (version 10.2.5.2352) followed by manual segmentation into epithelial and stromal regions under the supervision of a pathologist. Image analysis was performed using an Aperio Positive Pixel Count® v9.0 algorithm with the following thresholds: Hue Value=0.1;

Hue Width=0.5; Color Saturation Threshold=0.04; IWP (High)=220; IWP(Low)=IP(High)=175; IP(low)=ISP (High)= 100; ISP(Low)=0 to segment positive staining of various intensities. The data was then compiled for each core in the separate epithelium and stromal regions, which was represented by percent positivity, then directly correlated with protein expression.

RNA Isolation, Real-Time PCR, and RT2-PCR.

Total RNA was isolated using the RNeasy kit following the manufacturer's instructions (QIAGEN, Valencia, Calif.). RNA concentration and purity was determined using a 1000 NanoDrop (Thermo Scientific, Pittsburgh, Pa.). Lesion mass varied by samples, and this was reflected in the RNA amounts obtained (range of mass: 0.9 mg to 25 mg). Three RNA samples from uterine horns, having a 260/280 ratio higher than 1.8 and a 260/230 ratio higher than 1.7, were selected from recipient, donor, HCQ-treated, and PBS-treated animals (12 samples in total) for RT2-PCR analyses. Synthesis of cDNA was performed using 0.5 µg of total RNA, after DNA elimination step using the RT2 First Strand kit per manufacturer instructions (QIAGEN, Valencia, Calif.). After DNA elimination, the reaction mix was incubated at 42° C. for 15 min, followed by 95° C. for 5 min using a DNA Engine® Peltier Thermal cycler (Bio-Rad, Hercules, Calif.). A total of 102 µl of the cDNA reaction mix was added to the master mix containing 1,248 µl of RNAse-free water and 1,350 µl of 2× RT2 SYBR green master mix. Twenty-five µl of the master mix were carefully added to each well of the RT2 profiler PCR autophagy array. Quantification was performed using the Applied Biosystems cycler (Life Technologies, Grand Island, N.Y.). The PCR cycling program included activation for 10 min at 95° C., followed by 40 cycles for 15 seconds at 95° C. with 1 min at 60° C. The PCR cycling program finalized with a melt curve analysis and data was analyzed using the QIAGEN web-based software.

For real-time PCR studies, the One-step Master Mix (Applied Biosystems, Foster City, Calif.) was utilized with the following probes and primers as previously described: 18 LC3B, Mm00782868_sH; ATG4B, Mm01701111_m1; ATG9A, Mm01264420_m1; ATG5, Mm00504340_m1; ATG7, Mm00512209_m1; ATG3, Mm00471287_m1; PIK3C3, Mm00619489_m1; ULK1, Mm00437238_m1; ATG9B, Mm01157883_g1; Beclin-1, Mm01265461_m1; ATG2B, Mm00512973_m1; ATG4C, Mm01259886_m1; BNIP3, Mm01275600_g1; EIF2AK3, Mm00438700_m1; FAS, Mm01204974_m1; LC3A, Mm00458725_g1; GABARAPL1, Mm00457880_m1; IGF1, Mm00439560_m1; IRGM1, Mm00492596_m1; SQSTM1 (p62), Mm00448091_m1; PRKAA1, Mm01296700_m1; PTEN, Mm00477208_m1. CT values were normalized to β-Actin (Mm00607939_s1) and RNA-fold changes were determined using the $2^{\Delta\Delta Ct}$ equation.

Protein Isolation, SDS-PAGE, and Western Blot Analyses.

Tissues used for protein analyses included uterine horns, ectopic lesions, ovaries, thymus, kidneys, heart, pancreas, spleen, and liver. Samples were flash frozen in liquid nitrogen and stored at −80° C. until use. Tissues were homogenized in ice-cold lysis buffer containing 1% Triton X-100, 50 mM HEPES, 150 mM NaCl, 1 mM MgCl2, 1 mM EGTA, 10% glycerol, and protease inhibitor cocktail (Roche, Indianapolis, Ind.) using a PowerGen 125 homogenizer (Fisher Scientific, Pittsburgh, Pa.). Samples were centrifuged at 14,000 rpm for 10 min at 4° C. The supernatants were collected and total protein concentration was determined using the BCA assay (ThermoScientific, Rockford, Ill.), and a Bio Tek synergy 2 microplate reader (Winooski, Vt.). Samples were normalized and then run onto 10 or 12% SDS-polyacrylamide gels prepared in a Criterion® Cassette system (Bio-Rad, Hercules, Calif.) as previously described. [54] The following antibodies and dilutions were used: LC3B rabbit polyclonal (#2775, 1:1,000), LC3A rabbit monoclonal (#4599 (D50G8), 1:1,000), Beclin-1 rabbit polyclonal (#3738, 1:1,000), GABARAPL1 rabbit monoclonal (#13733 (E1J4E), 1:1,000), AMPKα rabbit monoclonal (#2603 (23A3), 1:500), FOXO1 rabbit monoclonal (#2880 (C29H4), 1:1,000), and Pan-Actin rabbit polyclonal (#4968, 1:500) were all obtained from Cell Signaling Technology (Danvers, Mass.). The p62 mouse monoclonal antibody (#610832, 1:1,000) was obtained from BD Biosciences (San Jose, Calif.).

Hematoxylin/Eosin Staining, Tissue Microarray Construction, and Immunohistochemistry.

Collected samples were immediately preserved in 10% neutral buffered formalin at the animal facility. Samples were embedded in paraffin, sectioned, and transferred to slides for hematoxylin/eosin and immunohistochemical staining. A pathologist reviewed each case and delimited the region of interest, containing epithelial and stromal cells, for each specimen. A mouse tissue microarray was prepared at the Tissue Core Facility at the Moffitt Cancer Center. The mouse tissue microarray contained a total of 113 core samples, which included 10 uterine horns and 10 ovaries from both PBS and HCQ treated mice. As control specimens for the utilized antibodies, the TMA included mouse mammary tissue, liver, small intestine, and lymph nodes from a PBS treated mouse. Lesions were analyzed from independent blocks. Slides were stained using a Leica Bond RX automated system (Leica Biosytems, Buffalo Grove, Ill.) following manufacturers instructions with proprietary reagents. Slides were deparaffinized on an automated system with Dewax Solution (Leica Biosystems). The antigen retrieval method used for Progesterone Receptor (PR) was enzymatic with Enzyme Solution 1 at 15 min (Leica), for vimentin and Estrogen Receptor (ER) was heat induced with Epitope Retrieval Solution 1 at 20 min (Leica), for cytokeratin 8 (CK-8) was heat induced with Epitope Retrieval Solution at 10 min (Leica), and for LC3B was heat-induced with Epitope Retrieval Solution 1 at 10 min (Leica Biosystems). All antibodies were diluted in Dako antibody diluent (Carpenteria, Calif.): PR (# ab131486, 1:500, Abcam, Cambridge, Mass.), vimentin (#5741 (D21H3), 1:100, Cell Signaling, Danvers, Mass.), ERα (# ab32063 (E115), 1:200, Abcam, Cambridge, Mass.), Cytokeratin-8 (# ab53280 (EP1628Y), 1:200, Abcam, Cambridge, Mass.), and LC3B (# ab51520, 1:1,500, Abcam, Cambridge, Mass.) and incubated for 30 min. The Leica Bond Polymer Refine Detection System was used with a polymer incubation for 8 min. Hematoxylin was used as counterstain and slides were dehydrated and covered with a coverslip, following standard histological protocol.

Analysis of Murine Peritoneal Inflammatory Molecules.

After animals were euthanized, 1 ml of sterile PBS was injected into the peritoneal cavity, the abdominal area was gently massaged, and the fluid collected. The collected fluid was centrifuged at 1,390 rpm for 5 min at 4° C. and the resulting supernatant was then stored at −80° C. Levels of chemokines and cytokines were analyzed using a MCY-TOMAG-70K-PX32 (Millipore, Billerica, Mass.) following manufacturer's instructions. Briefly, 200 µl of wash buffer was added to each well and incubated for 10 min at room temperature in a plate shaker. After incubation, the wash buffer was decanted and the plate was inverted and tapped on absorbent towel several times. Then, 25 µl of assay buffer was added to each well followed by 25 µl of concentration standards, assay controls, or samples. The premixed bottle was vortexed and 25 µl of the beads were added to each well. The plate was incubated overnight at 4° C., protected from light. Then the plate was incubated for 1 min on the hand-held magnet and the well content was gently decanted and tapped on absorbent pads. Each well was washed twice using 200 µl of wash buffer, followed by the incubation on the hand-held magnet. Antibody detection solution was allowed to warm to room temperature, and then 25 µl was added to each well and incubated for 1 h at room temperature on a plate shaker, protected from light. Next, 25 µl of Streptavidin-Phycoerythrin was added to each well containing the detection antibodies and incubated for 30 min at room temperature protected from light on a plate shaker. After the incubation, the plate was washed twice as previously described and 150 µl of Sheath Fluid was added to each well. The plate was analyzed using MAGPIX™ instrument and xPONENT software solutions, version 4.2.

Flow Cytometry.

The pellet obtained after centrifugation of the peritoneal fluid wash (see above) was utilized for macrophage staining. When necessary, red blood cell lysis was performed according to the manufacturer's protocol (eBioscience, San Diego, Calif.). The cell pellets were resuspended in 1 ml cold PBS and transferred to flow cytometry tubes. Samples were centrifuged for 1 min at 1,390 rpm. The supernatant was decanted and cells were resuspended in 100 µl of PBS. Cells were blocked using 0.5 µg of Mouse BD Fc, Block™ (#553141, BD Pharmingen, San Jose, Calif.) for 5 min on ice. The cells were incubated in 0.4 µg of APC Rat anti-mouse CD11b clone M1/70 (#553312, BD Pharmingen, San Jose, Calif.) and anti mPE-F4/80/EMR1 (# FAB5580C, R&D Systems, Minneapolis, Minn.)) at room temperature for 30 min, protected from light. After incubation, 700 µl of PBS was added to each tube and centrifuged for 1 min at 4° C. The supernatant was decanted, and the cells were resuspended in 300 µl in PBS and analyzed by flow cytometry.

Transmission Electron Microscopy.

Following induction of anesthesia, the abdominal cavity of the mice was opened to expose the uterine horns. Both uterine horns were removed and cut in cross sections of 2-3 mm long pieces, which were then rinsed in 0.1 M phosphate buffer to remove excess blood, and placed in 2.5% glutaraldehyde in 0.1 M sodium phosphate buffer, pH 7.2 at 4° C. The tissue was fixed in glutaraldehyde at 4° C. for 24 h. Following fixation, the tissue was rinsed in buffer, sliced into 1 mm thick rings and post-fixed in 1% osmium tetroxide at 4° C. for 2 h. Following buffer and distilled water rinses, the tissue was dehydrated through a graded series of acetone dilutions, cleared with propylene oxide, infiltrated overnight, embedded in LX 112 epoxy resin mix (Ladd Research, Williston, Vt.) and polymerized at 70° C. Entire cross sections of the uterine horns were obtained at 0.25 µm-0.35 µm thickness and 70-80 nm thickness, and stained with 1% toluidine blue stain (for light microscopy) or 8% uranyl acetate and Reynold's lead citrate (for electron microscopy) respectively. The endometrium of both control and experimental animals was observed and photographed using an FEI Morgagni TEM (Hillsboro, Oreg.) with an AMT ActiveVu camera (Woburn, Mass.).

Statistical Analyses.

All analyses were performed using GraphPad Prism software (version 6.04, La Jolla, Calif.). To calculate the significance of the observed disorganization of epithelial cells in eutopic endometria from endometriosis-induced mice treated with HCQ (compared to those treated with PBS, as a control), we used the Fisher's exact test. All other statistical analyses were calculated using the non-parametric student t-test and error bars displayed represent standard errors of the mean (SEM). Statistical significance was set at $p \leq 0.05$ (* indicates $p \leq 0.05$,  indicates $p \leq 0.01$, * indicates $p \leq 0.001$, and **** indicates $p \leq 0.0001$).

REFERENCES

1. Giudice L C, Kao L C. Endometriosis. *Lancet*. 2004; 364: 1789-1799.
2. Bulun S E. Endometriosis. *N Engl J Med*. 2009; 360: 268-279.
3. Giudice L C. Clinical practice. Endometriosis. *N Engl J Med*. 2010; 362: 2389-2398.
4. Sourial S, Tempest N, Hapangama D K. Theories on the pathogenesis of endometriosis. *Int J Reprod Med*. 2014; 2014: 179515.
5. Sampson J A. Peritoneal endometriosis due to the menstrual dissemination of endometrial tissue into the peritoneal cavity. *American Journal of Obstetrics and Gynecology*. 1927; 14: 422-469.
6. Baldi A, Campioni M, Signorile P G. Endometriosis: pathogenesis, diagnosis, therapy and association with cancer (review). *Oncol Rep*. 2008; 19: 843-846.
7. Vercellini P, Vigano P, Somigliana E, Fedele L. Endometriosis: pathogenesis and treatment. *Nat Rev Endocrinol*. 2014; 10: 261-275.
8. Fung C, Lock R, Gao S, Salas E, Debnath J. Induction of autophagy during extracellular matrix detachment promotes cell survival. *Mol Biol Cell*. 2008; 19: 797-806.
9. Lamb C A, Yoshimori T, Tooze S A. The autophagosome: origins unknown, biogenesis complex. *Nat Rev Mol Cell Biol*. 2013; 14: 759-774.
10. Feng Y, He D, Yao Z, Klionsky D J. The machinery of macroautophagy. *Cell Res*. 2014; 24: 24-41.
11. Legakis J E, Yen W L, Klionsky D J. A cycling protein complex required for selective autophagy. *Autophagy*. 2007; 3: 422-432.
12. Pelch K E, Schroder A L, Kimball P A, Sharpe-Timms K L, Davis J W, Nagel S C. Aberrant gene expression profile in a mouse model of endometriosis mirrors that observed in women. *Fertil Steril*. 2010; 93: 1615-1627 e1618.
13. Choi J, Jo M, Lee E, Kim H J, Choi D. Differential induction of autophagy by mTOR is associated with abnormal apoptosis in ovarian endometriotic cysts. *Mol Hum Reprod*. 2014; 20: 309-317.
14. Allavena G, Carrarelli P, Del Bello B, Luisi S, Petraglia F, Maellaro E. Autophagy is upregulated in ovarian endometriosis: a possible interplay with p53 and heme oxygenase-1. *Fertil Steril*. 2015; 103: 1244-1251 e1241.
15. Al-Bari M A. Chloroquine analogues in drug discovery: new directions of uses, mechanisms of actions and toxic manifestations from malaria to multifarious diseases. *J Antimicrob Chemother*. 2015; 70: 1608-1621.
16. Amaravadi R K, Lippincott-Schwartz J, Yin X M, Weiss W A, Takebe N, Timmer W, et al. Principles and current strategies for targeting autophagy for cancer treatment. *Clin Cancer Res*. 2011; 17: 654-666.
17. Calabretta B, Salomoni P. Inhibition of autophagy: a new strategy to enhance sensitivity of chronic myeloid leukemia stem cells to tyrosine kinase inhibitors. *Leuk Lymphoma*. 2011; 52 Suppl 1:54-59.

18. Bauckman K A, Haller E, Flores I, Nanjundan M. Iron modulates cell survival in a Ras- and MAPK-dependent manner in ovarian cells. *Cell Death Dis.* 2013; 4: e592.
19. Somigliana E, Vigano P, Rossi G, Carinelli S, Vignali M, Panina-Bordignon P. Endometrial ability to implant in ectopic sites can be prevented by interleukin-12 in a murine model of endometriosis. *Hum Reprod.* 1999; 14: 2944-2950.
20. Mariani M, Vigano P, Gentilini D, Camisa B, Caporizzo E, Di Lucia P, et al. The selective vitamin D receptor agonist, elocalcitol, reduces endometriosis development in a mouse model by inhibiting peritoneal inflammation. *Hum Reprod.* 2012; 27: 2010-2019.
21. McAfee Q, Zhang Z, Samanta A, Levi S M, Ma X H, Piao S, et al. Autophagy inhibitor Lys05 has single-agent antitumor activity and reproduces the phenotype of a genetic autophagy deficiency. *Proc Natl Acad Sci USA.* 2012; 109: 8253-8258.
22. Bacci M, Capobianco A, Monno A, Cottone L, Di Puppo F, Camisa B, et al. Macrophages are alternatively activated in patients with endometriosis and required for growth and vascularization of lesions in a mouse model of disease. *Am J Pathol.* 2009; 175: 547-556.
23. Jang C H, Choi J H, Byun M S, Jue D M. Chloroquine inhibits production of TNF-alpha, IL-1beta and IL-6 from lipopolysaccharide-stimulated human monocytes/macrophages by different modes. *Rheumatology* (Oxford). 2006; 45: 703-710.
24. Dinulescu D M, Ince T A, Quade B J, Shafer S A, Crowley D, Jacks T. Role of K-ras and Pten in the development of mouse models of endometriosis and endometrioid ovarian cancer. *Nat Med.* 2005; 11: 63-70.
25. Matsuzaki S, Canis M, Pouly J L, Botchorishvili R, Dechelotte P J, Mage G. Differential expression of genes in eutopic and ectopic endometrium from patients with ovarian endometriosis. *Fertil Steril.* 2006; 86: 548-553.
26. Meola J, Rosa e Silva J C, Dentillo D B, da Silva W A, Jr., Veiga-Castelli L C, Bernardes L A, et al. Differentially expressed genes in eutopic and ectopic endometrium of women with endometriosis. *Fertil Steril.* 2010; 93: 1750-1773.
27. Klionsky D J, Abdalla F C, Abeliovich H, Abraham R T, Acevedo-Arozena A, Adeli K, et al. Guidelines for the use and interpretation of assays for monitoring autophagy. *Autophagy.* 2012; 8: 445-544.
28. Colon-Diaz M, Baez-Vega P, Garcia M, Ruiz A, Monteiro J B, Fourquet J, et al. HDAC1 and HDAC2 are differentially expressed in endometriosis. *Reprod Sci.* 2012; 19: 483-492.
29. Lee S J, Silverman E, Bargman J M. The role of antimalarial agents in the treatment of SLE and lupus nephritis. *Nat Rev Nephrol.* 2011; 7: 718-729.
30. Nothnick W B. Treating endometriosis as an autoimmune disease. *Fertil Steril.* 2001; 76: 223-231.
31. Nirgianakis K, Bersinger N A, McKinnon B, Kostov P, Imboden S, Mueller M D. Regression of the inflammatory microenvironment of the peritoneal cavity in women with endometriosis by GnRHa treatment. *Eur J Obstet Gynecol Reprod Biol.* 2013; 170: 550-554.
32. Sinaii N, Cleary S D, Ballweg M L, Nieman L K, Stratton P. High rates of autoimmune and endocrine disorders, fibromyalgia, chronic fatigue syndrome and atopic diseases among women with endometriosis: a survey analysis. *Hum Reprod.* 2002; 17: 2715-2724.
33. Kvaskoff M, Mu F, Terry K L, Harris H R, Poole E M, Farland L, et al. Endometriosis: a high-risk population for major chronic diseases? *Hum Reprod Update.* 2015; 21: 500-516.
34. Ben-Zvi I, Kivity S, Langevitz P, Shoenfeld Y. Hydroxychloroquine: from malaria to autoimmunity. *Clin Rev Allergy Immunol.* 2012; 42: 145-153.
35. von Adamek E V, Simoes M J, Freitas V, Patriarca M T, Soares J M, Jr., Baracat E C. Lysosomal evaluation of endometrioma capsule epithelium and endometrium of patients with or without endometriosis. *Clin Exp Obstet Gynecol.* 2005; 32: 27-30.
36. Lee I H, Kawai Y, Fergusson M M, Rovira, I I, Bishop A J, Motoyama N, et al. Atg7 modulates p53 activity to regulate cell cycle and survival during metabolic stress. *Science.* 2012; 336: 225-228.
37. Taub D D, Lloyd A R, Conlon K, Wang J M, Ortaldo J R, Harada A, et al. Recombinant human interferon-inducible protein 10 is a chemoattractant for human monocytes and T lymphocytes and promotes T cell adhesion to endothelial cells. *J Exp Med.* 1993; 177: 1809-1814.
38. Strieter R M, Kunkel S L, Arenberg D A, Burdick M D, Polverini P J. Interferon gamma-inducible protein 10 (IP-10), a member of the C-X-C chemokine family, is an inhibitor of angiogenesis. *Biochem Biophys Res Commun.* 1995; 210: 51-57.
39. Galleri L, Luisi S, Rotondi M, Romagnani P, Cobellis L, Serio M, et al. Low serum and peritoneal fluid concentration of interferon-gamma-induced protein-10 (CXCL10) in women with endometriosis. *Fertil Steril.* 2009; 91: 331-334.
40. Mei J, Zhu X Y, Jin L P, Duan Z L, Li D J, Li M Q. Estrogen promotes the survival of human secretory phase endometrial stromal cells via CXCL12/CXCR4 up-regulation-mediated autophagy inhibition. *Hum Reprod.* 2015.
41. Burney R O, Talbi S, Hamilton A E, Vo K C, Nyegaard M, Nezhat C R, et al. Gene expression analysis of endometrium reveals progesterone resistance and candidate susceptibility genes in women with endometriosis. *Endocrinology.* 2007; 148: 3814-3826.
42. Marino G, Uria J A, Puente X S, Quesada V, Bordallo J, Lopez-Otin C. Human autophagins, a family of cysteine proteinases potentially implicated in cell degradation by autophagy. *J Biol Chem.* 2003; 278: 3671-3678.
43. Geng J, Klionsky D J. The Atg8 and Atg12 ubiquitin-like conjugation systems in macroautophagy. 'Protein modifications: beyond the usual suspects' review series. *EMBO Rep.* 2008; 9: 859-864.
44. Li M, Hou Y, Wang J, Chen X, Shao Z M, Yin X M. Kinetics comparisons of mammalian Atg4 homologues indicate selective preferences toward diverse Atg8 substrates. *J Biol Chem.* 2011; 286:7327-7338.
45. Wordinger R J, Dickey J F, Ellicott A R. Histochemical evaluation of the lipid droplet content of bovine oviductal and endometrial epithelial cells. *J Reprod Fertil.* 1977; 49: 113-114.
46. Shibata M, Yoshimura K, Tamura H, Ueno T, Nishimura T, Inoue T, et al. LC3, a microtubule-associated protein1A/B light chain3, is involved in cytoplasmic lipid droplet formation. *Biochem Biophys Res Commun.* 2010; 393: 274-279.
47. Taylor E, Williams C. Surgical treatment of endometriosis: location and patterns of disease at reoperation. *Fertil Steril.* 2010; 93: 57-61.

48. Laux-Biehlmann A, d'Hooghe T, Zollner T M. Menstruation pulls the trigger for inflammation and pain in endometriosis. *Trends Pharmacol Sci.* 2015; 36: 270-276.
49. Hadfield R, Mardon H, Barlow D, Kennedy S. Delay in the diagnosis of endometriosis: a survey of women from the USA and the UK. *Hum Reprod.* 1996; 11: 878-880.
50. Costedoat-Chalumeau N, Dunogue B, Leroux G, Morel N, Jallouli M, Le Guern V, et al. A Critical Review of the Effects of Hydroxychloroquine and Chloroquine on the Eye. *Clin Rev Allergy Immunol.* 2015.
51. Janssen N M, Genta M S. The effects of immunosuppressive and anti-inflammatory medications on fertility, pregnancy, and lactation. *Arch Intern Med.* 2000; 160: 610-619.
52. Bilotas M A, Olivares C N, Ricci A G, Baston J I, Bengochea T S, Meresman G F, et al. Interplay between Endometriosis and Pregnancy in a Mouse Model. *PLoS One.* 2015; 10: e0124900.
53. Perecko T, Kassab R B, Vasicek O, Pekarova M, Jancinova V, Lojek A. The effects of chloroquine and hydroxychloroquine on nitric oxide production in RAW 264.7 and bone marrow-derived macrophages. *Folia Biol (Praha).* 2014; 60 Suppl 1: 39-44.
54. Smith D M, Patel S, Raffoul F, Haller E, Mills G B, Nanjundan M. Arsenic trioxide induces a beclin-1-independent autophagic pathway via modulation of SnoN/SkiL expression in ovarian carcinoma cells. *Cell Death Differ.* 2010; 17: 1867-1881.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10695341B2). An electronic copy of the "Sequence Listing" will also be available from the USPTO upon request and payment of the fee set forth in 37 CFR 1.19(b)(3).

We claim:

1. A method of treating endometriosis in a subject in need thereof comprising:
   administering an autophagic inhibitor to the subject in an amount effective to treat endometriosis in the subject.

2. The method of claim 1, wherein the autophagic inhibitor is selected from the group consisting of chloriquine, Lys05, hydroxychloriquine, pharmaceutically acceptable salts thereof, ATG5 siRNA, ATG7 siRNA, or combinations thereof.

3. The method of claim 1, wherein the autophagic inhibitor is hydroxychloriquine.

4. The method of claim 1, wherein the effective amount ranges from about 1 mg/kg to about 200 mg/kg.

5. The method of claim 1, wherein the effective amount is administered in a dosage form formulated for oral, vaginal, intravenous, transdermal, subcutaneous, intraperitoneal, or intramuscular administration.

6. A method comprising:
   contacting an endometriotic lesion cell with an autophagic inhibitor in an amount effective to treating the edometriotic lesion.

7. The method of claim 6, wherein contacting an endometriotic lesion cell with an effective amount of an autophagic inhibitor prevents recurrance of an endometriotic lesion cell.

8. The method of claim 6, wherein the autophagic inhibitor is selected from the group consisting of chloriquine, Lys05, hydroxychloriquine, pharmaceutically acceptable salts thereof, ATG5 siRNA, ATG7 siRNA, or combinations thereof.

9. The method of claim 6, wherein the autophagic inhibitor is hydroxychloriquine.

10. The method of claim 6, wherein the effective amount ranges from about 1 mg/kg to about 200 mg/kg.

11. The method of claim 6, wherein the endometriotic lesion cell has greater expression as compared to a control cell of at least one autophagic marker selected from the group consisting of ATG7, ATG5, and hVps34.

* * * * *